[19] United States Patent
Kim et al.

[11] Patent Number: 5,395,947
[45] Date of Patent: Mar. 7, 1995

[54] PLATINUM(II) COMPLEX AND PROCESSES FOR PREPARING THE SAME

[75] Inventors: Dae-Kee Kim; Ganghyeok Kim; Jongsik Gam, all of Suwon; Yong B. Cho, Anyang; Hun T. Kim, Seoul; Joo H. Tai, Seoul; Key H. Kim, Seoul, all of Rep. of Korea

[73] Assignee: Sunkyong Industries, Ltd., Kyungki-do, Rep. of Korea

[21] Appl. No.: 117,096

[22] Filed: Sep. 14, 1993

[30] Foreign Application Priority Data

Mar. 23, 1991 [KR] Rep. of Korea ............ 91-4627
May 3, 1991 [KR] Rep. of Korea ............ 91-7207
Jul. 31, 1991 [KR] Rep. of Korea ............ 91-13205
Nov. 11, 1991 [KR] Rep. of Korea ............ 91-19969
Dec. 27, 1991 [KR] Rep. of Korea ............ 91-24631
Dec. 27, 1991 [KR] Rep. of Korea ............ 91-24632

[51] Int. Cl.$^6$ ................ C07F 15/00; C07D 317/00
[52] U.S. Cl. ................ 549/206; 549/450; 549/451; 556/137
[58] Field of Search ........... 556/137; 514/184, 492; 549/206, 450, 457

[56] References Cited

U.S. PATENT DOCUMENTS 4,665,210  5/1987  Bitha et al. ............ 556/137
4,730,069  3/1988  Kolar et al. ............ 556/137
4,783,452 11/1988  Haines et al. ........... 514/184
4,870,070  9/1989  Bitha et al. ............ 514/184

OTHER PUBLICATIONS

Rosenberg et al., Nature 222, 385, 1969.
Peter W. Feit et al., J. Med. Chem. 7, 14, 1964.
Cancer Chemotheraphy Reports, Part 3, 3(2), 7, 1972.

*Primary Examiner*—José G. Dees
*Assistant Examiner*—Porfirio Nazario-Gonzalez
*Attorney, Agent, or Firm*—Anderson Kill Olick & Oshinsky

[57] ABSTRACT

Disclosed herein are novel platinum(II) complexes having a potent anti-tumor activity which are represented by the formula (1),

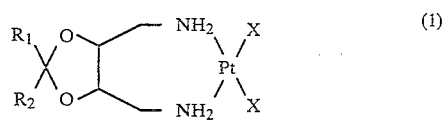

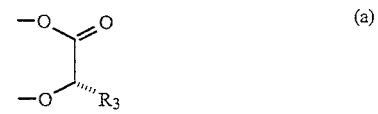

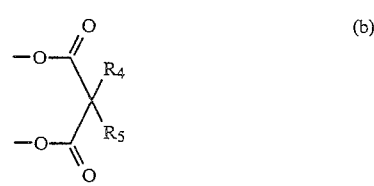

wherein $R_1$ and $R_2$, which may be the same or different, are a hydrogen atom or a $C_{1-4}$ alkyl group, respectively, or jointly form a cycloalkane group together with the carbon atom attached thereto; two Xs jointly form a group represented by formula (a) or (b) wherein, $R_3$ is a hydrogen atom or a methyl group; $R_4$ and $R_5$, which may be the same or different, are a hydrogen atom or a $C_{1-4}$ alkyl group, respectively, or jointly form a cyclobutane together with the carbon thereto; and the absolute configurations at the respective chiral centers in the 4,5-bis(aminomethyl)-1,3-dioxolane moiety are (4R,5R) or (4S,5S); processes for the preparing the same; and their use for treating animal or human cancer. Further, disclosed herein are novel intermediates useful for the preparation of the platinum(II) complexes and processes for preparing said intermediates.

17 Claims, No Drawings

PLATINUM(II) COMPLEX AND PROCESSES FOR PREPARING THE SAME

FIELD OF THE INVENTION

The present invention relates to novel platinum(II) complexes which show a potent anti-tumor activity with low toxicity and good solubility in water, processes for preparing the same, and an anti-tumor agent comprising said platinum(II) complex as an active ingredient. The present invention also relates to novel intermediates useful for the preparation of said platinum(II) complexes.

DESCRIPTION OF THE PRIOR ART

Platinum coordination complexes, cytotoxic agents first identified by Rosenberg and his coworkers in 1965, are fully documented in the literature (B. Rosenberg et al., Nature, 222, 385(1969)). One of the best known platinum coordination complexes is cis-dichlorodiammineplatinum(II), also known as cis-DDP or cisplatin. Cisplatin has proven to be effective on a variety of human cancers such as testicular, ovarian, bladder, and head and neck cancer; however, its serious dose-limiting toxicities include severe nephrotoxicity, myelosuppression, nausea and vomiting, and neurotoxicity, especially ototoxicity and peripheral neuropathy. Further, cisplatin is not very soluble in water and dissolves in water very slowly, which makes its intravenous administration difficult. Therefore, numerous cisplatin derivatives have been synthesized in a search for improved anti-cancer agents with reduced toxicity and improved water-solubility. However, no platinum coordination complex which meets these criteria has been developed.

For instance, U.S. Pat. No. 4,783,452 issued to A. H. Haines et al. discloses cisplatin-derived compounds, having the formula of:

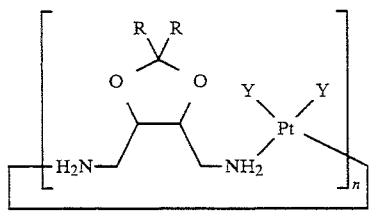

wherein both Y groups are either chloride or bromide; the two R groups are both methyl or one of them is hydrogen and the other is phenyl; and n is 1. Such compounds are stated to have potent anti-tumor activity, although they still have severe nephrotoxicity and poor water solubility problems.

SUMMARY OF THE INVENTION

A primary objective of the present invention is to provide novel platinum(II) complexes which have potent anti-tumor activities with low toxicity and good water-solubility, which are useful for the treatment of human cancers, represented by the formula of:

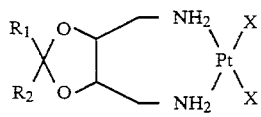  (1)

wherein:

$R_1$ and $R_2$, which may be the same or different, are a hydrogen atom or a $C_{1-4}$ alkyl group, respectively, or jointly form a cycloalkane group together with a carbon atom attached thereto;

two Xs jointly form a group represented by the formula(a) or (b) as follows:

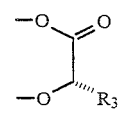  (a)

or

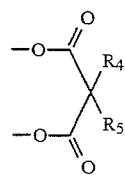  (b)

wherein $R_3$ is a hydrogen atom or a methyl group; $R_4$ and $R_5$, which may be the same or different, are a hydrogen atom or a $C_{1-4}$ alkyl group, respectively, or jointly form a cyclobutane together with a carbon attached thereto; and, the absolute configurations at the respective chiral centers in the 4,5-bis(aminomethyl)-1,3-dioxolane moiety are (4R, 5R) or (4S, 5S) represented by:

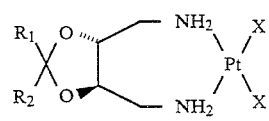  (4R, 5R)

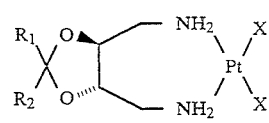  (4S, 5S)

Further, among the compounds of the formula(1), those with the two Xs which jointly form a group of the formula(a) in which $R_1$ and $R_2$ are different exist as one of the following stereoisomers represented by:

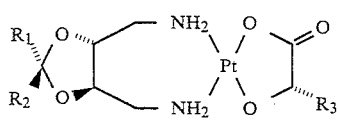  (1a1)

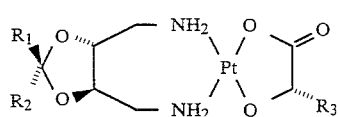  (1a2)

The platinum complexes of the present invention comprise all of the above stereoisomers of the formulas(1a1) and (1a2) and mixtures thereof. For the purpose of the present invention, however, there will be made no distinction between the two isomers. For a mixture of said stereoisomers of formulas(1a1) and (1a2) is not readily separable; and it is believed that the two stereoisomers have an equivalent level of anti-tumor activity.

Another objective of the present invention is to provide processes for preparing said platinum(II) complexes of formula(1).

A further objective of the present invention is to provide novel intermediates useful for said processes and processes for preparing other upstream intermediates.

A still further objective of the present invention is to provide an anti-cancer agent comprising said platinum(II) complex as an active ingredient.

DETAILED DESCRIPTION OF THE INVENTION

The platinum(II) complexes of the formula(1) wherein the absolute configurations at the respective chiral centers in 4,5-bis(aminomethyl)-1,3-dixolane moiety are (4R, 5R), show more potent anti-tumor activity than the compounds having the (4S, 5S) moiety. Even among the (4R, 5R)-compounds, possessed with still further effective anti-tumor activity are those wherein $R_1$ and $R_2$ jointly form a cycloalkane such as a cyclopentane or cyclohexane group; those wherein $R_1$ and $R_2$ are both methyl or ethyl group; those wherein either $R_1$ or $R_2$ is an ethyl group and the other is a methyl group, or one of $R_1$ and $R_2$ is an ethyl or isopropyl group and the other is a hydrogen atom; and, those wherein two Xs jointly form the group of formula(a) wherein $R_3$ is a hydrogen atom, or the group of formula(b) wherein both $R_4$ and $R_5$ is hydrogen.

Most of the compounds represented by formula(1) are soluble in water. Particularly, the compounds having the $R_1$ group which is different from the $R_2$ group show a better water-solubility; and the shorter the alkyl chain length of $R_1$ or $R_2$ group is, the higher their water-solubility is.

It is further important to note that, the compounds of formula(1) show very low nephrotoxicity.

Representative compounds of the present invention include:
(glycolato-O,O')[(4R,5R)-4,5-bis(aminomethyl)-1,3-dioxolane]platinum(II);
(glycolato-O,O')[(4R,5R)-4,5-bis(aminomethyl)-2,2-dimethyl-1,3-dioxolane]platinum(II);
(glycolato-O,O')[(4R,5R)-4,5-bis(aminomethyl)-1,3-dioxolane-2-spiro-1'-cyclopentane]platinum(II);
(glycolato-O,O'){cyclohexanespiro-2'-[(4'R,5'R)-4',5'-bis-(aminomethyl)-1'3'-dioxolane]}platinum(II);
(glycolato-O,O')[(4R,5R)-4,5-bis(aminomethyl)-2-methyl-1,3-dioxolane]platinum(II);
(glycolato-O,O')[(4R,5R)-4,5-bis(aminomethyl)-2-ethyl-1,3-dioxolane]platinum(II);
(glycolato-O,O')[(4R,5R)-4,5-bis(aminomethyl)-2-isopropyl-1,3-dioxolane]platinum(II);
(glycolato-O,O')[(4R,5R)-4,5-bis(aminomethyl)-2,2-diethyl-1,3-dioxolane]platinum(II);
(glycolato-O,O')[(4R,5R)-4,5-bis(aminomethyl)-2-ethyl-2-methyl-1,3-dioxolane]platinum(II);
(glycolato-O,O')[(4R,5R)-4,5-bis(aminomethyl)-2-propyl-1,3-dioxolane]platinum(II);
(glycolato-O,O')[(4R,5R)-4,5-bis(aminomethyl)-2-isobutyl-1,3-dioxolane]platinum(II);
(glycolato-O,O')[(4R,5R)-4,5-bis(aminomethyl)-2-tert-butyl-1,3-dioxolane]platinum(II);
cis-cyclobutane-1,1-dicarboxylato[(4R,5R)-4,5-bis-(aminomethyl)-2-methyl-1,3-dioxolane]platinum(II);
cis-cyclobutane-1,1-dicarboxylato[(4R,5R)-4,5-bis-(aminomethyl)-1,3-dioxolane]platinum(II);
cis-cyclobutane-1,1-dicarboxylato[(4R,5R)-4,5-bis-(aminomethyl)-2-ethyl-1,3-dioxolane]platinum(II);
cis-cyclobutane-1,1-dicarboxylato[(4R,5R)-4,5-bis-(aminomethyl)-2,2-dimethyl-1,3-dioxolane]platinum(II);
cis-cyclobutane-1,1-dicarboxylato[(4R,5R)-4,5-bis-(aminomethyl)-2-isopropyl-1,3-dioxolane]platinum(II);
cis-cyclobutane-1,1-dicarboxylato[(4R,5R)-4,5-bis-(aminomethyl)-1,3-dioxolane-2-spiro-1'-cyclopentane]platinum(II); and
cis-cyclobutane-1,1-dicarboxylato[(4R,5R)-4,5-bis-(aminomethyl)-1,3-dioxolane-2-spiro-1'-cyclohexane]platinum(II).

More preferred compounds include:
(glycolato-O,O')[(4R,5R)-4,5-bis(aminomethyl)-1,3-dioxolane-2-spiro-1'-cyclopentane]platinum(II);
(glycolato-O,O'){cyclohexanespiro-2'-[(4'R,5'R)-4',5'-bis-(aminomethyl)-1'3'-dioxolane]}platinum(II);
(glycolato-O,O')[(4R,5R)-4,5-bis(aminomethyl)-2-methyl-1,3-dioxolane]platinum(II);
(glycolato-O,O')[(4R,5R)-4,5-bis(aminomethyl)-2-isopropyl-1,3-dioxolane]platinum(II);
(glycolato-O,O')[(4R,5R)-4,5-bis(aminomethyl)-2,2-diethyl-1,3-dioxolane]platinum(II);
(glycolato-O,O')[(4R,5R)-4,5-bis(aminomethyl)-2-ethyl-2-methyl-1,3-dioxolane]platinum(II);
(glycolato-O,O')[(4R,5R)-4,5-bis(aminomethyl)-2-propyl-1,3-dioxolane]platinum(II);
cis-cyclobutane-1,1-dicarboxylato[(4R,5R)-4,5-bis-(aminomethyl)-2-ethyl-1,3-dioxolane]platinum(II)
cis-malonato[(4R,5R)-4,5-bis(aminomethyl)-2,2-diethyl-1,3-dioxolane]platinum(II)
cis-malonato[(4R,5R)-4,5-bis(aminomethyl)-2-isopropyl-1,3-dioxolane]platinum(II)
cis-malonato[(4R,5R)-4,5-bis(aminomethyl)-1,3-dioxolane-2-spiro-1'-cyclopentane]platinum(II)

The platinum(II) complexes of formula(1) may be prepared by employing various methods; and among them, more preferred ones are described below.

The following Methods A and B may be employed for preparing the compounds of formula(1) wherein two Xs jointly form the group of formula(a), i.e., the compounds represented by the formula of:

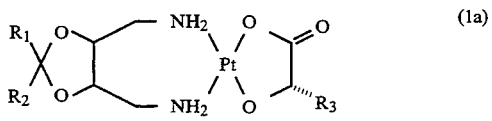
(1a)

wherein $R_1$, $R_2$, $R_3$ and the absolute configurations are the same as defined previously.

Method A

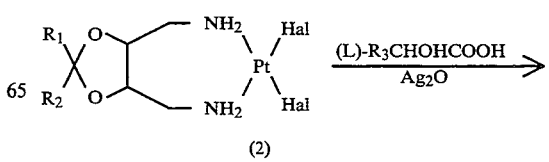
(2)

-continued
Method A

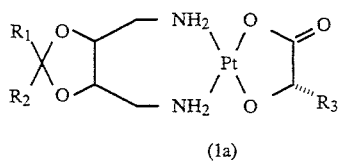

(1a)

wherein $R_1$, $R_2$, $R_3$ and the absolute configurations are the same as defined previously, and Hal is a halogen atom.

In Method A, a dihalogenodiamine platinum(II) complex of formula(2) is reacted with a compound represented by the formula of (L)-$R_3$CHOHCOOH wherein $R_3$ is H or $CH_3$, i.e., glycolic acid ($R_3$=H) or L-lactic acid($R_3$=$CH_3$), and silver(I) oxide, in the equivalent ratio of from 1:0.5:0.5 to 1:5:5, to obtain the desired compound of formula(1a). The reaction may be advantageously carried out in an aqueous medium or a mixed medium of an aqueous solvent and an alcoholic solvent such as methanol and ethanol in a dark environment at a temperature between 0° C. and 100° C., preferably between 50° C. and 70° C., for about 1 hour to 3 days.

Method B

Step 1:

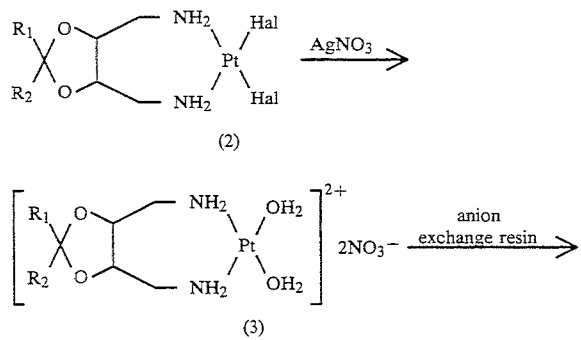

Step 2:

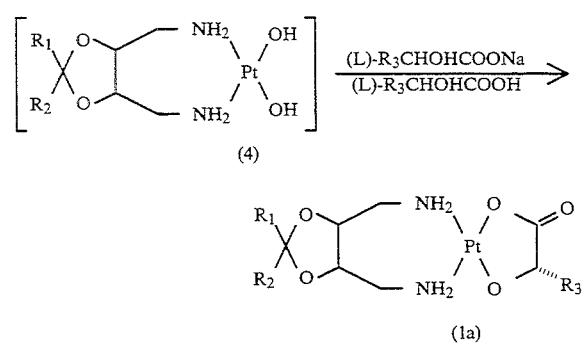

wherein $R_1$, $R_2$, $R_3$, the absolute configurations and Hal are the same as defined previously.

In Step 1 of Method B, a dihalogenodiamine platinum(II) complex of formula(2) is reacted with an aqueous silver nitrate solution, preferably in the molar ration of about 1:2, to obtain an aqueous solution of a diaquacomplex represented by formula(3), which is then converted to an aqueous solution of a compound represented by formula(4) through an anion-exchange resin. The reaction of the compound(2) with silver nitrate may be advantageously carried out in an aqueous medium in a dark environment at a temperature between 0° C. and 80° C. for about 20 minutes to 3 days. The anion-exchange resin used for converting the compound(3) to the compound(4) is generally an OH-type resin such as Amberlite IRA-400, Dowex I or Daiaion SA-10A.

Thereafter, in Step 2, the aqueous solution of the compound(4) obtained above is reacted with an acid and its salt represented by the formula of (L)-$R_3$CHOHCOOH and (L)-$R_3$CHOHCOONa wherein $R_3$ is H or $CH_3$, i.e., glycolic acid and sodium glycolate ($R_3$=H) or L-lactic acid and sodium L-lacate($R_3$=$CH_3$), preferably in the molar ration of 1:1:1 to 1:5:5, to obtain the desired compound of formula(1a). The reaction may be advantageously carried out in an aqueous medium in a dark environment at a temperature between 0° C. and 100° C., preferably 50° C. and 70° C., for about 1 hour to 3 days.

The following Methods C and D may be employed for preparing the compounds of formula(1) wherein two Xs jointly from the group of formula(b)m i.e., the compounds represented by the formula of:

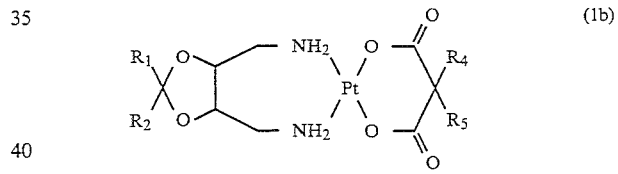

(1b)

wherein $R_1$, $R_2$, $R_4$, $R_5$ and the absolute configurations are the same as defined previously.

Method C

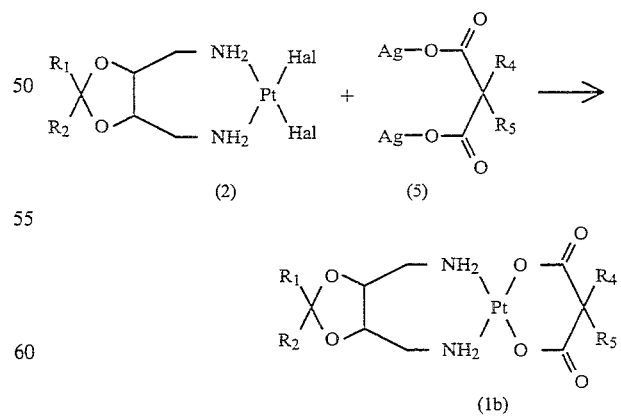

(1b)

wherein $R_1$, $R_2$, $R_4$, $R_5$, the absolute configurations and Hal are the same as defined previously.

In Method C, a dihalogenodiamine platinum(II) complex of formula(2) is reacted with a silver salt of formula(5), preferably in the molar ratio of from 1:0.5 to 1:5, to obtain the desired compound of formula(1b). The reaction is advantageously carried out in an aqueous medium in a dark environment at a temperature between 0° C. and 100° C., preferably between 50° C. and 70° C., for about 1 hour to 3 days.

Method D

Step 1:

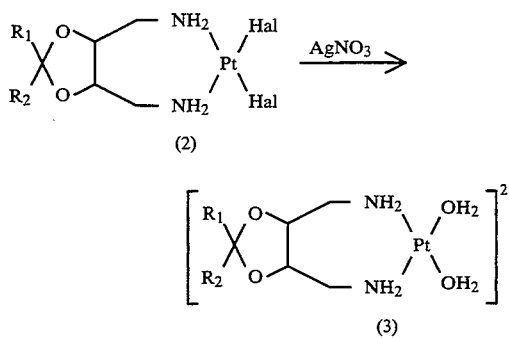

(2)

(3)

Step 2:

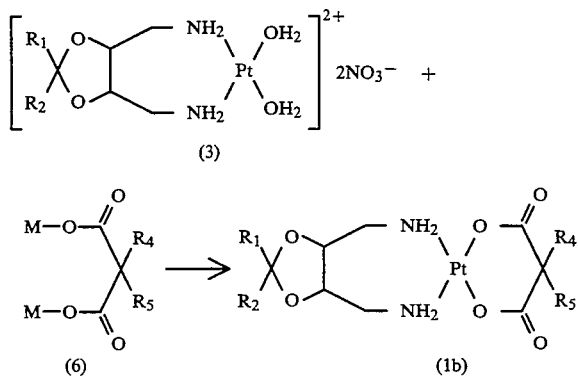

(3)

(6)            (1b)

wherein $R_1$, $R_2$, $R_4$, $R_5$, the absolute configurations and Hal are the same as defined previously, and M is a monovalent cation such as Na, K and the like.

In Step 1 of Method D, a dihalogenodiamine platinum(II) complex is reacted with a silver ion, for example, with 2 moles of silver nitrate per 1 mole of compound(2) or with 1 mole of silver sulfate per 1 mole of compound(2), to obtain an aqueous solution of a diaquacomplex represented by formula(3). The reaction is advantageously carried out in an aqueous medium at a temperature between 0° C. and 80° C. for about 1 hour to 3 days.

Thereafter, in Step 2, the aqueous solution of a diaquacomplex(3) obtained above is reacted with a compound of formula(6) to obtain the desired compound of formula(1b). The reaction is advantageously carried out in an aqueous medium at a temperature between 0° C. and 100° C. for about 1 hour to 3 days.

In the above described Methods A to D, in order to obtain a compound of formula(1) having the (4R, 5R) absolute configurations at the chiral centers in the 4,5-bis(aminomethyl)-1,3-dioxolane, the dihalogenodiamine platinum(II) complex of formula(2) having the corresponding (4R, 5R) configurations should be employed as a starting material. Similarly, in order to obtain a compound of formula(1) having the (4S, 5S) absolute configurations at the chiral centers, a dihalogenodiamine platinum(II) complex of formula (2) with the corresponding absolute configurations should be employed as a starting material.

The dihalogenodiamine platinum(II) complexes of formula (2) employed as starting materials in Methods A to D may be prepared as follows:

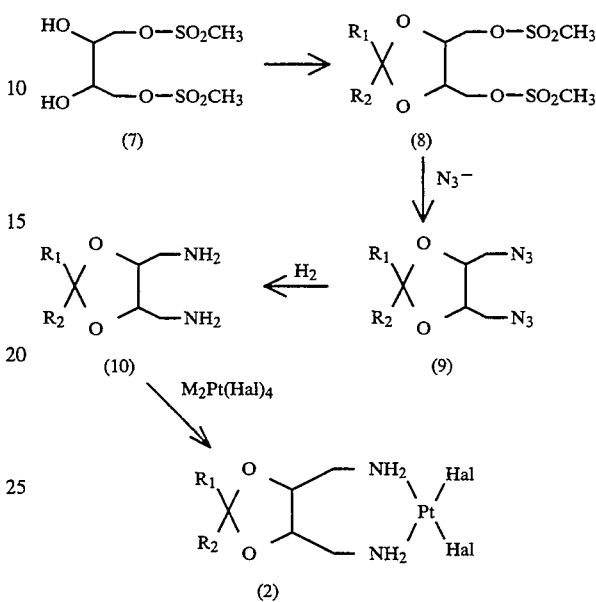

wherein $R_1$, $R_2$, the absolute configurations, Hal and M are the same as defined previously.

As illustrated above, first, a readily prepared compound of formula(7) in accordance with the method described in J. Med. Chem., 7, 14(1964), i.e., threitol 1,4-bis(methanesulfonate), is reacted with an appropriate aldehyde, acetal, ketone or ketal, preferably in the presence of an acid catalyst such as methanesulfonic acid, concentrated sulfuric acid and the like, to obtain a 1,3-dioxolane-4,5-bis(methanesulfonate) of formula(8). The selection of said aldehyde, acetal, ketone or ketal is made according to the substituents $R_1$ and $R_2$. For examples, formaldehyde may be chosen when both $R_1$ and $R_2$ are hydrogens; acetaldehyde diethyl acetal when either $R_1$ and $R_2$ is a methyl group and the other is a hydrogen atom; propionaldehyde diethyl acetal when either $R_1$ or $R_2$ is a ethyl group and the other is a hydrogen atom; isobutylaldehyde when one of $R_1$ and $R_2$ is a isopropyl group and the other is a hydrogen atom; cyclopentanone when $R_1$ and $R_2$ jointly form cyclopentane together with the carbon atom attached thereto; or cyclohexanone when $R_1$ and $R_2$ jointly form cyclohexane together with the carbon atom attached thereto.

The compound of formula(8) thus obtained is reacted with an azide ion in N,N-dimethylformamide at a temperature between 20° C. and 120° C. for about 1 to 24 hours to obtain a 4,5-bis(azidomethyl)-1,3-dioxolane of formula(9).

Thereafter, said 4,5-bis(azidomethyl)-1,3-dioxolane of formula(9) is subjected to a reduction process to yield a 4,5-bis(aminomethyl)-1,3-dioxolane of formula(10) by using a conventional method such as reduction with hydrogen in the presence of palladium-charcoal or platinum(IV) oxide in an alcoholic medium under a pressure between 15 psi and 70 psi at a temperature between 0° C. and 50° C. for about 30 minutes to 1 day.

Finally, the compound of formula(10) is reacted with an equimolar amount of tetrahalogenoplatinate(II) salt represented by the formula of $M_2Pt(Hal)_4$ wherein M and Hal have the same meanings as defined previously, generally in an aqueous medium at a temperature between 0° C. and 100° C., preferably between 50° C. and 70° C. at an atmospheric pressure but preferably under a stream of an inert gas such as nitrogen or argon gas, to obtain the dihalogenodiamine platinum(II) complex of formula(2).

The compound of formula(8) may be prepared by using an alternative method, which comprises the following steps:

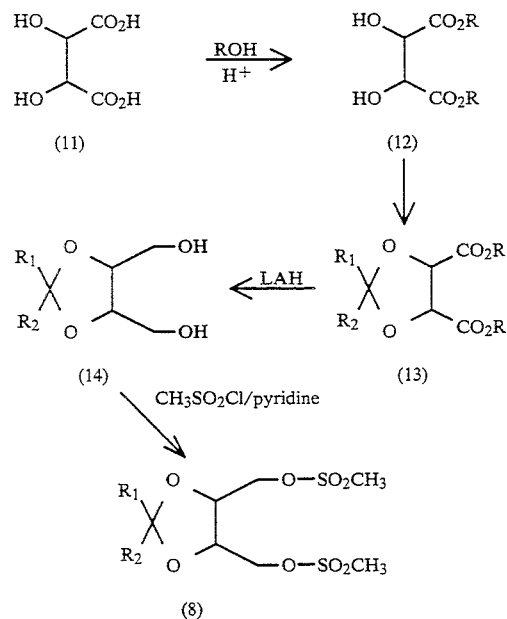

wherein $R_1$, $R_2$, and the absolute configurations, are the same as defined previously, and R is a methyl or ethyl group.

In accordance with the above method, tartaric acid of formula(11) is reacted with methanol or ethanol in the presence an acid catalyst to obtain a tartaric acid diester of formula(12). The compound of formula(12) is reacted with an appropriate aldehyde, acetal, ketone or ketal, preferably in the presence of an acid catalyst such as methanesulfonic acid, concentrated sulfuric acid and the like, or phosphorus pentoxide(Tsuzuki, et al., Bull, Chem. Sco. Japan 15, 55(1940)), to obtain a 1,3-dioxolane-4,5-dicarboxylic acid diester of formula(13). Said appropriate aldehyde, acetal, ketone or ketal can be chosen according to the substituents $R_1$ and $R_2$, as previously illustrated. The compound of formula(13) is then reduced with lithium aluminum hydride(LAH) to obtain a 4,5-bis(hydroxymethyl)-1,3-dioxolane of formula(14). The compound of formula(14) is reacted with methanesulfonyl chloride in pyridine to obtain the 1,3-dioxolane-4,5-bis(methanesulfonate) of formula(8).

The compounds of formula(8), (9), (10) and (2) having the (4R, 5R) absolute configurations at the respective chiral centers in said 4,5-bis(aminomethyl)-1,3-dioxolane are obtainable from the starting compound of formula(7) or (11) existing as D-form, i.e., D-threitol 1,4-bis(methanesulfonate) or D-tartaric acid. Whereas the compound of formula(7) or (11) existing as L-form, i.e., L-threitol 1,4-bis(methanesulfonate) or L-tartaric acid yields the compounds of formula(8), (9), (10) and (2) having the (4S, 5S) configurations.

The intermediate compounds of formulas, (9), (10) and (2) obtained from the procedure described above are novel compounds excepting: as for the compounds of formula(9) wherein $R_1$ and $R_2$ are both methyl; and as for the compounds of formula(10) wherein $R_1$ and $R_2$ are both methyl.

The platinum(II) complexes of the present invention have improved pharmacological characteristics such as excellent anti-tumor activities, low nephrotoxicity and good solubility in water and the like; and, therefore, are useful as an anti-cancer agent.

The compounds of the present invention can be formulated by any of the known appropriate methods with a pharmaceutically acceptable carrier and, if necessary, an adjuvant. For oral administration, for instance, the compounds of the present invention can be formulated into a solid preparation such as tablets, pills, granules, powder, capsules and the like, or a liquid preparation such as solution, suspension, emulsion and the like. When the preparation is used for parenteral administration, the preparation is made in an injection formula, an intravenous drip infusion and the like. For the preparation of an injection formula, the compound is preferably dissolved in distilled water or an aqueous solution of a salt such as sodium chloride. For the preparation of an intravenous drip infusion, the compound may be dissolved in a suitable fluid therapy such as a physiological saline, a glucose-sodium chloride solution and the like.

The effective dosage of the compounds of the present invention may vary with the physical condition of the patients and the location and status of the tumors. In general, it has been shown advantageous to administer the active compounds in an amount of about 50 to 1000 mg per 1 $m^2$ body surface area in order to achieve the desired result.

The present invention is further illustrated in the following Examples, which should not be taken to limit the scope of the invention.

The structure of the compounds(II) of the present invention was confirmed by various analytical methods such as infrared(IR) spectrometry, $^1H$ NMR spectrometry, $^{13}C$ NMR spectrometry, elemental analysis, fast atom bombardment mass spectrometry(FAB-MS) and the like.

EXAMPLE 1A

Synthesis of (glycolato-O,O')[(4R,5R)-4,5-bis(aminomethyl)-1,3-dioxolane]platinum(II) by Method A A mixture of cis-diiodo[(4R,5R)-4,5-bis(aminomethyl)-1,3-dioxolane]platinum(II)(0.50 g, 0.86 mmol), glycolic acid(0.13 g, 1.71 mmol), and silver(I) oxide(0.40 g, 1.72 mmol) in water(30 ml) was stirred at 60° C. overnight in the dark. The reaction mixture was cooled to a room temperature, filtered through a pad of celite, and the filtered residue was washed with a small volume of water. The filtrate and the washing were combined and concentrated under a reduced pressure to 5 ml, and purified by using preparative HPLC on Delta pak C18-100 Å reverse-phase bonded silica cartridge with water as the mobile phase. The eluate was concentrated under a reduced pressure to a small volume and freeze-dried to give 0.198 g of (glycolato-O,O')[(4R,5R)-4,5-bis(aminomethyl)-1,3-dioxolane]-platinum(II) as a white solid.

Yield: 57% IR(KBr): 3445, 3222, 3069 $cm^{-1}$ (NH), 1645 $cm^{-1}$ (C=O) $^1H$ NMR($D_2O$/DSS): δ2.87(m, 2H, 2 CHNH$_2$), 3.38(m, 2H, 2 CHNH$_2$), 4.10(s, 2H, CH$_2$), 4.59(m, 2H, 2 CH), 5.05 (s, 2H, OCH$_2$O) DSS($\delta$=0.015 ppm in D$_2$O) was used as the internal standard $^{13}$C NMR(D$_2$O/DSS): $\delta$48.52, 48.82, 69.30, 79.49, 79.53, 95.42, 195.49 DSS($\delta$=−1.600 ppm in D$_2$O) was used as the internal standard FAB-MS: (M+H)$^+$=401($^{194}$Pt, 33%), 402($^{195}$Pt, 34%) and 403($^{196}$Pt, 25%)

EXAMPLE 1B

Synthesis of (glycolato-O,O')[(4R,5R)-4,5-bis(aminomethyl)-1,3-dioxolane]platinum(II) by Method B To a stirred suspension of cis-diiodo[(4R,5R)-4,5-bis-(aminomethyl)-1,3-dioxolane]platinum(II)(0.50 g, 0.86 mmol) in water(15 ml) was added a solution of silver nitrate(0.29 g, 1.72 mmol) in water(15 ml). The mixture was heated at 60° C. for 2 hours in the dark, cooled to a room temperature, filtered through a pad of celite, and the filtered residue was washed with a small volume of water. The filtrate and the washing were combined and concentrated under a reduced pressure to 10 ml and passed through a column of anion exchange resin Amberlite IRA-400(OH$^-$ type, 20 ml) with water as the eluent. To 30 ml of alkaline eluate were added glycolic acid(0.07 g, 0.92 mmol) and 1M aqueous solution of sodium glycolate(3.44 ml). The mixture was stirred at 60° C. overnight in the dark, cooled to a room temperature, and concentrated under a reduced pressure to 5 ml. The concentrate was purified in the same manner as described in Example 1A to give 0.194 g of (glycolato-O,O')[(4R,5R)-4,5-bis(aminomethyl)-1,3-dioxolane]platinum(II).

Yield: 56%

EXAMPLE 2A

Synthesis of (glycolato-O,O')[(4R,5R)-4,5-bis(aminomethyl)-2,2-dimethyl-1,3-dioxolane]platinum(II) by Method A 0.50 g(0.82 mmol) of cis-diiodo[(4R,5R)-4,5-bis-(aminomethyl)-2,2-dimethyl-1,3-dioxolane]platinum(II) was reacted with glycolic acid(0.13 g, 1.71 mmol) and silver(I) oxide(0.38 g, 1.64 mmol) in water(30 ml) in the same manner as described in Example 1A to give 0.149 g of (glycolato-O,O')[(4R,5R)-4,5-bis(aminomethyl)-2,2-dimethyl-1,3-dioxolane]platinum(II) as a white solid after purification by using preparative HPLC on Delta pak C18-100 Å reverse-phase bonded silica cartridge with a mixture of water-methanol(9:1, v/v) as the mobile phase.

Yield: 42% IR(KBr):3430, 3142, 3085 cm$^{-1}$ (NH), 1657 cm$^{-1}$ (C=O) $^1$H NMR(D$_2$O/DSS): $\delta$1.47(s, 6H, 2 CH$_3$), 2.86(m, 2H, 2 CHNH$_2$), 3.32(m, 2H, 2 CHNH$_2$), 4.10(s, 2H, CH$_2$), 4.71(m, 2H, 2 CH) DSS($\delta$=0.015 ppm in D$_2$O) was used as the internal standard $^{13}$C NMR(D$_2$O/DSS): $\delta$26.56, 49.36, 49.65, 69.27, 79.18, 111.35, 195.51 DSS($\delta$=−1.600 ppm in D$_2$O) was used as the internal standard FAB-MS: (M+H)$^+$=429($^{194}$Pt, 33%), 430($^{195}$Pt, 34%) and 431($^{196}$Pt, 25%)

EXAMPLE 2B

Synthesis of (glycolato-O,O')[(4R,5R)-4,5-bis(aminomethyl)-2,2-dimethyl-1,3-dioxolane]platinum(II) by Method B 0.50 g(0.82 mmol) of cis-diiodo[(4R,5R)-4,5-bis-(aminomethyl)-2,2-dimethyl-1,3-dioxolane]platinum(II) was reacted with silver nitrate(0.28 g, 1.65 mmol), followed by passing the reaction mixture through a column of anion exchange resin Amberlite IRA-400, and then reacted with glycolic acid(0.06 g, 0.79 mmol) and sodium glycolate (3.3 ml of 1M aqueous solution) in the same manner as described in Example 1B to give 0.161 g of (glycolato-O,O')[(4R,5R)-4,5-bis(aminomethyl)-2,2-dimethyl-1,3-dioxolane]platinum(II) as a white solid after purification in the same manner as described in Example 2A.

Yield: 46%

Example 3A

Synthesis of (glycolato-O,O')[4R,5R)-4,5-bis(aminomethyl)-1,3-dioxolane-2-spiro-1'-cyclopentane]platinum (II) by method A 0.50 g(0.79 mmol) of cis-diiodo[(4R,5R)-4,5-bis-(aminomethyl)-1,3-dioxolane-2-spiro-1'-cyclopentane]-platinum(II) was reacted with glycolic acid(0.12 g, 1.58 mmol) and silver(I) oxide (0.37 g, 1.60 mmol) in a mixture of water(55 ml) and methanol(5 ml) in the same manner as described in Example 1A to give 0.243 g of (glycolato-O,O')[(4R,5R)-4,5-bis(aminomethyl)-1,3-dioxolane-2-spiro-1'-cyclopentane]platinum(II) as a white solid after purification by using preparative HPLC on Delta pak C18-100 Å reverse-phase bonded silica cartridge with a mixture of water-methanol(6:4, v/v) as the mobile phase.

Yield: 68% IR(KBr): 3409, 3211, 3143 cm$^{-1}$ (NH), 1635 cm$^{-1}$ (C=O) $^1$H NMR(D$_2$O/DSS): $\delta$1.60–2.00(m, 8H, cyclopentyl), 2.86 (m, 2H, 2 CHNH$_2$), 3.33(m, 2H, 2 CHNH$_2$), 4.10(s, 2H, CH$_2$), 4.66(m, 2H, 2 CH) DSS($\delta$=0.015 ppm in D$_2$O) was used as the internal standard $^{13}$C NMR(D$_2$O/DSS): $\delta$23.88, 37.11, 49.22, 49.50, 69.29, 79.05, 121.09, 195.51 DSS($\delta$=−1.600 ppm in D$_2$O) was used as the internal standard FAB-MS: (M+H)$^+$=455($^{194}$Pt, 33%), 456($^{195}$Pt, 34%) and 457($^{196}$Pt, 25%)

Example 3B

Synthesis of (glycolato-O,O')[(4R,5R)-4,5-bis(aminomethyl)-1,3-dioxolane-2-spiro-1'-cyclopentane]platinum (II) by Method B 0.50 g(0.79 mmol) of cis-diiodo[(4R,5R)-4,5-bis-(aminomethyl)-1,3-dioxolane-2-spiro-1'-cyclopentane]-platinum(II) was reacted with silver nitrate(0.27 g, 1.59 mmol), followed by passing the reaction mixture through a column of anion exchange resin Amberlite IRA-400, and then reacted with glycolic acid (0.06 g, 0.79 mmol) and sodium glycolate(3.2 ml of 1M aqueous solution) in the same manner as described in Example 1B to give 0.178 g of (glycolato-O,O')[4R,5R)-4,5-bis-(aminomethyl)-1,3-dioxolane-2-spiro-1'-cyclopentane]-platinum(II) as a white solid after purification in the same manner as described in Example 3A.

Yield: 50%

Example 4A

Synthesis of (glycolato-O,O'){cyclohexanespiro-2'-[(4'R,5'R)-4',5'-bis(aminomethyl)-1',3'-dioxolane]}-platinum(II) by Method A 0.50 g(0.77 mmol) of cis-diiodo{cyclohexanespiro-2'-[(4'R,5'R)-4',5'-bis(aminomethyl)-1',3'-dioxolane]} platinum(II) was reacted with glycolic acid(0.12 g, 1.58 mmol) and silver(I) oxide(0.36 g, 1.55 mmol) in a mixture of water(110 ml) and methanol (10 ml) in the same manner as described in Example 1A to give 0.174 g of (glycolato-O,O'){cyclohexanespiro-2'-[(4'R,5'R)-4',5'-bis(aminomethyl)-1',3'-dioxolane]}platinum(II) as a white solid after purification by using preparative HPLC on Delta pak C18-100 Å reverse-phase bonded silica cartridge with a mixture of water-methanol(6:4, v/v) as the mobile phase.

Yield: 48% IR(KBr): 3417, 3218, 3143 $cm^{-1}$ (NH), 1634 $cm^{-1}$ (C=O) $^1$H NMR(DMSO-d$_6$/TMS): δ1.34(br s, 2H, cyclohexyl), 1.54 (br s, 8H, cyclohexyl), 2.55(m, 2H, 2 CHNH$_2$), 3.14(m, 2H, 2 CHNH$_2$), 3.78 (s, 2H, CH$_2$), 4.40(m, 2H, 2 CH), 4.93 (br s, 1H, NH), 5.15(br s, 2H, 2 NH), 5.24(br s, 1H, NH) $^{13}$C NMR(DMSO-d$_6$): δ23.79, 24.83, 35.96, 36.00, 48.92, 48.96, 69.70, 78.17, 78.21, 109.43, 191.91 FAB-MS: (M+H)$^+$=469($^{194}$Pt, 33%), 470($^{195}$Pt, 34%) and 471($^{196}$Pt, 25%)

Example 4B

Synthesis of (glycolato-O,O'){cyclohexanespiro-2'-[(4'R,5'R)-4',5'-bis(aminomethyl)-1',3'-dioxolane]}-platinum(II) by Method B 0.50 g(0.77 mmol) of cis-diiodo{cyclohexanespiro-2'-[(4'R,5'R)-4',5'-bis(aminomethyl)-1',3'-dioxolane]}platinum(II) was reacted with silver nitrate(0.26 g, 1.53 mmol), followed by passing the reaction mixture through a column of anion exchange resin Amberlite IRA-400, and then reacted with glycolic acid (0.06 g, 0.79 mmol) and sodium gylcolate(3.1 ml of 1M aqueous solution) in the same manner as described in Example 1B to give 0.084 g of (glycolato-O,O'){cyclohexanespiro-2'-[(4'R,5'R)-4',5'-bis(aminomethyl)-1',3'-dioxolane]}platinum(II) as a white solid after purificiation in the same manner as described in Example 4A.

Yield: 23%

Example 5A

Synthesis of (glycolato-O,O')[4R,5R)-4,5-bis(aminomethyl)-2-methyl-1,3-dioxolane]platinum(II) by Method A 0.50 g(0.84 mmol) of cis-diiodo[(4R,5R)-4,5-bis-(aminomethyl)-2-methyl-1,3-dioxolane]platinum(II) was reacted with glycolic acid(0.13 g, 0.17 mmol) and silver(I) oxide(0.39 g, 1.68 mmol) in water(30 ml) in the same manner as described in Example 1A to give 0.225 g of (glycolato-O,O')[(4R,5R)-4,5-bis(aminomethyl)-2-methyl-1,3-dioxolane]platinum(II) as a white solid after purification by using preparative HPLC on Delta pak C18-100 Å reverse-phase bonded silica cartridge with a mixture of water-methanol(95:5, v/v) as the mobile phase.

Yield: 64% IR(KBr): 3451, 3213, 3139 $cm^{-1}$ (NH), 1634 $cm^{-1}$ (C=O) $^1$H NMR(D$_2$O/DSS): δ1.40(d, J=4.8 Hz, 3H, CH$_3$), 2.87 (m, 2H, 2 CHNH$_2$), 3.28(m, 1H, CHNH$_2$), 3.39(m, 1H, CHNH$_2$), 4.10(s, 2H, CH$_2$) 4.64(m, 1H, CH), 4.71(m, 1H, CH, overlapped with HOD), 5.28(q, J=4.8 Hz, 1H, CH) DSS(δ=0.015 ppm in D$_2$O) was used as the internal standard $^{13}$C NMR(D$_2$O/DSS): δ19.51, 48.57, 48.73, 48.86, 49.05, 69.29, 78.82, 80.77, 102.70, 195.46 DSS(δ=−1.600 ppm in D$_2$O) was used as the internal standard FAB-MS: (M+H)$^+$=415($^{194}$Pt, 33%), 416($^{195}$Pt, 34%) and 417($^{196}$Pt, 25%)

Example 5B

Synthesis of (glycolato-O,O')[(4R,5R)-4,5-bis(aminomethyl)-2-methyl-1,3-dioxolane]platinum(II) by Method B 0.50 g(0.84 mmol) of cis-diiodo[(4R,5R)-4,5-bis-(aminomethyl)-2-methyl-1,3-dioxolane]platinum(II) was reacted with silver nitrate(0.28 g, 1.65 mmol), followed by passing the reaction mixture through a column of anion exchange resin Amberlite IRA-400, and then reacted with glycolic acid(0.06 g, 0.79 mmol) and sodium glycolate(3.4 ml of 1M aqueous solution) in the same manner as described in Example 1B to give 0.273 g of (glycolato-O,O')[(4R,5R)-4,5-bis(aminomethyl)-2-methyl-1,3-dioxolane]platinum(II) as a white solid after purification in the same manner as described in Example 5A.

Yield: 78%

Example 6A

Synthesis of (glycolato-O,O')[(4R,5R)-4,5-bis(aminomethyl)-2-ethyl-1,3-dioxolane]platinum(II) by Method A 0.50 g(0.82 mmol) of cis-diiodo[(4R,5R)-4,5-bis-(aminomethyl)-2-ethyl-1,3-dioxolane]platinum(II) was reacted with glycolic acid(0.13 g, 1.71 mmol) and silver(I) oxide(0.38 g, 1.64 mmol) in water(30 ml) in the same manner as described in Example 1A to give 0.234 g of (glycolate-O,O')[(4R,5R)-4,5-bis(aminomethyl)-2-ethyl-1,3-dioxolane]platinum(II) as a white solid after purification by using preparative HPLC on Delta pack C18-100 Å reverse-phase bonded silica cartridge with a mixture of water-methanol(9:1, v/v) as the mobile phase.

Yield: 66% IR(KBr): 3431, 3132 $cm^{-1}$ (NH), 1650 $cm^{-1}$ (C=O) $^1$H NMR(D$_2$O/DSS): δ0.93(t, J=7.5 Hz, 3H, CH$_3$), 1.72 (dq, J=4.5 Hz, J=7.5 Hz, 2H, CH$_2$CH$_3$), 2.88(m, 2H, 2 CHNH$_2$), 3.29(m, 1H, CHNH$_2$), 3.39(m, 1H, CHNH$_2$), 4.10(s, 2H, CH$_2$), 4.61(m, 1H, CH), 4.68(m, 1H, CH, overlapped with HOD), 5.15(t, J=4.5 Hz, 1H, CH) DSS(δ=0.015 ppm in D$_2$O) was used as the internal standard $^{13}$C NMR(D$_2$O/DSS): δ7.89, 26.90, 48.65, 48.70, 48.94, 49.00, 69.28, 78.85, 80.57, 106.43, 195.48 DSS(δ=−1.600 ppm in D$_2$O) was used as the internal standard FAB-MS: (M+H)$^+$=429($^{194}$Pt, 33%), 430($^{195}$Pt, 34%) and 431($^{196}$Pt, 25%)

Example 6B

Synthesis of (glycolato-O,O')[(4R,5R)-4,5-bis(aminomethyl)-2-ethyl-1,3-dioxolane]platinum(II) by Method B 0.50 g(0.82 mmol) of cis-diiodo[(4R,5R)-4,5-bis-(aminomethyl)-2-ethyl-1,3-dioxolane]platinum(II) was reacted with silver nitrate(0.28 g, 1.65 mmol), followed by passing the reaction mixture through a column of anion exchange resin Amberlite IRA-400, and then reacted with glycolic acid(0.06 g, 0.79 mmol) and sodium glycolate(3.3 ml of 1M aqueous solution) in the same manner as described in Example 1B to give 0.189 g of (glycolato-O,O')[(4R,5R)-4,5-bis(aminomethyl)-2-ethyl-1,3-dioxolane]platinum(II) as a white solid after purification in the same manner as described in Example 6A.

Yield: 54%

Example 7A

Synthesis of (glycolato-O,O')[(4R,5R)-4,5-bis(aminomethyl)-2-isopropyl-1,3-dioxolane]platinum(II) by Method A 0.50 g(0.80 mmol) of cis-diiodo[(4R,5R)-4,5-bis-(aminomethyl)-2-isopropyl-1,3-dioxolane]platinum(II) was reacted with gylcolic acid(0.12 g, 1.58 mmol) and silver(I) oxide(0.37 g, 1.60 mmol) in a mixture of water(55 ml) and methanol(5 ml) in the same manner as described in Example 1A to give 0.267 g of (glycolato-O,O')[(4R,5R)-4,5-bis(aminomethyl)-2-isopropyl-1,3-dioxolane]platinum(II) as a white solid after purification by using preparative HPLC on Delta pak C18-100 Å reverse-phase bonded silica cartridge with a mixture of water-methanol(7:3, v/v) as the mobile phase.

Yield: 75% IR(KBr): 3425, 3218, 3143 $cm^{-1}$ (NH), 1634 $cm^{-1}$ (C=O) $^1H$ NMR($D_2O$/DSS): δ0.94(d, J=6.9 Hz, 6H, 2 $CH_3$), 1.89 (m, 1H, $CH(CH_3)_2$), 2.86(m, 2H, 2 $CHNH_2$), 3.30(m, 1H, $CHNH_2$), 3.39(m, 1H, $CHNH_2$), 4.10(s, 2H, $CH_2$), 4.58(m, 1H, CH), 4.64 (m, 1H, CH, overlapped with HOD), 4.98(d, J=4.2 Hz, 1H, CH) DSS(δ=0.015 ppm in $D_2O$) was used as the internal standard $^{13}C$ NMR($D_2O$/DSS): δ16.69, 16.79, 32.02, 48.66, 48.72, 48.96, 49.02, 69.28, 78.97, 80.48, 109.26, 195.50 DSS(δ=−1.600 ppm in $D_2O$) was used as the internal standard FAB-MS: $(M+H)^+$=443($^{194}Pt$, 33%), 444($^{195}Pt$, 34%) and 445($^{196}Pt$, 25%)

Example 7B

Synthesis of (glycolato-O,O')[(4R,5R)-4,5-bis(aminomethyl)-2-isopropyl-1,3-dioxolane]platinum(II) by Method B 0.50 g(0.80 mmol) of cis-diiodo[(4R,5R)-4,5-bis-(aminomethyl)-2-isopropyl-1,3-dioxolane]platinum(II) was reacted with silver nitrate(0.27 g, 1.59 mmol), followed by passing the reaction mixture through a column of anion exchange resin Amberlite IRA-400, and then reacted with glycolic acid(0.06 g, 0.79 mmol) and sodium glycolate(3.2 ml of 1M aqueous solution) in the same manner as described in Example 1B to give 0.102 g of (glycolato-O,O')[(4R,5R)-4,5-bis(aminomethyl)-2-isopropyl-1,3-dioxolane]platinum(II) as a white solid after purification in the same manner as described in Example 7A.

Yield: 29%

Example 8

Synthesis of (glycolato-O,O')[(4R,5R)-4,5-bis(aminomethyl)-2,2-diethyl-1,3-dioxolane]platinum(II) by Method A 1.42 g(2.23 mmol) of cis-diiodo[(4R,5R)-4,5-bis-(aminomethyl)-2,2-diethyl-1,3-dioxolane]platinum(II) was reacted with glycolic acid(0.34 g, 4.46 mmol) and silver(I) oxide(1.03 g, 4.46 mmol) in a mixture of water(100 ml) and methanol(10 ml) in the same manner as described in Example 1A to give 0.616 g of (glycolato-O,O')[(4R,5R)-4,5-bis(aminomethyl)-2,2-diethyl-1,3-dioxolane]platinum(II) as a white solid after purification by using preparative HPLC on Delta pak C18-100 Å reverse-phase bonded silica cartridgl with a mixture of water-methanol(6:4, v/v) as the mobile phase.

Yield: 60% IR(KBr): 3422, 3208 $cm^{-1}$ (NH), 1640 $cm^{-1}$ (C=O) $^1H$ NMR($D_2O$/DSS): δ0.91(t, J=7.2 Hz, 6H, 2 $CH_3$), 1.73 (q, J=7.2 Hz, 4H, 2 $CH_2$), 2.80–2.96 (m, 2H, 2 $CHNH_2$), 3.29–3.42(m, 2H, 2 $CHNH_2$), 4.10(s, 2H, $CH_2$), 4.71(m, 2H, 2 CH, overlapped with HOD) DSS(δ=0.015 ppm in $D_2O$) was used as the internal standard FAB-MS: $(M+H)^+$=457($^{194}Pt$, 33%), 458($^{195}Pt$, 34%) and 459($^{196}Pt$, 25%)

Example 9

Synthesis of (glycolato-O,O')[(4R,5R)-4,5-bis(aminomethyl)-2-ethyl-2-methyl-1,3-dioxolane]platinum(II) by Method A 1.22 g(1.96 mmol) of cis-diiodo[(4R,5R)-4,5-bis-(aminomethyl)-2-ethyl-2-methyl-1,3-dioxolane]-platinum(II) was reacted with glycolic acid(0.30 g, 3.92 mmol) and silver(I) oxide(0.91 g, 3.92 mmol) in a mixture of water(90 ml) and methanol(10 ml) in the same manner as described in Example 1A to give 0.607 g of (glycolato-O,O')[(4R,5R)-4,5-bis(aminomethyl)-2-ethyl-2-methyl-1,3-dioxolane]platinum(II) as a white solid after purification by using preparative HPLC on Delta pak C18-100 Å reverse-phase bonded silica cartridge with a mixture of water-methanol(6:4, v/v) as the mobile phase.

Yield: 70% IR(KBr): 3425, 3142 $cm^{-1}$ (NH), 1645 $cm^{-1}$ (C=O) $^1H$ NMR($D_2O$/DSS): δ0.92(t, J=6.6 Hz, 3H, $CH_3$), 1.43(s, 3H, $CH_3$), 1.75(q, J=6.6 Hz, 2H, $CH_2$), 2.78–2.98(m, 2H, 2 $CHNH_2$), 3.28–3.42(m, 2H, 2 $CHNH_2$), 4.10(s, 2H, $CH_2$), 4.72 (m, 2H, 2 CH, overlapped with HOD) DSS(δ=0.015 ppm in $D_2O$) was used as the internal standard $^{13}C$ NMR($D_2O$/DSS): δ8.25, 24.66, 32.69, 49.42, 49.52, 69.27, 79.04, 79.64, 113.44, 195.44 DSS(δ=−1.600 ppm in $D_2O$) was used as the internal standard FAB-MS: $(M+H)^+$=443($^{194}Pt$, 33%), 444($^{195}Pt$, 34%) and 445($^{196}Pt$, 25%)

Example 10

Synthesis of (glycolato-O,O')[(4R,5R)-4,5-bis(aminomethyl)-2-propyl-1,3-dioxolane]platinum(II) by Method A 1.00 g(1.91 mmol) of cis-diiodo[(4R,5R)-4,5-bis-(aminomethyl)-2-propyl-1,3-dioxolane]platinum(II) was reacted with glycolic acid(0.29 g, 3.82 mmol) and silver(I) oxide(0.89 g, 3.82 mmol) in a mixture of water(90 ml) and methanol(10 ml) in the same manner as described in Example 1A to give 0.470 g of (glycolato-O,O')[(4R,5R)-4,5-bis(aminomethyl)-2-propyl-1,3-dioxolane] platinum(II) as a white solid after purification by using preparative HPLC on Delta pak C18-100 Å reverse-phase bonded silica cartridge with a mixture of water-methanol(5:5, v/v) as the mobile phase.

Yield: 56% IR(KBr): 3422, 3210, 3131 $cm^{-1}$ (NH), 1630 $cm^{-1}$ (C=O) $^1H$ NMR($D_2O$/DSS): δ0.94(t, J=7.2 Hz, 3H, $CH_3$), 1.41(m, 2H, $CH_2$), 1.68(m, 2H, $CH_2$), 2.81–2.97 (m, 2H, 2 $CHNH_2$), 3.23–3.34(m, 1H, $CHNH_2$), 3.34–3.45(m, 1H, $CHNH_2$), 4.10(s, 2H, $CH_2$), 4.62(m, 2H, 2 CH, overlapped with HOD), 5.19(t, J=4.2 Hz, 1H, CH) DSS(δ=0.015 ppm in $D_2O$) was used as the internal standard FAB-MS: $(M+H)^+$=443($^{194}Pt$, 33%), 444($^{195}Pt$, 34%) and 445($^{196}Pt$, 25%)

Example 11

Synthesis of (glycolato-O,O')[(4R,5R)-4,5-bis(aminomethyl)-2-isobutyl-1,3-dioxolane]platinum(II) by Method A 1.00 g(1.86 mmol) of cis-diiodo[(4R,5R)-4,5-bis-(aminomethyl)-2-isobutyl-1,3-dioxolane]platinum(II) was reacted with glycolic acid(0.28 g, 3.72 mmol) and silver(I) oxide(0.86 g, 3.72 mmol) in a mixture of water (90 ml) and methanol(10 ml) in the same manner as described in Example 1A to give 0.257 g of (glycolato-O,O')[(4R,5R)-4,5-bis(aminomethyl)-2-isobutyl-1,3-dioxolane]platinum(II) as a white solid after purification by using preparative HPLC on Delta pak C18-100 Å reverse-phase bonded silica cartridge with a mixture of water-methanol(5:5, v/v) as the mobile phase.

Yield: 30% IR(KBr): 3430, 3140, 3082 cm$^{-1}$ (NH), 1653 cm$^{-1}$ (C=O) FAB-MS: (M+H)$^+$=457($^{194}$Pt, 33%), 458($^{195}$Pt, 34%) and 459($^{196}$Pt, 25%)

Example 12

Synthesis of (glycolato-O,O')[(4R,5R)-4,5-bis(aminomethyl)-2-tert-butyl-1,3-dioxolane]platinum(II) by Method A 0.97 g(1.80 mmol) of cis-diiodo[(4R,5R)-4,5-bis-(aminomethyl)-2-tert-butyl-1,3-dioxolane]platinum(II) was reacted with glycolic acid(0.27 g, 3.60 mmol) and silver(I) oxide(0.83 g, 3.60 mmol) in a mixture of water (90 ml) and methanol(10 ml) in the same manner as described in Example 1A to give 0.402 g of (glycolato-O,O')[(4R,5R)-4,5-bis(aminomethyl)-2-tert-butyl-1,3-dioxolane]platinum(II) as a white solid after purification by using preparative HPLC on Delta pak C18-100 Å reverse-phase bonded silica cartridge with a mixture of water-methanol(5:5, v/v) as the mobile phase.

Yield: 49% IR(KBr): 3486, 3190, 3063 cm$^{-1}$ (NH), 1645 cm$^{-1}$ (C=O) FAB-MS: (M+H)$^+$=457($^{194}$Pt, 33%), 458($^{195}$Pt, 34%) and 459($^{196}$Pt, 25%)

Example 13A

Synthesis of (L-lactato-O,O')[(4R,5R)-4,5-bis(aminomethyl)-1,3-dioxolane]platinum(II) by Method A 0.50 g(0.86 mmol) of cis-diiodo[(4R,5R)-4,5-bis-(aminomethyl)-1,3-dioxolane]platinum(II) was reacted with L-lactic acid (0.18 g of 85% solution in water, 1.72 mmol) and silver(I) oxide (0.40 g, 1.72 mmol) in water(30 ml) in the same manner as described in Example 1A to give 0.206 g of(L-lactato-O,O')[(4R,5R)-4,5-bis-(aminomethyl)-1,3-dioxolane]platinum(II) as a white solid after purification by using preparative HPLC on Delta pak C18-100 Å reverse-phase bonded silica cartridge with a mixture of water-methanol(93:7, v/v) as the mobile phase.

Yield: 58% IR(KBr): 3426, 3209, 3132 cm$^{-1}$ (NH), 1628 cm$^{-1}$ (C=O) $^1$H NMR(D$_2$O/DSS): δ1.30(d, J=6.9 Hz, 3H, CH$_3$), 2.89 (m, 2H, 2 CHNH$_2$), 3.4(m, 2H, 2 CHNH$_2$), 4.17(q, J=6.9 Hz, 1H, CHCH$_3$), 4.60(m, 2H, 2 CH), 5.05(s, 2H, OCH$_2$O) DSS(δ=0.015 ppm in D$_2$O) was used as the internal standard $^{13}$C NMR(D$_2$O/DSS): δ22.62, 48.47, 48.82, 75.19, 79.53, 79.58, 95.43, 196.47 DSS(δ=−1.600 ppm in D$_2$O) was used as the internal standard FAB-MS: (M+H)$^+$=415($^{194}$Pt, 33%), 416($^{195}$Pt, 34%) and 417($^{196}$Pt, 25%)

Example 13B

Synthesis of (L-lactato-O,O')[(4R,5R)-4,5-bis(aminomethyl)-1,3-dioxolane]platinum(II) by Method B 0.50 g(0.86 mmol) of cis-diiodo[(4R,5R)-4,5-bis-(aminomethyl)-1,3-dioxolane]platinum(II) was reacted with silver nitrate (0.29 g, 1.72 mmol), followed by passing the reaction mixture through a column of anion exchange resin Amberlite IRA-400, and then reacted with L-lactic acid(0.14 g of 85% solution in water, 1.29 mmol) and sodium lactate(3.44 ml of 1M aqueous solution) in the same manner as described in Example 1B to give 0.085 g of (L-lactato-O,O')[(4R,5R)-4,5-bis-(aminomethyl)-1,3-dioxolane]platinum(II) as a white solid after purification in the same manner as described in Example 13A.

Yield: 24%

Example 14A

Synthesis of (L-lactato-O,O')[(4R,5R)-4,5-bis(aminomethyl)-2,2-dimethyl-1,3-dioxolane]platinum(II) by Method A 0.50 g(0.82 mmol) of cis-diiodo[(4R,5R)-4,5-bis-(aminomethyl)-2,2-dimethyl-1,3-dioxolane]platinum(II) was reacted with L-lactic acid(0.17 g of 85% solution in water, 1.64 mmol) and silver(I) oxide(0.38 g, 1.64 mmol) in water(30 ml) in the same manner as described in Example 1A to give 0.265 g of (L-lactato-O,O')[(4R,5R)-4,5-bis(aminomethyl)-2,2-dimethyl-1,3-dioxolane]platinum(II) as a white solid after purification by using preparative HPLC on Delta pak C18-100 Å reverse-phase bonded silica cartridge with a mixture of water-methanol(7:3, v/v) as the mobile phase.

Yield: 73% IR(KBr): 3419, 3216, 3131 cm$^{-1}$ (NH), 1634 cm$^{-1}$ (C=O) $^1$H NMR(DMSO-d$_6$/TMS): δ1.14(d, J=6.9 Hz, 3H, CH$_3$), 1.37(s, 6H, 2 CH$_3$), 2.66(m, 1H, CHNH$_2$), 2.80(m, 1H, CHNH$_2$), 3.18(m, 2H, 2 CHNH$_2$), 3.68(q, J=6.9 Hz, 1H, CHCH$_3$), 4.66(m, 2H, 2 CH), 6.16(br s, 1H, NH), 6.22(br s, 1H, NH), 6.48(br s, 2H, 2 NH) $^{13}$C NMR(DMSO-d$_6$): δ21.33, 26.39, 48.01, 48.29, 66.91, 77.49, 77.94, 108.74, 180.70 FAB-MS: (M+H)$^+$=443($^{194}$Pt, 33%), 444($^{195}$Pt, 34%) and 445($^{196}$Pt, 25%)

Example 14B

Synthesis of (L-lactato-O,O')[(4R,5R)-4,5-bis(aminomethyl)-2,2-dimethyl-1,3-dioxolane]platinum(II) by Method B 0.50 g(0.82 mmol) of cis-diiodo[(4R,5R)-4,5-bis-(aminomethyl)-2,2-dimethyl-1,3-dioxolane]platinum(II) was reacted with silver nitrate(0.28 g, 1.65 mmol), followed by passing the reaction mixture through a column of anion exchange resin Amberlite IRA-400, and then reacted with L-lactic acid(0.13 g of 85% solution in water, 1.23 mmol) and sodium lactate(3.3 ml of 1M aqueous solution) in the same manner as described in Example 1B to give 0.203 g of (L-lactato-O,O')[(4R,5R)-4,5-bis(aminomethyl)-2,2-dimethyl-1,3-dioxolane]platinum(II) as a white solid after purification in the same manner as described in Example 14A.

Yield: 56%

EXAMPLE 15A

Synthesis of
(L-lactato-O,O')[(4R,5R)-4,5-bis(aminomethyl)-1,3-dioxolane-2-spiro-1'-cyclopentane]-platinum(II) by Method A 0.50 g(0.79 mmol) of cis-diiodo[(4R,5R)-4,5-bis(aminomethyl)-1,3-dixolane-2-spiro-1'-cyclopentane]-platinum(II) was reacted with L-lactic acid(0.25 g of 85% solution in water, 2.36 mmol) and silver(I) oxide(0.55 g, 2.36 mmol) in a mixture of water(55 ml) and methanol(5 ml) in the same manner as described in Example 1A to give 0.175 g of (L-lactato-O,O')[(4R,5R)-4,5-bis(aminomethyl)-1,3-dioxolane-2-spiro-1'-cyclopentane]platinum(II) as a white solid after purification by using preparative HPLC on Delta pak C18-100 Å reverse-phase bonded silica cartridge with a mixture of water-methanol(6:4, v/v) as the mobile phase.

Yield: 47% IR(KBr): 3413, 3207, 3143 cm$^{-1}$ (NH), 1642 cm$^{-1}$ (C=O) FAB-MS: (M+H)$^+$=469($^{194}$Pt, 33%), 470($^{195}$Pt, 34%) and 471($^{196}$Pt, 25%)

EXAMPLE 15B

Synthesis of
(L-lactato-O,O')[(4R,5R)-4,5-bis(aminomethyl)-1,3-dioxolane-2-spiro-1'-cyclopentane]platinum(II) by Method B 0.50 g(0.79 mmol) of cis-diiodo[(4R,5R)-4,5-bis(aminomethyl)-1,3-dioxolane-2-spiro-1'-cyclopentane]-platinum(II) was reacted with silver nitrate(0.26 g, 1.54 mmol), followed by passing the reaction mixture through a column of anion exchange resin Amberlite IRA-400, and then reacted with L-lactic acid(0.08 g of 85% solution in water) and sodium lactate(3.1 ml of 1M aqueous solution) in the same manner as described in Example 1B to give 0.259 g of (L-lactato-O,O')[(4R,5R)-4,5-bis(aminomethyl)-1,3-dioxolane-2-spiro-1'-cyclopentane]platinum(II) as a white solid after purification in the same manner as described in Example 15A.

Yield: 70%

EXAMPLE 16A

Synthesis of
(L-lactato-O,O'){cyclohexanespiro-2'-[(4'R,5'R)-4',5'-bis(aminomethyl)-1',3'-dioxolane]}platinum(II) by Method A 0.50 g(0.77 mmol) of cis-diiodo{cyclohexanespiro-2'-[(4'R,5'R)-4',5'-bis(aminomethyl)-1',3'-dioxolane]}platinum(II) was reacted with L-lactic acid(0.16 g of 85% solution in water, 1.54 mmol) and silver(I) oxide(0.36 g, 1.55 mmol) in a mixture of water(110 ml) and methanol(10 ml) in the same manner as described in Example 1A to give 0.223 g of (L-lactato-O,O')[cyclohexanespiro-2'-[(4'R,5'R)-4',5'-bis(aminomethyl)-1',3'-dioxolane]]platinum(II) as a white solid after purification by using preparative HPLC on Delta pak C18-100 Å reverse-phase bonded silica cartridge with a mixture of water-methanol(5:5, v/v) as the mobile phase.

Yield: 60% IR(KBr): 3425, 3219, 3137 cm$^{-1}$ (NH), 1630 cm$^{-1}$ (C=O) FAB-MS: (M+H)$^+$=483($^{194}$Pt, 33%), 484($^{195}$Pt, 34%) and 485($^{196}$Pt, 25%)

EXAMPLE 16B

Synthesis of
(L-lactato-O,O'){cyclohexanespiro-2'-[(4'R,5'R)-4',5'-bis(aminomethyl)-1',3'-dioxolane]}platinum(II) by Method B 0.50 g(0.77 mmol) of cis-diiodo[cyclohexanespiro-2'-{(4'R,5'R)-4',5'-bis(aminomethyl)-1',3'-dioxolane]} platinum(II) was reacted with silver nitrate(0.26 g, 1.53 mmol), followed by passing the reaction mixture through a column of anion exchange resin Amberlite IRA-400, and then reacted with L-lactic acid(0.12 g of 85% solution in water, 1.15 mmol) and sodium lactate(3.1 ml of 1M aqueous solution) in the same manner as described in Example 1B to give 0.176 g of (L-lactato-O,O'){cyclohexanespiro-2'-[(4'R, 5'R)-4',5'-bis(aminomethyl)-1',3'-dioxolane]}platinum(II) as a white solid after purification in the same manner as described in Example 16A.

Yield: 47%

EXAMPLE 17A

Synthesis of
(L-lactato-O,O')[(4R,5R)-4,5-bis(aminomethyl)-2-methyl-1,3-dioxolane]platinum(II) by Method A 0.50 g(0.84 mmol) of cis-diiodo[(4R,5R)-4,5-bis(aminomethyl)-2-methyl-1,3-dioxolane]platinum(II) was reacted with L-lactic acid(0.018 g of 85% solution in water, 1.68 mmol) and silver(I) oxide(0.39 g, 1.68 mmol) in water(30 ml) in the same manner as described in Example 1A to give 0.207 g of (L-lactato-O,O')[(4R,5R)-4,5-bis(aminomethyl)-2-methyl-1,3-dioxolane]platinum (II) as a white solid after purification by using preparative HPLC on Delta pak C18-100 Å reverse-phase bonded silica cartridge with a mixture of water-methanol(9:1, v/v) as the mobile phase.

Yield: 57% IR(KBr): 3426, 3214, 3143 cm$^{-1}$ (NH), 1623 cm$^{-1}$ (C=O) $^1$H NMR(D$_2$O/DSS): δ1.30(d, J=6.9 Hz, 3H, CH$_3$), 1.40(d, J=4.8 Hz, 3H, CH$_3$), 2.88(m, 2H, 2 CHNH$_2$), 3.30(m, 1H, CHNH$_2$), 3.41(m, 1H, CHNH$_2$), 4.17(q, J=6.9 Hz, 1H, CHCH$_3$), 4.63(m, 1H, CH), 4.70(m, 1H, CH, overlapped with HOD), 5.28(q, J=4.8 Hz, 1H, CH) DSS(δ=0.015 ppm in D$_2$O) was used as the internal standard FAB-MS: (M+H)$^+$=429($^{194}$Pt, 33%), 430($^{195}$Pt, 34%) and 431($^{196}$Pt, 25%)

EXAMPLE 17B

Synthesis of
(L-lactato-O,O')[(4R,5R)-4,5-bis(aminomethyl)-2-methyl-1,3-dioxolane]platinum(II) by Method B 0.50 g(0.84 mmol) of cis-diiodo[(4R,5R)-4,5-bis(aminomethyl)-2-methyl-1,3-dioxolane]platinum(II) was reacted with silver nitrate(0.28 g, 1.65 mmol), followed by passing the reaction mixture through a column of anion exchange resin Amberlite IRA-400, and then reacted with L-lactic acid (0.09 g of 85% solution in water, 0.84 mmol) and sodium lactate(3.4 ml of 1M aqueous solution) in the same manner as described in Example 1B to give 0.275 g of (L-lactato-O,O')[(4R,5R)-4,5-bis(aminomethyl)-2-methyl-1,3-dioxolane] platinum(II) as a white solid after purification in the same manner as described in Example 17A.

Yield: 76%

EXAMPLE 18A

Synthesis of
(L-lactato-O,O')[(4R,5R)-4,5-bis(aminomethyl)-2-ethyl-1,3-dioxolane]platinum(II) by Method A 0.50 g(0.82 mmol) of cis-diiodo[(4R,5R)-4,5-bis-(aminomethyl)-2-ethyl-1,3-dioxolane]platinum(II) was reacted with L-lactic acid(0.26 g of 85% solution in water, 2.46 mmol) and silver (I) oxide(0.57 g, 2.46 mmol) in water(30 ml) in the same manner as described in Example 1A to give 0.267 g of (L-lactato-O,O')[(4R,5R)-4,5-bis(aminomethyl)-2-ethyl-1,3-dioxolane]platinum(II) as a white solid after purification by using preparative HPLC on Delta pak C18-100 Å reverse-phase bonded silica cartridge with a mixture of water-methanol(8:2, v/v) as the mobile phase.

Yield: 73% IR(KBr): 3405, 3209, 3138 cm$^{-1}$ (NH), 1636 cm$^{-1}$ (C=O) $^1$H NMR(D$_2$O/DSS): δ0.94(t, J=7.5 Hz, 3H, CH$_2$CH$_3$), 1.30(d, J=6.9 Hz, 3H, CH$_3$), 1.73(dq, J=4.5 Hz, J=7.5 Hz, 2H, CH$_2$CH$_3$), 2.88(m, 2H, 2 CHNH$_2$), 3.31(m, 1H, CHNH$_2$), 3.41(m, 1H, CHNH$_2$), 4.17(q, J=6.9 Hz, 1H, CHCH$_3$), 4.62(m, 1H, CH), 4.70(m, 1H, CH, overlapped with HOD), 5.15(t, J=4.5 Hz, 1H, CH). DSS(δ=0.015 ppm in D$_2$O) was used as the internal standard FAB-MS: (M+H)$^+$=443($^{194}$Pt, 33%), 444($^{195}$Pt, 34%) and 445($^{196}$Pt, 25%)

EXAMPLE 18B

Synthesis of
(L-lactato-O,O')[(4R,5R)-4,5-bis(aminomethyl)-2-ethyl-1,3-dioxolane]platinum(II) by Method B 0.50 g(0.82 mmol) of cis-diiodo[(4R,5R)-4,5-bis-(aminomethyl)-2-ethyl-1,3-dioxolane]platinum(II) was reacted with silver nitrate(0.27 g, 1.61 mmol), followed by passing the reaction mixture through a column of anion exchange resin Amberlite IRA-400, and then reacted with L-lactic acid(0.09 g of 85% solution in water, 0.82 mmol) and sodium lactate(3.3 ml of 1M aqueous solution) in the same manner as described in Example 1B to give 0.279 g of (L-lactato-O,O')[(4R,5R)-4,5-bis(aminomethyl)-2-ethyl-1,3-dioxolane]platinum(II) as a white solid after purification in the same manner as described in Example 18A.

Yield: 77%

EXAMPLE 19A

Synthesis of
(L-lactato-O,O')[(4R,5R)-4,5-bis(aminomethyl)-2-isopropyl-1,3-dioxolane]platinum(II) by Method A 0.50 g(0.80 mmol) of cis-diiodo[(4R,5R)-4,5-bis-(aminomethyl)-2-isopropyl-1,3-dioxolane]platinum(II) was reacted with L-lactic acid(0.26 g of 85% solution in water, 2.41 mmol) and silver(I) oxide(0.56 g, 2.41 mmol) in a mixture of water(55 ml) and methanol(5 ml) in the same manner as described in Example 1A to give 0.227 g of (L-lactato-O,O')[(4R,5R)-4,5-bis(aminomethyl)-2-isopropyl-1,3-dioxolane]platinum(II) as a white solid after purification by using preparative HPLC on Delta pak C18-100 Å reverse-phase bonded silica cartridge with a mixture of water-methanol(7:3, v/v) as the mobile phase.

Yield: 62% IR(KBr): 3425, 3212, 3136 cm$^{-1}$ (NH), 1634 cm$^{-1}$ (C=O) FAB-MS: (M+H)$^+$=457($^{194}$Pt, 33%), 458($^{195}$Pt, 34%) and 459($^{196}$Pt, 25%)

EXAMPLE 19B

Synthesis of
(L-lactato-O,O')[(4R,5R)-4,5-bis(aminomethyl)-2-isopropyl-1,3-dioxolane]platinum(II) by Method B 0.50 g(0.80 mmol) of cis-diiodo[(4R,5R)-4,5-bis-(aminomethyl)-2-isopropyl-1,3-dioxolane]platinum(II) was reacted with silver nitrate(0.27 g, 1.59 mmol) followed by passing the reaction mixture through a column of anion exchange resin Amberlite IRA-400, and then reacted with L-lactic acid(0.09 g of 85% solution in water, 0.82 mmol) and sodium lactate(3.2 ml of 1M aqueous solution) in the same manner as described in Example 1B to give 0.310 g of (L-lactato-O,O')[(4R,5R)-4,5-bis(aminomethyl)-2-isopropyl-1,3-dioxolane]platinum(II) as a white solid after purification in the same manner as described in Example 19A.

Yield: 85%

EXAMPLE 20

Synthesis of cis-cyclobutane-1,1-dicarboxylato [(4R,5R)-4,5-bis(aminomethyl)-1,3-dioxolane]platinum (II) by Method C A suspension of cis-diiodo[(4R,5R)-4,5-bis(aminomethyl)-1,3-dioxolane]platinum(II) (2.00 g, 3.4 mmol) and 1,1-cyclobutanedicarboxylic acid disilver salt(1.23 g, 3.4 mmol) in water(400 ml) was stirred at 60° C. for 16 hours in the dark. The resulting silver iodide was filtered through a pad of celite and the filtrate was again filtered using a millipore filter(0.22 μm). The filtrate was concentrated under a reduced pressure to 10 ml and the resulting white crystals were filtered to give 0.764 g of cis-cyclobutane-1,1-dicarboxylato[(4R,5R)-4,5-bis-(aminomethyl)-1,3-dioxolane]platinum(II).

Yield: 46% IR(KBr): 3432, 3239, 3191, 3126 cm$^{-1}$ (NH), 1634, 1590 cm$^{-1}$ (C=O) $^{13}$C NMR(DMSO-d$_6$): δ14.85, 30.32, 47.75, 55.43, 78.37, 93.87, 177.30 Elemental analysis: Calcd. for C$_{11}$H$_{18}$N$_2$O$_6$Pt: C 28.15, H 3.87, N 5.97 (%) Found: C. 28.20, H 3.88, N 5.86 (%) FAB-MS: (M+H)$^+$=469($^{194}$Pt, 33%), 470($^{195}$Pt, 34%) and 471($^{196}$Pt, 25%)

EXAMPLE 21

Synthesis of
cis-cyclobutane-1,1-dicarboxylato[(4S,5S)-4,5-bis-(aminomethyl)-1,3-dioxolane]platinum(II) by Method C 2.00 g of cis-diiodo[(4S,5S)-4,5-bis(aminomethyl)-1,3-dioxolane]platinum(II) was reacted with 1,1-cyclobutanedicarboxylic acid disilver salt in the same manner as described in Example 20 to give 0.78 g of cis-cyclobutane-1,1-dicarboxylato[(4S,5S)-4,5-bis-(aminomethyl)-1,3-dioxolane]platinum(II).

Yield: 48% Elemental analysis: Calcd. for C$_{11}$H$_{18}$N$_2$O$_6$Pt: C 28.15, H 3.87, N 5.97 (%) Found: C 28.10, H 3.83, N 5.80 (%) FAB-MS: (M+H)$^+$=469($^{194}$Pt, 33%), 470($^{195}$Pt, 34%) and 471 ($^{196}$Pt, 25%)

EXAMPLE 22

Synthesis of
cis-cyclobutane-1,1-dicarboxylato[(4R,5R)-4,5-bis-(aminomethyl)-2-methyl-1,3-dioxolane]platinum(II) by Method C A suspension of cis-diiodo[(4R,5R)-4,5-bis(aminomethyl)-2-methyl-1,3-dioxolane]platinum(II)(1.00 g, 1.7 mmol) and 1,1-cyclobutanedicarboxylic acid disilver salt(0.60 g, 1.7 mmol) in water(170 ml) was stirred at 60° C. for 16 hours in the dark. The resulting silver iodide was filtered through a pad of celite and the filtrate was again filtered using a millipore filter(0.22 μm). The filtrate was concentrated under a reduced pressure to 30 ml and the concentrate was purified by using preparative HPLC on Delta Pak C18-100 Å reverse-phase bonded silica cartridge with a mixture of water-methanol(8:2, v/v) as the mobile phase to give 0.446 g of cis-cyclobutane-1,1-dicarboxylato[(4R,5R)-4,5-bis-(aminomethyl)-2-methyl-1,3-dioxolane]platinum(II) as a white solid.

Yield: 55% IR(KBr): 3447, 3218, 3132 cm$^{-1}$ (NH), 1634 cm$^{-1}$ (C=O) $^{13}$C NMR(DMSO-d$_6$): δ14.82, 1949, 30.21, 30.39, 47.87, 47.98, 55.42, 77.61, 79.73, 100.44, 177.29 Elemental analysis: Calcd. for $C_{12}H_{20}N_2O_6Pt$: C 29.82, H 4.17, N 5.80 (%) Found: C 29.69, H 4.29, N 5.57 (%) FAB-MS: (M+H)$^+$=483($^{194}$Pt, 33%), 484($^{195}$Pt, 34%) and 485($^{196}$Pt, 25%)

EXAMPLE 23

Synthesis of cis-cyclobutane-1,1-dicarboxylato[(4S,5S)-4,5-bis-(aminomethyl)-2-methyl-1,3-dioxolane]platinum(II) by Method C 1.00 g of cis-diiodo[(4S,5S)-4,5-bis(aminomethyl)-2-methyl-1,3-dioxolanep]platinum(II) was reacted with 1,1-cyclobutanedicarboxylic acid disilver salt in the same manner as described in Example 22 to give 0.435 g of cis-cyclobutane-1,1-dicarboxylato[(4S,5S)-4,5-bis-(aminomethyl)-2-methyl-1,3-dioxolane]platinum(II).

Yield: 54% Elemental analysis: Calcd. for $C_{12}N_{20}N_2O_6Pt$: C 29.82, H 4.17, N 5.80 (%) Found: C 29.68, H 4.25, N 5.70 (%) FAB-MS: (M+H)$^+$=483($^{194}$Pt, 33%), 484($^{195}$Pt, 34%) and 485($^{196}$Pt, 25%)

EXAMPLE 24

Synthesis of cis-cyclobutane-1,1-dicarboxylato[(4R,5R)-4,5-bis-(aminomethyl)-2-ethyl-1,3-dioxolane]platinum(II) by Method C 1.50 g of cis-diiodo[(4R,5R)-4,5-bis(aminomethyl)-2-ethyl-1,3-dioxolane]platinum(II) was reacted with 1,1-cyclobutanedicarboxylic acid disilver salt in the same manner as described in Example 20 to give 0.693 g of cis-cyclobutane-1,1-dicarboxylato[(4R,5R)-4,5-bis-(aminomethyl)-2-ethyl-1,3-dioxolane]platinum(II) as colorless crystals.

Yield: 57% IR(KBr): 3446, 3189, 3072 cm$^{-1}$ (NH), 1609 cm$^{-1}$ (C=O) $^{13}$C NMR(DMSO-d6): δ7.63, 14.79, 26.33, 30.27, 47.90, 47.98, 55.40, 77.70, 79.52, 104.08, 177.24 Elemental analysis: Calcd. for $C_{13}H_{22}N_2O_6Pt$: C 31.39, H 4.46, N 5.63 (%) Found: C 31.60, H 4.23, N 5.85 (%) FAB-MS: (M+H)$^+$=497($^{194}$Pt, 33%), 498($^{195}$Pt, 34%) and 499($^{196}$Pt, 25%)

EXAMPLE 25

Synthesis of cis-cyclobutane-1,1-dicarboxylato[(4S,5S)-4,5-bis-(aminomethyl)-2-ethyl-1,3-dioxolane]platinum(II) by Method C 1.50 g of cis-diiodo[(4S,5S)-4,5-bis(aminomethyl)-2-ethyl-1,3-dioxolane]platinum(II) was reacted with 1,1-cyclobutanedicarboxylic acid disilver salt in the same manner as described in Example 20 to give 0.680 g of cis-cyclobutane-1,1-dicarboxylato[(4S,5S)-4,5-bis-(aminomethyl)-2-ethyl-1,3-dioxolane]platinum(II).

Yield: 56% Elemental analysis: Calcd. for $C_{13}H_{22}N_2O_6Pt$: C 31.39, H 4.46, N 5.63 (%) Found: C 31.52, H 4.15, N 5.79 (%) FAB-MS: (M+H)$^+$=497($^{194}$Pt, 33%), 498($^{195}$Pt, 34%) and 499($^{196}$Pt, 25%)

EXAMPLE 26

Synthesis of cis-cyclobutane-1,1-dicarboxylato[(4R,5R)-4,5-bis-(aminomethyl)-2,2-dimethyl-1,3-dioxolane]platinum(II) by Method C 1.30 g of cis-diiodo[(4R,5R)-4,5-bis(aminomethyl)-2,2-dimethyl-1,3-dioxolane]platinum(II) was reacted with 1,1-cyclobutane-dicarboxylic acid disilver salt in the same manner as described in Example 20 to give 0.586 g of cis-cyclobutane-1,1-dicarboxylato[(4R,5R)-4,5-bis(aminomethyl)-2,2-dimethyl-1,3-dioxolane]-platinum(II) as white crystals.

Yield: 55% IR(KBr): 3424, 3239, 3084 cm$^{-1}$ (NH), 1616, 1587 cm$^{-1}$ (C=O) $^{13}$C NMR(DMSO-d$_6$): δ14.86, 26.41, 30.29, 48.47, 55.44, 78.18, 108.32, 177.28 Elemental analysis: Calcd. for $C_{13}N_{22}N_2O_6Pt$: C 31.39, H 4.46, N 5.63 (%) Found: C 31.38, H 4.50, N 5.55 (%) FAB-MS: (M+H)$^+$=497($^{194}$Pt, 33%), 498($^{195}$Pt, 34%) and 499($^{196}$Pt, 25%)

EXAMPLE 27

Synthesis of cis-cyclobutane-1,1-dicarboxylato[(4S,5S)-4,5-bis-(aminomethyl)-2,2-dimethyl-1,3-dioxolane]platinum(II) by Method C 1.30 g of cis-diiodo[(4S,5S)-4,5-bis(aminomethyl)-2,2-dimethyl-1,3-dioxolane]platinum(II) was reacted with 1,1-cyclobutanedicarboxylic acid disilver salt in the same manner as described in Example 20 to give 0.573 g of cis-cyclobutane-1,1-dicarboxylato[(4S,5S)-4,5-bis-(aminomethyl)-2,2-dimethyl-1,3-dioxolane]platinum-(II).

Yield: 54% Elemental analysis: Calcd. for $C_{13}N_{22}N_2O_6Pt$: C 31.39, H 4.46, N 5.63 (%) Found: C 31.31, H 4.32, N 5.50 (%) FAB-MS: (M+H)$^+$=497($^{194}$Pt, 33%), 498($^{195}$Pt, 34%) and 499($^{196}$Pt, 25%)

EXAMPLE 28

Synthesis of cis-cyclobutane-1,1-dicarboxylato[(4R,5R)-4,5-bis-(aminomethyl)-2-isopropyl-1,3-dioxolane]platinum(II) by Method C 1.50 g of cis-diiodo[(4R,5R)-4,5-bis(aminomethyl)-2-isopropyl-1,3-dioxolane]platinum(II) was reacted with 1,1-cyclobutanedicarboxylic acid disilver salt in the same manner as described in Example 20 to give 0.63 g of cis-cyclobutane-1,1-dicarboxylato[(4R,5R)-4,5-bis-(aminomethyl)-2-isopropyl-1,3-dioxolane]platinum(II) as white crystals.

Yield: 51% IR (KBr): 3433, 3189, 3070 cm$^{-1}$ (NH), 1608, 1593 cm$^{-1}$ (C=O) $^{13}$C NMR(DMSO-d$_6$): δ14.80, 16.39, 16.44, 30.17, 30.37, 31.32, 47.83, 48.83, 55.41, 77.92, 79.48, 106.83, 177.24 Elemental analysis: Calcd. for $C_{14}H_{24}N_2O_6Pt$: C 32.88, H 4.73, N 5.48 (%) Found: C 33.12, H 4.39, N 5.35 (%) FAB-MS: (M+H)$^+$=511($^{194}$Pt, 33%), 512($^{195}$Pt, 34%) and 513($^{196}$Pt, 25%)

EXAMPLE 29

Synthesis of cis-cyclobutane-1,1-dicarboxylato[(4S,5S)-4,5-bis(aminomethyl)-2-isopropyl-1,3-dioxolane]platinum(II) by Method C 1.50 g of cis-diiodo[(4S,5S)-4,5-bis(aminomethyl)-2-isopropyl-1,3-dioxolane]platinum(II) was reacted with 1,1-cyclobutane-dicarboxylic acid disilver salt in the same manner as described in Example 20 to give 0.57 g of cis-cyclobutane-1,1-dicarboxylato[(4R,5R)-4,5-bis(aminomethyl)-2-isopropyl-1,3-dioxolane]platinum(II).

Yield: 46% Elemental analysis: Calcd. for $C_{14}H_{24}N_2O_6Pt$: C 32.88, H 4.73, N 5.48 (%) Found: C 33.10, H 4.50, N 5.40 (%) FAB-MS: $(M+H)^+=511(^{194}Pt, 33\%), 512(^{195}Pt, 34\%)$ and $513(^{196}Pt, 25\%)$

EXAMPLE 30

Synthesis of cis-cyclobutane-1,1-dicarboxylato[(4R,5R)-4,5-bis(aminomethyl)-1,3-dioxolane-2-spiro-1'-cyclopentane]platinum(II) by Method C 1.50 g of cis-diiodo[(4R,5R)-4,5-bis(aminomethyl)-1,3-dioxolane-2-spiro-1'-cyclopentane]platinum(II) was reacted with 1,1-cyclobutanedicarboxylic acid disilver salt in the same manner as described in Example 20 to give 0.561 g of cis-cyclobutane-1,1-dicarboxylato[(4R,5R)-4,5-bis(aminomethyl)-1,3-dioxolane-2-spiro-1'-cyclopentane]platinum(II) as a white powder.

Yield: 45% IR(KBr): 3445, 3190, 3085 cm$^{-1}$ (NH), 1615 cm$^{-1}$ (C=O) $^{13}$C NMR(DMSO-d$_6$): δ15.26, 23.30, 30.72, 36.58, 48.61, 55.84, 78.34, 118.69, 178.13 Elemental analysis: Calcd. for $C_{15}H_{24}N_2O_6Pt$: C 34.42, H 4.62, N 5.35 (%) Found: C 34.78, H 4.84, N 5.08 (%) FAB-MS: $(M+H)^+=523(^{194}Pt, 33\%), 524(^{195}Pt, 34\%)$ and $525(^{196}Pt, 25\%)$

EXAMPLE 31

Synthesis of cis-cyclobutane-1,1-dicarboxylato[(4S,5S)-4,5-bis(aminomethyl)-1,3-dioxolane-2-spiro-1'-cyclopentane]platinum(II) by Method C 1.50 g of cis-diiodo[(4S,5S)-4,5-bis(aminomethyl)-1,3-dioxolane-2-spiro-1'-cyclopentane]platinum(II) was reacted with 1,1-cyclobutanedicarboxylic acid disilver salt in the same manner as described in Example 20 to give 0.665 g of cis-cyclobutane-1,1-dicarboxylato[(4S,5S)-4,5-bis(aminomethyl)-1,3-dioxolane-2-spiro-1'-cyclopentane]platinum(II).

Yield: 54% Elemental analysis: Calcd. for $C_{15}H_{24}N_2O_6Pt$: C 34.42, H 4.62, N 5.35 (%) Found: C 34.78, H 4.56, N 5.20 (%) FAB-MS: $(M+H)^+=523(^{194}Pt, 33\%), 524(^{195}Pt, 34\%)$ and $525(^{196}Pt, 25\%)$

EXAMPLE 32

Synthesis of cis-cyclobutane-1,1-dicarboxylato[(4R,5R)-4,5-bis-(aminomethyl)-1,3-dioxolane-2-spiro-1'-cyclohexane]platinum(II) by Method C 1.50 g of cis-diiodo[(4R,5R)-4,5-bis(aminomethyl)-1,3-dioxolane-2-spiro-1'-cyclohexane]platinum(II) was reacted with 1,1-cyclobutanedicarboxylic acid disilver salt in the same manner as described in Example 20 to give 0.510 g of cis-cyclobutane-1,1-dicarboxylato[(4R,5R)-4,5-bis(aminomethyl)-1,3-dioxolane-2-spiro-1'-cyclohexane]platinum(II) as a white powder.

Yield: 41% IR(KBr): 3445, 3190, 3069 cm$^{-1}$ (NH), 1607 cm$^{-1}$ (C=O) $^{13}$C NMR(DMSO-d$_6$): δ14.82, 23.32, 24.41, 30.26, 35.55, 48.60, 55.42, 77.84, 108.72, 117.24 Elemental analysis: Calcd. for $C_{16}H_{26}N_2O_6Pt$: C 35.76, H 4.88, N 5.21 (%) Found: C 35.71, H 4.53, N 5.05 (%) FAB-MS: $(M+H)^+=537(^{194}Pt, 33\%), 538(^{195}Pt, 34\%)$ and $539(^{196}Pt, 25\%)$

EXAMPLE 33

Synthesis of cis-malonato[(4R,5R)-4,5-bis(aminomethyl)-1,3-dioxolane]platinum(II) by Method C A suspension of cis-diiodo[(4R,5R)-4,5-bis(aminomethyl)-3,4-dioxolane]platinum(II)(1.00 g, 1.72 mmol) and malonic acid disilver salt(0.55 g, 1.72 mmol) in water(150 ml) was stirred at 60° C. for 16 hours in the dark. The resulting silver iodide was filtered through a pad of celite and the filtrate was again filtered using a millipore filter(0.22 μm). The filtrate was concentrated under a reduced pressure to 10 ml and the resulting white crystals were filtered to give 0.498 g of cis-malonato[(4R,5R)-4,5-bis(aminomethyl)-1,3-dioxolane]platinum(II). The mother liquor was purified by using preparative HPLC on Delta pak C18-100 Å reverse-phase bonded silica cartridge with a mixture of water-methanol(9:1, v/v) as the mobile phase to give 0.104 g of an additional product.

Yield: 81% IR(KBr): 3481, 3243, 3172, 3048 cm$^{-1}$ (NH), 1652, 1606 cm$^{-1}$ (C=O) $^1$H NMR(DMSO-d$_6$/TMS): δ2.62(m, 2H, 2 CHNH$_2$), 3.04(m, 2H, 2 CHNH$_2$), 3.26(s, 2H, CH$_2$), 4.41(m, 2H, 2 CH), 4.94(s, 2H, OCH$_2$O), 5.38(br s, 2H, 2 NH), 5.47(br s, 2H, 2 NH) $^{13}$C NMR(DMSO-d$_6$): δ47.54, 50.22, 78.30, 93.86, 174.01 FAB-MS: $(M+H)^+=429(^{194}Pt, 33\%), 430(^{195}Pt, 34\%)$ and $431(^{196}Pt, 25\%)$

EXAMPLE 34

Synthesis of cis-malonato[(4R,5R)-4,5-bis(aminomethyl)-2-methyl-1,3-dioxolane]platinum(II) by Method C cis-Diiodo[(4R,5R)-4,5-bis(aminomethyl)-2-methyl-1,3-dioxolane]platinum(II)(1.00 g, 1.68 mmol) was reacted with malonic acid disilver salt(0.53 g, 1.68 mmol) in water(150 ml) in the same manner as described in Example 33 to give 0.239 g of cis-malonato[(4R,5R)-4,5-bis(aminomethyl)-2-methyl-1,3-dioxolane]platinum(II). The mother liquor was purified by using preparative HPLC on Delta pak C18-100 Å reverse-phase bonded silica cartridge with a mixture of water-methanol(9:1, v/v) as the mobile phase to give 0.361 g of an additional product.

Yield: 81% IR(KBr): 3454, 3383, 3214, 3065 cm$^{-1}$ (NH), 1643-1555 cm$^{-1}$ (C=O) $^1$H NMR(DMSO-d$_6$/TMS): δ1.27(d, J=4.8 Hz, 3H, CH$_3$), 2.60(m, 2H, 2 CHNH$_2$), 2.94(m, 1H, CHNH$_2$), 3.05(m, 1H, CHNH$_2$), 3.26(s, 2H, CH$_2$), 4.36(m, 1H, CH), 4.61(m, 1H, CH), 5.16(q, J=4.8 Hz, 1H, CH), 5.31(br s, 1H, NH), 5.48(br s, 3H, 3 NH) $^{13}$C NMR(DMSO-d$_6$): δ19.54, 47.75, 47.81, 50.21, 77.50, 79.72, 100.44, 174.03 FAB-MS: $(M+H)^+=443(^{194}Pt, 33\%), 444(^{195}Pt, 34\%)$ and $445(^{196}Pt, 25\%)$

EXAMPLE 35

Synthesis of cis-malonato[(4R,5R)-4,5-bis(aminomethyl)-2-ethyl-1,3-dioxolane]platinum(II) by Method C cis-Diiodo[4R, 5R)-4,5-bis(aminomethyl)-2-ethyl-1,3-dioxolane]platinum(II)(1.00 g, 1.64 mmol) was reacted with malonic acid disilver salt(0.52 g, 1.64 mmol) in water(150 ml) in the same manner as described in Example 33 to give 0.242 g of cis-malonato-[(4R,5R)-4,5-bis-(aminomethyl)-2-ethyl-1,3-dioxolane]platinum(II). The mother liquor was purified by using preparative HPLC on Delta pak C18-100 Å reverse-phase bonded silica cartridge with a mixture of water-methanol(7:3, v/v) as the mobile phase to give 0.430 g of an additional product.

Yield: 89% IR(KBr): 3447, 3214, 3120 cm$^{-1}$ (NH), 1628 cm$^{-1}$ (C=O) $^1$H NMR(DMSO-d$_6$/TMS): δ0.87(t, J=7.5 Hz, 3H, CH$_3$), 1.58(dq, J=4.5 Hz, J=7.5 Hz, 2H, CH$_2$CH$_3$), 2.59(m, 2H, 2 CHNH$_2$), 2.97(m, 1H, CHNH$_2$), 3.08(m, 1H, CHNH$_2$), 3.26(s, 2H, CH$_2$), 4.33(m, 1H, CH), 4.57(m, 1H, CH), 5.00(t, J=4.5 Hz, 1H, CH), 5.29(br s, 1H, NH), 5.46(br s, 3H, 3 NH) $^{13}$C NMR(DMSO-d$_6$): δ7.65, 26.35, 47.74, 47.84, 50.21, 77.65, 79.50, 104.12, 174.04 FAB-MS: (M+H)$^+$=457($^{194}$Pt, 33%), 458($^{195}$Pt, 34%) and 459($^{196}$Pt 25%)

EXAMPLE 36

Synthesis of cis-malonato[(4R,5R)-4,5-bis(aminomethyl)-2,2-dimethyl-1,3-dioxolane]platinum(II) by Method C cis-Diiodo[(4R,5R)-4,5-bis(aminomethyl)-2,2-dimethyl-1,3-dioxolane]platinum(II)(0.70 g, 1.15 mmol) was reacted with malonic acid disilver salt(0.37 g, 1.15 mmol) in water(100 ml) in the same manner as described in Example 33 to give 0.259 g of cis-malonato-[(4R,5R)-4,5-bis(aminomethyl)-2,2-dimethyl-1,3-dioxolane]platinum(II). The mother liquor was purified by using preparative HPLC on Delta pak C18-100 Å reverse-phase bonded silica cartridge with a mixture of water-methanol(7:3, v/v) as the mobile phase to give 0.206 g of an additional product.

Yield: 89% IR(KBr): 3445, 3207, 3107 cm$^{-1}$ (NH), 1627 cm$^{-1}$(C=O) $^1$H NMR(DMSO-d$_6$/TMS): δ1.34(s, 6H, 2 CH$_3$), 2.56(m, 2H, 2 CHNH$_2$), 3.02(m, 2H, 2 CHNH$_2$), 3.26(s, 2H, CH$_2$), 4.45(m, 2H, 2 CH), 5.45(br s, 2H, 2 NH), 5.56(br s, 2H, NH) FAB-MS: (M+H)$^+$=457($^{194}$Pt, 33%), 458($^{195}$Pt, 34%) and 459($^{196}$Pt, 25%)

EXAMPLE 37

Synthesis of cis-malonato[(4R,5R)-4,5-bis(aminomethyl)-2,2-diethyl-1,3-dioxolane]platinum(II) by Method C cis-Diiodo[(4R,5R)-4,5-bis(aminomethyl)-2,2-diethyl-1,3-dioxolane]platinum(II)(1.00 g, 1.57 mmol) was reacted with malonic acid disilver salt(0.50 g, 1.57 mmol) in water(200 ml) in the same manner as described in Example 33 to give 0.533 g of cis-malonato-[(4R,5R)-4,5-bis(aminomethyl)-2,2-diethyl-1,3-dioxolane]platinum(II) as white crystals.

Yield: 70% IR(KBr): 3440, 3200, 3053 cm$^{-1}$(NH), 1611 cm$^{-1}$ (C=O) $^1$H NMR(DMSO-d$_6$/TMS): δ0.84(t,J=7.2 Hz, 6H, 2 CH$_3$), 1.59(q, J=7.2 Hz, 4H, 2 CH$_2$), 2.55(m, 2H, 2 CHNH$_2$), 3.05(m, 2H, 2 CHNH$_2$), 3.25(s, 2H, CH$_2$), 4.43(m, 2H, 2 CH), 5.38(br s, 2H, 2 NH), 5.50(br s, 2H, 2 NH) $^{13}$C NMR(DMSO-d$_6$): δ7.77, 29.65, 48.33, 50.24, 78.63, 112.06, 174.01 FAB-MS: (M+H)$^+$=485($^{194}$Pt, 33%), 486($^{195}$Pt, 34%) and 487($^{196}$Pt, 25%)

EXAMPLE 38

Synthesis of cis-malonato[(4R,5R)-4,5-bis(aminomethyl)-2-isopropyl-1,3-dioxolane]platinum(II) by Method C cis-Diiodo[(4R,5R)-4,5-bis(aminomethyl)-2-isopropyl-1,3-dioxolane]platinum(II)(1.00 g, 1.61 mmol) was reacted with malonic acid disilver salt(0.51 g, 1.61 mmol) in water(150 ml) in the same manner as described in Example 33 to give 0.324 g of cis-malonato-[(4R,5R)-4,5-bis(aminomethyl)-2-isopropyl-1,3-dioxolane]platinum(II). The mother liquor was purified by using preparative HPLC on Delta pak C18-100 Å reverse-phase bonded silica cartridge with a mixture of water-methanol(6:4, v/v) as the mobile phase to give 0.350 g of an additional product.

Yield: 89% IR(KBr): 3431, 3205, 3049 cm$^{-1}$ (NH), 1612 cm$^{-1}$ (C=O) $^1$H NMR(DMSO-d$_6$/TMS): δ0.87(d, J=6.6 Hz, 6H, 2 CH$_3$), 1.75(m, 1H, CH(CH$_3$)$_2$), 2.59(m, 2H, 2 CHNH$_2$), 2.98(m, 1H, CHNH$_2$), 3.09(m, 1H, CHNH$_2$), 3.26(s, 2H, CH$_2$), 4.31(m, 1H, CH), 4.55(m, 1H, CH), 4.80(d, J=4.5 Hz, 1H, CH), 5.31(br s, 1H, NH), 5.48(br s, 3H, 3 NH) FAB-MS: (M+H)$^+$=471($^{194}$Pt, 33%), 472($^{195}$Pt,34%) and 473($^{196}$Pt, 25%)

EXAMPLE 39

Synthesis of cis-malonato[(4R,5R)-4,5-bis(aminomethyl)-1,3-dioxolane-2-spiro-1'-cyclopentane]platinum(II) by Method C cis-Diiodo[(4R,5R)-4,5-bis(aminomethyl)-1,3-dioxolane-2-spiro-1'-cyclopentane]platinum(II)(1.00 g, 1.57 mmol) was reacted with malonic acid disilver salt(0.50 g, 1.57 mmol) in water(250 ml) in the same manner as described in Example 33 to give 0.265 g of cis-malonato[(4R,5R)-4,5-bis(aminomethyl)-1,3-dioxolane-2-spiro-1'-cyclopentane]platinum(II). The mother liquor was purified by using prepavative HPLC on Delta pak C18-100 Å reverse-phase bonded silica cartridge with a mixture of water-methanol(6:4, v/v) as the mobile phase to give 0.159 g of an additional product.

Yield: 56% IR(KBr): 3433, 3200, 3053 cm$^{-1}$ (NH), 1613 cm$^{-1}$ (C=O) $^1$H NMR(DMSO-d$_6$/TMS): δ1.45–1.90(m, 8H, cyclopentyl), 2.55(m, 2H, 2CHNH$_2$), 3.03(m, 2H, 2 CHNH$_2$), 3.26(s, 2H, CH$_2$), 4.41(m, 2H, 2 CH), 5.38(br s, 2H, 2 NH), 5.50(br s, 2H, 2 NH) FAB-MS: (M+H)$^+$=483($^{194}$Pt, 33%), 484($^{195}$Pt, 34%) and 485($^{196}$Pt, 25%)

EXAMPLE 40

Synthesis of cis-dimethylmalonato[(4R,5R)-4,5-bis(aminomethyl)-2-ethyl-1,3-dioxolane]platinum(II) by Method C cis-Diiodo[(4R,5R)-4,5-bis(aminomethyl)-2-ethyl-1,3-dioxolane]platinum(II)(1.00 g, 1.64 mmol) was reacted with dimethylmalonic acid disilver salt(0.57 g, 1.64 mmol) in water (150 ml) in the same manner as described in Example 33 to give 0.401 g of cis-dimethylmalonato[(4R,5R)-4,5-bis(aminomethyl)-2-ethyl-1,3-dioxolane]platinum(II). The mother liquor was purified by using preparative HPLC on Delta pak C18-100 Å reverse-phase bonded silica cartridge with a mixture of water-methanol(6:4, v/v) as the mobile phase to give 0.261 g of an additional product.

Yield: 83% IR(KBr): 3454, 3211, 3126 cm$^{-1}$ (NH), 1650–1597 cm$^{-1}$ (C=O) FAB-MS: (M+H)$^+$=485($^{194}$Pt, 33%), 486($^{195}$Pt, 34%) and 487($^{196}$Pt, 25%)

EXAMPLE 41

Synthesis of cis-dimethylmalonato[(4R,5R)-4,5-bis(aminomethyl)-2-isopropyl-1,3-dioxolane]platinum(II) by Method C cis-Diiodo[(4R,5R)-4,5-bis(aminomethyl)-2-isopropyl-1,3-dioxolane]platinum(II)(0.95 g, 1.53 mmol) was reacted with dimethylmalonic acid disilver salt(0.53 g, 1.53 mmol) in water (150 ml) in the same manner as described in Example 33 to give 0.113 g of cis-dimethylmalonato[(4R,5R)-4,5-bis(aminomethyl)-2-isopropyl-1,3-dioxolane]platinum(II). The mother liquor was purified by using preparative HPLC on Delta pak C18-100 Å reverse-phase bonded silica cartridge with a mixture of water-methanol(5:5, v/v) as the mobile phase to give 0.457 g of an additional product.

Yield: 75% IR(KBr): 3449, 3216, 3130 cm$^{-1}$ (NH), 1630 cm$^{-1}$ (C=O) FAB-MS: (M+H)$^+$=499($^{194}$Pt, 33%), 500($^{195}$Pt, 34) and 501($^{196}$Pt, 25%)

EXAMPLE 42

Synthesis of cis-dimethylmalonato[(4R,5R)-4,5-bis(aminomethyl)-1,3-dioxolane-2-spiro-1'-cyclopentane]platinum(II) by Method C cis-Diiodo[(4R,5R)-4,5-bis(aminomethyl)-1,3-dioxolane-2-spiro-1'cyclopentane]platinum(II)(1.00 g, 1.57 mmol) was reacted with dimethylmalonic acid disilver salt(0.54 g, 1.57 mmol) in water (150 ml) in the same manner as described in Example 33 to give 0.009 g of cis-dimethylmalonato[(4R,5R)-4,5-bis(aminomethyl)-1,3-dioxolane-2-spiro-1'-cyclopentane]platinum(II). The mother liquor was purified by using preparative HPLC on Delta pak C18-100Å reverse-phase bonded silica cartridge with a mixture of water-methanol(5:5, v/v) as the mobile phase to give 0.503 g of an additional product.

Yield: 64% IR(KBr): 3454, 3218, 3131 cm$^{-1}$ (NH), 1668–1652 cm$^{-1}$ (C=O) FAB-MS: (M+H)$^+$=511($^{194}$Pt, 33%), 512($^{195}$Pt, 34%) and 513($^{196}$Pt, 25%)

EXAMPLE 43

Synthesis of cis-ethylmalonato[(4R,5R)-4,5-bis(aminomethyl)-2-ethyl-1,3-dioxolane]platinum(II) by Method C cis-diiodo[(4R,5R)-4,5-bis(aminomethyl)-2-ethyl-1,3-dioxolane[platinum(II) (1.00 g, 1.64 mmol) was reacted with ethylmalonic acid disilver salt (0.57 g, 1.64 mmol) in water (150 ml) in the same manner as described in Example 33 to give 0.605 g of cis-ethylmalonato[(4R,5R)-4,5-bis(aminomethyl)-2-ethyl-1,3-dioxolane]platinum(II). The mother liquor was purified by using preparative HPLC on Delta pak C18-100 Å reverse-phase bonded silica cartridge with a mixture of water-methanol (6:4, v/v) as the mobile phase to give 0.154 g of an additional product.

Yield: 95% IR(KBr): 3446, 3205, 3122 cm$^{-1}$ (NH), 1648, 1635 cm$^{-1}$ (C=O) FAB-MS: (M+H)$^+$=485($^{194}$Pt, 33%), 486($^{195}$Pt, 34%) and 487($^{196}$Pt, 25%)

EXAMPLE 44

Synthesis of cis-ethylmalonato[(4R,5R)-4,5-bis(aminomethyl)-2-isopropyl-1,3-dioxolane]platinum(II) by Method C cis-diiodo[(4R,5R)-4,5-bis(aminomethyl)-2-isopropyl-1,3-dioxolane]platinum(II) (0.95 g, 1.53 mmol) in water (150 ml) in the same manner as described in Example 33 to give 0.278 g of cis-ethylmalonato[(4R,5R)-4,5-bis(aminomethyl)-2-isopropyl-1,3-dioxolane]platinum(II). The mother liquor was purified by using preparative HPLC on Delta pak C18-100 Å reverse-phase bonded silica cartridge with water-methanol (5:5, v/v) as the mobile phase to give 0.169 g of an additional product.

Yield: 59% IR(KBr): 3448, 3202, 3126 cm$^{-1}$ (NH), 1617 cm$^{-1}$ (C=O) FAB-MS: (M+H)$^+$=499($^{194}$Pt, 33%), 500($^{195}$Pt, 34%) and 501($^{196}$Pt, 25%)

EXAMPLE 45

Synthesis of cis-ethylmalonato[(4R,5R)-4,5-bis(aminomethyl)-1,3-dioxolane-2-spiro-1'-cyclopentane]platinum (II) by Method C cis-Diiodo[(4R,5R)-4,5-bis(aminomethyl)-1,3-dioxolane-2-spiro-1'-cyclopentane)platinum(II) (1.00 g, 1.57 mmol) was reacted with ethylmalonic acid disilver salt(0.54 g, 1.57 mmol) in water (150 ml) in the same manner as described in Example 33 to give 0.657 g of cis-ethylmalonato[(4R,5R)-4,5-bis(aminomethyl)-1,3-dioxolane-2-spiro-1'-cyclopentane]platinum(II). The mother liquor was purified by using preparative HPLC on Delta pak C18-100 Å reverse-phase bonded silica cartridge with a mixture of water-methanol (5:5, v/v) as the mobile phase to give 0.036 g of an additional product.

Yield: 86% IR(KBr): 3448, 3197, 3092 cm$^{-1}$ (NH), 1662 cm$^{-1}$ (C=O) FAB-MS: (M+H)$^+$=511($^{194}$Pt, 33%), 512($^{195}$Pt, 34%) and 513($^{196}$Pt, 25%)

EXAMPLE 46

Synthesis of cis-cyclobutane-1,1-dicarboxylato[(4S,5S)-4,5-bis(aminomethyl)-1,3-dioxolane-2-spiro-1'-cyclohexane]platinum(II) by Method D To a stirred suspension of cis-diiodo[(4S,5S)-4,5-bis(aminomethyl)-1,3-dioxolane-2-spiro-1'-cyclohexane]platinum(II) (2.00 g, 3.1 mmol) in water(100 ml) was added a solution of silver nitrate (1.05 g, 6.2 mmol) in water (15 ml). The mixture was heated at 60° C. for 3 hours in the dark, cooled to a room temperature and filtered through a pad of celite. The filtrate was again filtered using a millipore filter (0.22 μm). To this filtrate was added a solution of 1,1-cyclobutanedicarboxylic acid (0.45 g, 3.1 mmol) dissolved in 1N sodium hydroxide solution (6.2 ml). The mixture was heated at 60° C. for 16 hours, concentrated under a reduced pressure to 10 ml and the resulting white powder was filtered to give 0.858 g of cis-cyclobutane-1,1-dicarboxylato[(4S,5S)-4,5-bis(aminomethyl)-1,3-dioxolane-2-spiro-1'-cyclohexane]platinum(II).

Yield: 52% Elemental analysis:

Calcd. for C$_{16}$H$_{26}$N$_2$O$_6$Pt: C 35.76, H 4.88, N 5.21 (%) Found: C 35.62, H 4.56, N 5.13 (%) FAB-MS: (M+H)$^+$=537($^{194}$Pt, 33%), 538($^{195}$Pt, 34%) and 539($^{196}$Pt, 25%)

The dihalogenodiamine platinum(II) complexes used as starting materials in the above Examples were synthesized in accordance with the following Preparative Examples, which are presented here for illustration purpose and not to limit the scope of the present invention.

Preparative Example 1

(1) Synthesis of 2,3-O-methylene-D-threitol 1,4-bis(methanesulfonate)

D-threitol 1,4-bis(methanesulfonate) was reacted with formaldehyde and concentrated sulfuric acid as described in J. Med. Chem., 7, 14 (1964) to yield 2,3-O-methylene-D-threitol 1,4-bis(methanesulfonate) in 61% yield.

(2) Synthesis of (4R,5R)-4,5-bis(azidomethyl)-1,3-dioxolane

A mixture of 2,3-O-methylene-D-threitol 1,4-bis(methanesulfonate) (3.19 g, 11.0 mmol) and sodium azide (2.86 g, 44.0 mmol) in anhydrous N,N-dimethylformamide (15 ml) was heated at 100° C. for 16 hours under a nitrogen atmosphere. The reaction mixture was cooled to a room temperature, diluted with water (20 ml) and extracted with ether (100 ml). The ethereal solution was washed with brine (20 ml), dried over anhydrous magnesium sulfate and evaporated to dryness under a reduced pressure. The crude product was purified by using flash column chromatography over silica gel with a mixture of ether-hexane (1:4, v/v) as the eluent to give 1.93 g of (4R,5R)-4,5-bis(azidomethyl)-1,3-dioxolane as a light yellow oil.

Yield: 95% $[\alpha]_D^{20} = +125.20°$ (acetone) IR(neat): 2103 cm$^{-1}$ (N$_3$) $^1$H NMR(CDCl$_3$): $\delta$3.30–3.62(m, 4H, 2 CH$_2$), 3.91–4.09(m, 2H, 2 CH), 5.08(s, 2H, OCH$_2$O) $^{13}$C NMR(CDCl$_3$): $\delta$51.64, 77.14, 95.37

(3) Synthesis of (4R,5R)-4,5-bis(aminomethyl)-1,3-dioxolane

A solution of (4R,5R)-4,5-bis(azidomethyl)-1,3-dioxolane (1.93 g, 10.5 mmol) in ethanol (20 ml) was hydrogenated in the presence of 10% palladium on activated carbon (0.2 g) at 50 psi at 40° C. for 2 hours. The reaction mixture was filtered through a pad of celite and evaporated to dryness under a reduced pressure to give 1.35 g of (4R,5R)-4,5-bis(aminomethyl)-1,3-dioxolane as a colorless oil.

Yield: 97% IR(neat): 3370, 3307 cm$^{-1}$ (NH$_2$) $^1$H NMR(CDCl$_3$): $\delta$1.40(s, 4H, 2 NH$_2$), 2.81–2.98(m, 4H, 2 CH$_2$), 3.63–3.82(m, 2H, 2 CH), 5.01(s, 2H, OCH$_2$O) $^{13}$C NMR(CDCl$_3$): $\delta$43.81, 80.34, 94.34

(4) Synthesis of cis-diiodo[(4R,5R)-4,5-bis(aminomethyl)-1,3-dioxolane]platinum(II)

To a stirred solution of potassium iodide (10.17 g, 61.2 mmol) in water (20 ml) was added a filtered solution of potassium tetrachloroplatinate(II) (4.24 g, 10.2 mmol) in water (150 ml) that was stirred at a room temperature for 40 minutes in the dark under a nitrogen atmosphere to obtain a black solution of potassium tetraiodoplatinate(II). 110 ml of water was placed in a flask and stirred at 60° C. under a nitrogen atmosphere, and into this, the above obtained black solution of potassium tetraiodoplatinate(II) and a solution of (4R,5R)-4,5-bis(aminomethyl)-1,3-dioxolane(1.35 g, 10.2 mmol) in water(170 ml) were simultaneously added dropwise over 2 hours at a constant rate. After 1 hour, the yellow precipitate was collected filtration, washed sequentially with water, ethanol and ether, and dried thoroughly in vacuo to give 4.95 g of cis-diiodo[(4R,5R)-4,5-bis(aminomethyl)-1,3-dioxolane]platinum(II).

Yield: 83%

Preparative Example 2

(1) Synthesis of 2,3-O-methylene-L-threitol 1,4-bis(methanesulfonate)

L-threitol 1,4-bis(methanesulfonate) was reacted with formaldehyde and concentrated sulfuric acid as described in J. Med. Chem., 7, 14 (1964) to yield 2,3-O-methylene-L-threitol 1,4-bis-(methanesulfonate) in 63% yield.

(2) Synthesis of (4S,5S)-4,5-bis(azidomethyl)-1,3-dioxolane 3.89 g of 2,3-O-methylene-L-threitol 1,4-bis(methanesulfonate) was reacted with sodium azide in the same manner as described in Preparative Example 1 to give 2.38 g of (4S, 5S)-4,5-bis(azidomethyl)-1,3-dioxolane.

Yield: 96% $[\alpha]_D^{20} = -122.01°$ (acetone)

(3) Synthesis of (4S,5S)-4,5-bis(aminomethyl)-1,3-dioxolane 1.10 g of (4S,5S)-4,5-bis(azidomethyl)-1,3-dioxolane was reduced in the same manner as described in Preparative Example 1 to give 0.78 g of (4S,5S)-4,5-bis-(aminomethyl)-1,3-dioxolane.

Yield: 99%

(4) Synthesis of cis-diiodo[(4S,5S)-4,5-bis(aminomethyl)-1,3-dioxolane]platinum(II)

0.78 g of (4S,5S)-4,5-bis(aminomethyl)-1,3-dioxolane was reacted with an aqueous solution of potassium tetraiodoplatinate (II) in the same manner as described in Preparative Example 1 to give 2.92 g of cis-diiodo[(4S,5S)-4,5-bis(aminomethyl)-1,3-dioxolane]-platinum(II).

Yield: 85%

Preparative Example 3

(1) Synthesis of 2,3-O-ethylidene-D-threitol 1,4-bis(methanesulfonate)

D-threitol 1,4-bis(methanesulfonate) was reacted with acetaldehyde diethyl acetal and methanesulfonic acid as described in J. Med. Chem., 7, 14 (1964) to yield 2,3-O-ethylidene-D-threitol 1,4-bis-(methanesulfonate) in 95% yield.

(2) Synthesis of (4R,5R)-4,5-bis(azidomethyl)-2-methyl-1,3-dioxolane 4.28 g of 2,3-O-ethylidene-D-threitol 1,4-bis(methanesulfonate) was reacted with sodium azide in the same manner as described in Preparative Example 1 to give 2.59 g of (4R, 5R)-4,5-bis(azidomethyl)-2-methyl-1,3-dioxolane as a light yellow oil.

Yield: 93% $[\alpha]_D^{20} = +143.80°$ (acetone) IR(neat): 2101 cm$^{-1}$ (N$_3$) $^1$H NMR(CDCl$_3$): $\delta$1.42(d, J=4.8 Hz, 3H, CH$_3$), 3.24–3.63 (m, 4H, 2 CH$_2$), 3.93–4.13(m, 2H, 2 CH), 5.24 (q, J=4.8 Hz, 1H, CH) $^{13}$C NMR(CDCl$_3$): $\delta$19.84, 51.76, 76.80, 77.96, 101.97

(3) Synthesis of (4R,5R)-4,5-bis(aminomethyl)-2-methyl-1,3-dioxolane 2.52 g of (4R,5R)-4,5-bis(aziodmethyl)-2-methyl-1,3-dioxolane was reduced in the same manner as described in Preparative Example 1 to give 1.80 g of (4R,5R)-4,5-bis(aminomethyl)-2-methyl-1,3-dioxolane as a semisolid oil.

Yield: 97% IR(neat): 3375, 3304 cm$^{-1}$ (NH$_2$) $^1$H NMR(CDCl$_3$): $\delta$1.37(d, J=4.8 Hz, 3H, CH$_3$), 1.41(s, 4H, 2 NH$_2$), 2.65–3.04(m, 4H, 2 CH$_2$), 3.65–3.87 (m, 2H, 2 CH), 5.16(q, J=4.8 Hz, 1H, CH) $^{13}$C NMR(CDCl$_3$): $\delta$19.75, 43.76, 44.05, 80.16, 81.09, 100.35

(4) Synthesis of cis-diiodo[(4R,5R)-4,5-bis(aminomethyl)-2-methyl-1,3-dioxolane]platinum(II)

1.70 g of (4R,5R)-4,5-bis(aminomethyl)-2-methyl-1,3-dioxolane was reacted with an aqueous solution of potassium tetraiodoplatinate(II) in the same manner as described in Preparative Example 1 to give 5.76 g of cis-diiodo[(4R, 5R)-4,5-bis(aminomethyl)-2-methyl-1,3-dioxolane]platinum(II) as a yellow solid.

Yield: 83%

Preparative Example 4

(1) Synthesis of 2,3-O-ethylidene-L-threitol 1,4-bis(methanesulfonate)

L-threitol 1,4-bis(methanesulfonate) was reacted with acetaldehyde diethyl acetal and methanesulfonic acid as described in J. Med. Chem., 7, 14 (1964) to yield 2,3,-O-ethylidene-L-threitol 1,4-bis-(methanesulfonate) in 96% yield.

(2) Synthesis of (4S,5S)-4,5-bis(azidomethyl)-2-methyl-1,3-dioxolane 4.99 g of 2,3-O-ethylidene-L-threitol 1,4-bis(methanesulfonate) was reacted with sodium azide in the same manner as described in Preparative Example 1 to give 3.18 g of (4S, 5S)-4,5-bis(azidomethyl)-2-methyl-1,3-dioxolane.

Yield: 98% $[\alpha]_D^{20} = -140.70°$ (acetone)

(3) Synthesis of (4S,5S)-4,5-bis(aminomethyl)-2-methyl-1,3-dioxolane 2.38 g of (4S,5S)-4,5-bis(aziodomethyl)-2-methyl-1,3-dioxolane was reduced in the same manner as described in Preparative Example 1 to give 1.75 g of (4S,5S)-4,5-bis(aminomethyl)-2-methyl-1,3-dioxolane.

Yield: 99%

(4) Synthesis of cis-diiodo[(4S,5S)-4,5-bis(aminomethyl)-2-methyl-1,3-dioxolane]platinum(II)

1.70 g of (4S,5S)-4,5-bis(aminomethyl)-2-methyl-1,3-dioxolane was reacted with an aqueous solution of potassium tetraiodoplatinate(II) in the same manner as described in Preparative Example 1 to give 5.80 g of cis-diiodo[(4S,5S)-4,5-bis(aminomethyl)-2-methyl-1,3-dioxolane]platinum(II).

Yield: 84%

Preparative Example 5

(1) Synthesis of 2,3-O-propionylidene-D-threitol 1,4-bis(methanesulfonate)

A mixture of D-threitol 1,4-bis(methanesulfonate)(1.80 g, 6.5 mmol), propionaldehyde(0.41 g, 7.1 mmol, 0.51 ml), anhydrous copper(II) sulfate(1.55 g, 9.7 mmol) and methanesulfonic acid(2 drops) in anhydrous toluene(30 ml) was stirred at a room temperature for 16 hours under a nitrogen atmosphere. Anhydrous potassium carbonate(0.3 g) was added to the reaction mixture and stirred for an additional 20 minutes. The reaction mixture was filtered, evaporated to dryness and oily residue was crystallized from a mixture of absolute ethanol and acetone to give 1.60 g of 2,3-O-propionylidene-D-threitol 1,4-bis(methanesulfonate) as colorless crystals.

Yield: 78% m.p.: 65.0°–65.5° C. IR(Nujol): 1357, 1179 cm$^{-1}$ (O—SO$_2$) $^1$H NMR(CDCl$_3$): $\delta$0.96(t, J=7.4 Hz, 3H, CH$_3$), 1.71(dq, J=4.6 Hz, J=7.4 Hz, 2H, CH$_2$), 3.09(s, 6H, 2 SO$_2$CH$_3$), 4.09–4.29(m, 2H, 2 CH), 4.33(m, 4H, 2 CH$_2$), 5.07(t, J=4.6 Hz, 1H, CH) $^{13}$C NMR(CDCl$_3$): $\delta$7.59, 26.89, 37.77, 67.78, 68.00, 75.18, 75.73, 106.38

Alternatively, 2,3-O-propionylidene-D-threitol 1,4-bis-(methansulfonate) may be prepared by the following method.

A mixture of D-tartaric acid(50.00 g, 0.333 mol) and concentrated sulfuric acid(5 ml) in absolute ethanol(500 ml) was heated at reflux for 15 hours. The reaction mixture was cooled to a room temperature and to it, aqueous 28% ammonium hydroxide solution(24 ml) was added, and the mixture was stirred for an additional 30 minutes. The white precipitate was filtered off and the filtrate was evaporated to dryness to give 56.09 g of diethyl D-tartrate as an oil.

Yield: 82% $^1$H NMR(CDCl$_3$): $\delta$1.33(t, J=7.2 Hz, 6H, 2 CH$_3$), 3.28 (br s, 2H, 2 OH), 4.32(q, J=7.2 Hz, 4H, 2 CH$_2$), 4.54(s, 2H, 2 CH) $^{13}$C NMR(CDCl$_3$): $\delta$14.07, 62.36, 71.95, 171.47

A mixture of diethyl D-tartrate(4.00 g, 19.4 mmol), propionaldehyde(5.63 g, 96.9 mmol, 6.99 ml), anhydrous copper(II) sulfate(6.19 g, 38.8 mmol) and methanesulfonic acid(3 drops) in anhydrous toluene(60 ml) was stirred at a room temperature for 16 hours under a nitrogen atmosphere. Anhydrous potassium carbonate(0.30 g) was added to the reaction mixture and stirred for an additional 20 minutes. The reaction mixture was filtered, evaporated to dryness and the oily residue was purified by using flash column chromatography over silica gel with a mixture of ether-hexane(1:4, v/v) as the eluent to give 3.80 g of diethyl 2,3-O-propionylidene-D-tartrate as an oil.

Yield: 80% IR(neat): 1757, 1740 cm$^{-1}$ (C=O) $^1$H NMR(CDCl$_3$): $\delta$1.01(t, J=7.5 Hz, 3H, CH$_3$), 1.32(t, J=7.2 Hz, 6H, 2 CH$_3$), 1.81(dq, J=4.5 Hz, J=7.5 Hz, 2H, CH$_2$), 4.27(q, J=7.2 Hz, 2H, CH$_2$), 4.28(q, J=7.2 Hz, 2H, CH$_2$), 4.66(d, J=4.2 Hz, 1H, CH), 4.75(d, J=4.2 Hz, 1H, CH), 5.23(t, J=4.5 Hz, 1H, CH) $^{13}$C NMR(CDCl$_3$): $\delta$7.59, 14.04, 14.07, 26.64, 61.77, 61.79, 77.13, 77.25, 108.39, 169.09, 169.78

A suspension of lithium aluminum hydride(1.03 g, 27.2 mmol) in ether(25 ml) was refluxed for 30 minutes with vigorous stirring. A solution of diethyl 2,3-O-propionylidene-D-tartrate(5.28 g, 21.4 mmol) in ether(10 ml) was added dropwise without heating over 30 minutes, the heat of reaction causing a gentle refluxing. After additional heating for 5 hours, ethyl acetate(1.1 ml) was carefully added, and the reaction mixture was cooled to 0°–5° C. After successive cautious additions of water (0.9 ml), 4N NaOH(0.9 ml) and water(2.8 ml), the inorganic precipitate which had formed was removed by filtration, and extracted thoroughly with warm ethyl acetate(2×40 ml). The combined organic solution were dried over anhydrous MgSO$_4$, evaporated to dryness and purified by using flash column chromatography over silica gel with a mixture of ethyl acetate and hexane (2:1, v/v) as the eluent to give 2.28 g of 2,3-O-propionylidene-D-threitol as an oil.

Yield: 66% IR(neat): 3385 cm$^{-1}$ (OH) $^1$H NMR(CDCl$_3$): $\delta$0.98(t, J=7.5 Hz, 3H, CH$_3$), 1.70(dq, J=4.5 Hz, J=7.5 Hz, 2H, CH$_2$), 3.34(br s, 2H, 2 OH), 3.62–3.88(m, 4H, 2 CH$_2$), 3.88–4.05(m, 2H, 2 CH), 5.05(t, J=4.5 Hz, 1H, CH) $^{13}$C NMR(CDCl$_3$): $\delta$7.75, 27.13, 62.36, 62.46, 78.29, 79.04, 105.63

To a stirred solution of 2,3-O-propionylidene-D-threitol (2.18 g, 13.4 mmol) in pyridine(10 ml) was added methanesulfonyl chloride(3.80 g, 33.2 mmol, 2.57 ml) dropwise at 0° C. and the mixture was stirred for 16 hours at a room temperature. The reaction mixture was poured into ice-water(20 ml) with vigorous stirring. The resulting precipitate was filtered, washed well with water and dried in vacuo. The crude product was crystallized from absolute ethanol to give 2.81 g of 2,3-O-propionylidene-D-threitol 1,4-bis(methanesulfonate).

Yield: 66% m.p.: 65.0°–65.5° C. IR(nujol): 1357, 1179 cm$^{-1}$(O—SO$_2$)

(2) Synthesis of (4R,5R)-4,5-bis(azidomethyl)-2-ethyl-1,3-dioxolane 1.43 g of 2,3-O-propionylidene-D-threitol 1,4-bis(methanesulfonate) was reacted with sodium azide in the same manner as described in Preparative Example 1 to give 0.88 g of (4R,5R)-4,5-bis(azidomethyl)-2-ethyl-1,3-dioxolane as a light yellow oil.

Yield: 92% $[\alpha]_D^{20}$=+127.88° (acetone) IR(neat): 2102 cm$^{-1}$ (N$_3$) $^1$H NMR(CDCl$_3$): δ0.98(t, J=7.5 Hz, 3H, CH$_3$), 1.72(dq, J=4.5 Hz, J=7.5 Hz, 2H, CH$_2$), 3.34–3.54 (m, 4H, 2 CH$_2$), 3.97–4.07(m, 2H, 2 CH), 5.07 (t, J=4.5 Hz, 1H, CH) $^{13}$C NMR(CDCl$_3$): δ7.64, 27.09, 51.88, 51.94, 77.94, 105.86

(3) Synthesis of (4R,5R)-4,5-bis(aminomethyl)-2-ethyl-1,3-dioxolane 0.85 g of (4R,5R)-4,5-bis(azidomethyl)-2-ethyl-1,3-dioxolane was reduced in the same manner as described in Preparative Example 1 to give 0.61 g of (4R,5R)-4,5-bis(aminomethyl)-2-ethyl-1,3-dioxolane as a semi-solid oil.

Yield: 95% IR(neat): 3367 cm$^{-1}$ (NH$_2$) $^1$H NMR(CDCl$_3$): δ0.97(t, J=7.5 Hz, 3H, CH$_3$), 1.36(s, 4H, 2 NH$_2$, 1.68(dq, J=4.5 Hz, J=7.5 Hz, 2H, CH$_2$), 2.75–3.00(m, 4H, 2 CH$_2$), 3.70–3.80(m, 2H, 2 CH), 5.00(t, J=4.5 Hz, 1H, CH) $^{13}$C NMR(CDCl$_3$): δ7.83, 27.19, 44.05, 44.33, 80.34, 81.11, 104.59

(4) Synthesis of cis-diiodo[(4R,5R)-4,5-bis(aminomethyl)-2-ethyl-1,3-dioxolane]platinum(II)

0.59 g of (4R,5R)-4,5-bis(aminomethyl)-2-ethyl-1,3-dioxolane was reacted with an aqueous solution of potassium tetraiodoplatinate(II) in the same manner as described in Preparative Example 1 to give 1.93 g of cis-diiodo[(4R,5R)-4,5-bis(aminomethyl)-2-ethyl-1,3-dioxolane]platinum(II) as a yellow solid.

Yield: 86%

Preparative Example 6

(1) Synthesis of 2,3-O-propionylidene-L-threitol 1,4-bis(methanesulfonate)

A mixture of L-threitol 1,4-bis(methanesulfonate)(4.00 g, 14.4 mmol), propionaldehyde diethyl acetal(19.00 g, 144.0 mmol, 23.3 ml) and methanesulfonic acid(2 drops) was heated at 70° C. for 16 hours under a nitrogen atmosphere. The reaction mixture was cooled to 0° C. with an ice bath and diluted with ether(100 ml). After standing for 1 hour at 0° C., the ethereal solution was decanted and the residue was washed with a small volume of ether and then triturated with a small volume of absolute ethanol to give 3.80 g of 2,3-O-propionylidene-L-threitol 1,4-bis(methanesulfonate) as colorless crystals.

Yield: 83%

(2) Synthesis of (4S,5S)-4,5-bis(azidomethyl)-2-ethyl-1,3-dioxolane 1.39 g of 2,3-O-propionylidene-L-threitol 1,4-bis(methanesulfonate) was reacted with sodium azide in the same manner as described in Preparative Example 1 to give 0.83 g of (4S,5S)-4,5-bis(azidomethyl)-2-ethyl-1,3-dioxolane.

Yield: 90% $[\alpha]_D^{20}$=−127.54° (acetone)

(3) Synthesis of (4S,5S)-4,5-bis(aminomethyl)-2-ethyl-1,3-dioxolane 0.73 g of (4S,5S)-4,5-bis(azidomethyl-2-ethyl-1,3-dioxolane was reduced in the same manner as described in Preparative Example 1 to give 0.51 g of (4S,5S)-4,5-bis(aminomethyl)-2-ethyl-1,3-dioxolane.

Yield: 93%

(4) Synthesis of cis-diiodo[(4S,5S)-4,5-bis(aminomethyl)-2-ethyl-1,3-dioxolane]platinum(II)

0.51 g of (4S,5S)-4,5-bis(aminomethyl)-2-ethyl-1,3-dioxolane was reacted with an aqueous solution of potassium tetraiodoplatinate(II) in the same manner as described in Preparative Example 1 to give 1.63 g of cis-diiodo[(4S,5S)-4,5-bis(aminomethyl)-2-ethyl-1,3-dioxolane]platinum(II).

Yield: 84%

Preparative Example 7

(1) Synthesis of 2,3-O-isopropylidene-D-threitol 1,4-bis(methanesulfonate)

5.04 g of 2,3-O-isopropylidene-D-threitol 1,4-bis(methanesulfonate) was produced in the same procedure as described in J. Med. Chem., 7, 14 (1964).

(2) Synthesis of (4R,5R)-4,5-bis(azidomethyl)-2,2-dimethyl-1,3-dioxolane 5.04 g of 2,3-O-isopropylidene-D-threitol 1,4-bis(methanesulfonate) was reacted with sodium azide in the same manner as described in Preparative Example 1 to give 3.22 g of (4R,5R)-4,5-bis(azidomethyl)-2,2-dimethyl-1,3-dioxolane as a light yellow oil.

Yield: 96% IR(neat): 2110 cm$^{-1}$ (N$_3$)

(3) Synthesis of (4R,5R)-4,5-bis(aminomethyl)-2,2-dimethyl-1,3-dioxolane 3.22 g of (4R,5R)-4,5-bis(azidomethyl)-2,2-dimethyl-1,3-dioxolane was reduced in the same manner as described in Preparative Example 1 to give 2.40 g of (4R,5R)-4,5-bis(aminomethyl)-2,2-dimethyl-1,3-dioxolane as an oil.

Yield: 99% IR(neat): 3370, 3306 cm$^{-1}$ (NH$_2$)

(4) Synthesis of cis-diiodo[(4R,5R)-4,5-bis(aminomethyl)-2,2-dimethyl-1,3-dioxolane]platinum(II)

2.40 g of (4R,5R)-4,5-bis(aminomethyl)-2,2-dimethyl-1,3-dioxolane was reacted with an aqueous solution of potassium tetraiodoplatinate(II) in the same manner as described in Preparative Example 1 to give 8.05 g of cis-diiodo[(4R,5R)-4,5-bis(aminomethyl)-2,2-dimethyl-1,3-dioxolane]platinum(II) as a yellow solid.

Yield: 88%

Preparative Example 8

(1) Synthesis of 2,3-O-isopropylidene-L-threitol 1,4-bis(methanesulfonate)

3.30 g of 2,3-O-isopropylidene-L-threitol 1,4-bis(methanesulfonate) was produced by the same procedure as described in J. Med. Chem., 7, 14 (1964).

(2) Synthesis of (4S,5S)-4,5-bis(azidomethyl)-2,2-dimethyl-1,3-dioxolane.

3.30 g of 2,3-O-isopropylidene-L-threitol 1,4-bis-(methanesulfonate) was reacted with sodium azide in the same manner as described in Preparative Example 1 to give 2.18 g of (4S,5S)-4,5-bis(azidomethyl)-2,2-dimethyl-1,3-dioxolane.

Yield: 99%

(3) Synthesis of (4S,5S)-4,5-bis(aminomethyl)-2,2-dimethyl-1,3-dioxolane 2.11 g of (4S,5S)-4,5-bis(azidomethyl)-2,2-dimethyl-1,3-dioxolane was reduced in the same manner as described in Preparative Example 1 to give 1.53 g of (4S,5S)-4,5-bis(aminomethyl)-2,2-dimethyl-1,3-dioxolane.

Yield: 96%

(4) Synthesis of cis-diiodo[(4S,5S)-4,5-bis(aminomethyl)-2,2-dimethyl-1,3-dioxolane]platinum(II)

1.50 g of (4S,5S)-4,5-bis(aminomethyl)-2,2-dimethyl-1,3-dioxolane was reacted with an aqueous solution of potassium tetraiodoplatinate(II) in the same manner as described in Preparative Example 1 to give 4.83 g of cis-diiodo[(4S,5S)-4,5-bis(aminomethyl)-2,2-dimethyl-1,3-dioxolane]platinum(II).

Yield: 85%

Preparative Example 9

(1) Synthesis of 2,3-O-isobutylidene-D-threitol 1,4-bis(methanesulfonate)

A mixture of D-threitol 1,4-bis(methanesulfonate) (4.00 g, 14.4 mmol), isobutyraldehyde(1.14 g, 15.8 mmol) anhydrous copper (II) sulfate(3.44 g, 21.6 mmol) and methanesulfonic acid(2 drops) in anhydrous toluene(40 ml) was stirred at a room temperature for 16 hours under a nitrogen atmosphere. The reaction mixture turned to a solid mass and to it, ethyl acetate(50 ml) and anhydrous potassium carbonate(0.3 g) were added. The reaction mixture was stirred for an additional 20 minutes, filtered, evaporated to dryness under a reduced pressure, and purified by using flash column chromatography over silica gel with a mixture of ethyl acetatehexane(1:1, v/v) as the eluent to give 4.70 g of 2,3-O-isobutylidene-D-threitol 1,4-bis(methanesulfonate) which was crystallized from absolute ethanol.

Yield: 98% m.p.: 70.0°–70.5° C. IR(KBr): 1360, 1332, 1182 cm$^{-1}$ (O—SO$_2$) $^1$H NMR(CDCl$_3$): δ0.95(d, J=6.8 Hz, 6H, 2 CH$_3$), 1.82(m, 1H, CH), 3.08(s, 6H, 2 SO$_2$CH$_3$), 4.05–4.25(m, 2H, 2 CH$_2$), 4.25–4.45(m, 4H, 2 CH$_2$), 4.86(d, J=4.6 Hz, 1H, CH) $^{13}$C NMR(CDCl$_3$): δ16.50, 31.87, 37.75, 67.83, 67.91, 75.28, 75.66, 109.15

Alternatively, 2,3-O-isobutylidene-D-threitol 1,4-bis(methanesulfonate) may be prepared by the following method.

A mixture of diethyl D-tartrate(15.00 g, 72.7 mmol), isobutyraldehyde(26.23 g, 363.7 mmol, 33.04 ml), anhydrous copper (II) sulfate(23.22 g, 145.5 mmol) and methanesulfonic acid (10 drops) in anhydrous toluene(250 ml) was stirred at a room temperature for 16 hours under a nitrogen atmosphere. Anhydrous potassium carbonate(1.00 g) was added to the reaction mixture and stirred for an additional 20 minutes. The reaction mixture was filtered, evaporated to dryness and the oily residue was purified by using flash column chromatography over silica gel with a mixture of ether-hexane(1:4, v/v) as the eluent to give 15.95 g of diethyl 2,3-O-isobutylidene-D-tartrate as an oil.

Yield: 84% IR(neat): 1757 cm$^{-1}$ (C=O) $^1$H NMR(CDCl$_3$): δ1.00(d, J=6.9 Hz, 3H, CH$_3$), 1.01(d, J=6.9 Hz, 3H, CH$_3$), 1.32(t, J=7.2 Hz, 6H, 2 CH$_3$), 1.96(m, 1H, CH(CH$_3$)$_2$), 4.27(q, J=7.2 Hz, 2H, CH$_2$), 4.27(q, J=7.2 Hz, 2H, CH$_2$), 4.65(d, J=4.2 Hz, 1H, CH), 4.73(d, J=4.2 Hz, 1H, CH), 5.01(d, J=4.8 Hz, 1H, CH) $^{13}$C NMR(CDCl$_3$): δ13.99, 14.02, 16.50, 31.61, 61.66, 77.09, 77.21, 111.12, 169.02, 169.80

15.00 g(57.6 mmol) of diethyl 2,3-O-isobutylidene-D-tartrate was reduced in the same manner as described in Step 1 of Preparative Example 5 to give 6.89 g of 2,3-O-isobutylidene -D-threitol as an oil.

Yield: 68% IR(neat): 3382 cm$^{-1}$ (OH) $^1$H NMR(CDCl$_3$): δ0.95(d, J=6.9 Hz, 6H, 2 CH$_3$), 1.83(m, 1H, CH(CH$_3$)$_2$), 2.54(br s, 2H, 2 OH), 3.68–3.86(m, 4H, 2 CH$_2$), 3.87–4.00(m, 2H, 2 CH), 4.84(d, J=4.5 Hz, 1H, CH) $^{13}$C NMR(CDCl$_3$): δ16.62, 16.67, 32.12, 62.27, 62.33, 78.11, 78.89, 108.24

6.70 g(38.0 mmol) of 2,3-O-isobutylidene-D-threitol was reacted with methanesulfonyl chloride in the same manner as described in Step 1 of Preparative Example 5 to give 11.13 g of 2,3-O-isobutylidene-D-threitol 1,4-bis(methanesulfonate).

Yield: 88% m.p.: 70.0°–70.5° C. IR(KBr): 1360, 1332, 1182 cm$^{-1}$ (O—SO$_2$)

(2) Synthesis of (4R,5R)-4,5-bis(azidomethyl)-2-isopropyl-1,3-dioxolane 4.40 g of 2,3-O-isobutylidene-D-threitol 1,4-bis(methanesulfonate) was reacted with sodium azide in the same manner as described in Preparative Example 1 to give 2.92 g of (4R,5R)-4,5-bis(azidomethyl)-2-isopropyl-1,3-dioxolane as a light yellow oil.

Yield: 97% [α]$_D^{20}$=+110.85° (acetone) IR(neat): 2103 cm$^{-1}$ (N$_3$) $^1$H NMR(CDCl$_3$): δ0.97(d, J=6.8 Hz, 6H, 2 CH$_3$), 1.65–2.05(m, 1H, CH), 3.20–3.60(m, 4H, 2 CH$_2$), 3.85–4.15(m, 2H, 2 CH), 4.85(d, J=4.6 Hz, 1H, CH) $^{13}$C NMR(CDCl$_3$): δ16.51, 16.56, 32.00, 51.81, 51.91, 77.10, 77.90, 108.69

(3) Synthesis of (4R,5R)-4,5-bis(aminomethyl)-2-isopropyl-1,3-dioxolane 2.87 g of (4R,5R)-4,5-bis(azidomethyl)-2-isopropyl-1,3-dioxolane was reduced in the same manner as described in Preparative Example 1 to give 2.13 g of (4R,5R)-4,5-bis(aminomethyl)-2-isopropyl-1,3-dioxolane as an oil.

Yield: 96% IR(neat): 3369, 3301 cm$^{-1}$ (NH$_2$) $^1$H NMR(CDCl$_3$): δ0.96(d, J=6.9 Hz, 6H, 2 CH$_3$), 1.33(s, 4H, 2 NH$_2$), 1.75–1.90(m, 1H, CH), 2.75–2.98(m, 4H, 2 CH$_2$), 3.67–3.77(m, 2H, 2 CH), 4.79(d, J=4.5 Hz, 1H, CH) $^{13}$C NMR(CDCl$_3$): δ16.65, 16.76, 32.06, 44.01, 44.25, 80.29, 80.91, 107.40

(4) Synthesis of cis-diiodo[(4R,5R)-4,5-bis(aminomethyl)-2-isopropyl-1,3-dioxolane]platinum(II)

0.70 g of (4R,5R)-4,5-bis(aminomethyl)-2-isopropyl-1,3-dioxolane was reacted with an aqueous solution of potassium tetraiodoplatinate(II) in the same manner as described in Preparative Example 1 to give 2.21 g of cis-diiodo[(4R, 5R)-4,5-bis(aminomethyl)-2-isopropyl-1,3-dioxolane]platinum(II) as a yellow solid.

Yield: 88%

Preparative Example 10

(1) Synthesis of 2,3-O-isobutylidene-L-threitol 1,4-bis(methanesulfonate)

4.00 g of L-threitol 1,4-bis(methanesulfonate) was reacted with isobutyraldehyde in the same manner as described in Preparative Example 9 to give 4.58 g of 2,3-O-isobutylidene-L-threitol 1,4-bis(methanesulfonate).

Yield: 96%

(2) Synthesis of (4S,5S)-4,5-bis(azidomethyl)-2-isopropyl-1,3-dioxolane 4.40 g of 2,3-O-isobutylidene-L-threitol 1,4-bis(methanesulfonate) was reacted with sodium azide in the same manner as described in Preparative Example 1 to give 2.90 g of (4S,5S)-4,5-bis(azidomethyl)-2-isopropyl-1,3-dioxolane.

Yield: 97% [α]$_D^{20}$=−110.91° (acetone)

(3) Synthesis of (4S,5S)-4,5-bis(aminomethyl)-2-isopropyl-1,3-dioxolane 2.50 g of (4S,5S)-4,5-bis(azidomethyl)-2-isopropyl-1,3-dioxolane was reduced in the same manner as described in Preparative Example 1 to give 1.85 g of (4S,5S)-4,5-bis(aminomethyl)-2-isopropyl-1,3-dioxolane.

Yield: 96%

(4) Synthesis of cis-diiodo[(4S,5S)-4,5-bis(aminomethyl)-2-isopropyl-1,3-dioxolane]platinum(II)

1.80 g of (4S,5S)-4,5-bis(aminomethyl)-2-isopropyl-1,3-doixolane was reacted with an aqueous solution of potassium tetraiodoplatinate(II) in the same manner as described in Preparative Example 1 to give 5.10 g of cis-diiodo[(4S,5S)-4,5-bis-(aminomethyl)-2-isopropyl-1,3-dioxolane]platinum(II).

Yield: 79%

Preparative Example 11

(1) Synthesis of 2,3-O-cyclopentylidene-D-threitol 1,4-bis(methanesulfonate)

A mixture of D-threitol 1,4-bis(methanesulfonate)(10.00 g, 35.9 mmol), cyclopentanone(6.05 g, 71.8 mmol, 6.4 ml) and methanesulfonic acid(5 drops) in benzene(100 ml) was refluxed under a Dean-Stark continuous water separator for 16 hours. The reaction mixture was cooled to a room temperature and to this clear solution, anhydrous potassium carbonate(0.50 g) was added. The reaction mixture was stirred for an additional 20 minutes, filtered, evaporated under a reduced pressure, and the residue was crystallized from absolute ethanol to give 11.02 g of 2,3-O-cyclopentylidene-D-threitol 1,4-bis(methanesulfonate) as white crystals.

Yield: 89% m.p.: 89.5°–90.5° C. IR(Nujol): 1357, 1179 cm$^{-1}$ (O—SO$_2$) $^1$H NNR(CDCl$_3$): $\delta$1.50–2.00(m, 8H, 4 CH$_2$), 3.08(s, 6H, 2 SO$_2$CH$_3$), 4.10–4.25(m, 2H, 2 CH), 4.25–4.50(m, 4H, 2 CH$_2$) $^{13}$C NMR(CDCl$_3$): $\delta$23.35, 37.15, 37.66, 68.03, 75.10, 120.80

Alternatively, 2,3-O-cyclopentylidene-D-threitol 1,4-bis(methanesulfonate) may prepared by the following method.

A mixture of diethyl D-tartrate(3.90 g, 18.9 mmol), cyclopentanone(6.53 g, 77.6 mmol, 6.86 ml) and methanesulfonic acid(3 drops) in benzene(60 ml) was refluxed under a Dean-Stark continuous water separator for 16 hours. The reaction mixture was cooled to a room temperature and to this clear solution, anhydrous potassium carbonate(0.30 g) was added. The reaction mixture was stirred for an additional 20 minutes, filtered, evaporated to dryness, and the residue was purified by using flash column chromatography over silica gel with a mixture of ether-hexane(1:4, v/v) as the eluent to give 2.36 g of diethyl 2,3-O-cyclopentylidene -D-tartrate as an oil.

Yield: 46% IR(neat): 1757 cm$^{-1}$ (C=O) $^1$H NMR(CDCl$_3$): $\delta$1.32(t, J=7.2 Hz, 6H, 2 CH$_3$), 1.71(m, 4H, cyclopentyl), 1.80–2.10(m, 4H, cyclopentyl), 4.27(q, J=7.2 Hz, 4H, 2 CH$_2$), 4.72(s, 2H, 2 CH) $^{13}$C NMR(CDCl$_3$): $\delta$14.04, 23.38, 36.55, 61.73, 76.99, 123.26, 169.53

6.12 g(22.5 mmol) of diethyl 2,3-O-cyclopentylidene-D -tartrate was reduced by the same manner as described in Step 1 of Preparative Example 5 to give 2.57 g of 2,3-O-cyclopentylidene -D-threitol as white crystals.

Yield: 61% m.p.: 53.0°–53.5° C. IR(KBr): 3283 cm$^{-1}$ (OH) $^1$H NMR(CDCl$_3$): $\delta$1.51–2.01(m, 8H, cyclopentyl), 2.56(br s, 2H, 2 OH), 3.61–3.87(m, 4H, 2 CH$_2$), 3.93 (br s, 2H, 2 CH) $^{13}$C NMR(CDCl$_3$): $\delta$23.42, 37.36, 62.42, 78.52, 119.34 2.50 g (13.3 mmol) of 2,3-O-cyclopentylidene-D-threitol was reacted with methanesulfonyl chloride in the same manner as described in Step 1 of Preparative Example 5 to give 3.72 g of 2,3-O-cyclopentylidene-D-threitol 1,4-bis(methanesulfonate).

Yield: 81% m.p.: 89.5°–90.5° C. IR(Nujol): 1357, 1179 cm$^{-1}$ (O—SO$_2$)

(2) Synthesis of (4R,5R)-4,5-bis(azidomethyl)-1,3-dioxolane-2-spiro-1'-cyclopentane 5.00 g of 2,3-O-cyclopentylidene-D-threitol 1,4-bis(methanesulfonate) was reacted with sodium azide in the same manner as described in Preparative Example 1 to give 3.29 g of (4R,5R)-4,5-bis(azidomethyl)-1,3-dioxolane-2-spiro-1'-cyclopentane as a light yellow oil.

Yield: 95% [$\alpha$]$_D^{20}$= +125.39° (acetone) IR(neat): 2101 cm$^{-1}$ (N$_3$) $^1$H NMR(CDCl$_3$): $\delta$1.50–2.05(m, 8H, 4 CH$_2$), 3.25–3.60(m, 4H, 2 CH$_2$), 3.89–4.09(m, 2H, 2 CH), $^{13}$C NMR(CDCl$_3$): $\delta$23.25, 37.07, 51.73, 76.83, 120.15

(3) Synthesis of (4R,5R)-4,5-bis(aminomethyl)-1,3-dioxolane-2-spiro-1'-cyclopentane 3.20 g of (4R,5R)-4,5-bis(azidomethyl)-1,3-dioxolane-2-spiro-1'-cyclopentane was reduced in the same manner as described in Preparative Example 1 to give 2.40 g of (4R,5R)-4,5-bis(aminomethyl)-1,3-dioxolane-2-spiro-1'-cyclopentane as an oil.

Yield: 96% IR(neat): 3370, 3302 cm$^{-1}$ (NH$_2$) $^1$H NMR(CDCl$_3$): $\delta$1.36(s, 4H, 2 NH$_2$), 1.50–1.90(m, 8H, 4 CH$_2$), 2.77–2.95(m, 4H, 2 CH$_2$), 3.68–3.78 (m, 2H, 2 CH), $^{13}$C NMR(CDCl$_3$): $\delta$23.23, 37.30, 44.13, 80.02, 118.45

(4) Synthesis of cis-diiodo[(4R,5R)-4,5-bis(aminomethyl)-1,3-dioxolane-2-spiro-1'-cyclopentane]platinum-(II)

1.26 g of (4R,5R)-4,5-bis(aminomethyl)-1,3-dioxolane-2-spiro-1'-cyclopentane was reacted with an aqueous solution of potassium tetraiodoplatinate(II) in the same manner as described in Preparative Example 1 to give 3.87 g of cis-diiodo[(4R,5R)-4,5-bis(aminomethyl))-1,3-dioxolane-2-spiro-1'-cyclopentane]platinum(II) as a yellow solid.

Yield: 90%

Preparative Example 12

(1) Synthesis of 2,3-O-cyclopentylidene-L-threitol 1,4-bis(methanesulfonate)

5.00 g of L-threitol 1,4-bis(methanesulfonate) was reacted with cyclopentanone in the same procedure as described in Preparative Example 11 to give 5.93 g of 2,3-O-cyclopentylidene-L-threitol 1,4-bis(methanesulfonate).

Yield: 96% m.p.: 90°–91° C.

(2) Synthesis of (4S,5S)-4,5-bis(azidomethyl)-1,3-dioxolane-2-spiro-1'-cyclopentane 5.73 g of 2,3-O-cyclopentylidene-L-threitol 1,4-bis(methanesulfo) was reacted with sodium azide in the same manner as described in Preparative Example 1 to give 3.85 g of (4S,5S)-4,5-bis(azidomethyl)-1,3-dioxolane-2-spiro-1'-cyclopentane.

Yield: 97% [$\alpha$]$_D^{20}$= -122.90° (acetone)

(3) Synthesis of (4S,5S)-4,5-bis(aminomethyl)-1,3-dioxolane-2-spiro-1'-cyclopentane 2.86 g of (4S,5S)-4,5-bis(azidomethyl)-1,3-dioxolane-2-spiro-1'-cyclopentane was reduced in the same manner as described in Preparative Example 1 to give 2.12 g of (4S,5S)-4,5-bis(aminomethyl)-1,3-dioxolane-2-spiro-1'-cyclopentane.

Yield: 95%

(4) Synthesis of cis-diiodo[(4S,5S)-4,5-bis(aminomethyl)-1,3-dioxolane-2-spiro-1'-cyclopentane]platinum-(II)

2.00 g of (4S,5S)-4,5-bis(aminomethyl)-1,3-dioxolane-2-spiro-1'-cyclopentane was reacted with an aqueous solution of potassium tetraiodoplatinate(II) in the same manner as described in Preparative Example 1 to give 6.00 g of cis-diiodo[(4S,5S)-4,5-bis(aminomethyl)-1,3-dioxolane-2-spiro-1'-cyclopentane]platinum(II).

Yield: 88%

Preparative Example 13

(1) Synthesis of 2,3-O-cyclohexylidene-D-threitol 1,4-bis(methanesulfonate)

4.00 g(14.4 mmol) of D-threitol 1,4-bis(methanesulfonate) was reacted with cyclohexanone(2.82 g, 28.7 mmol, 2.98 ml) in the same manner as described in Preparative Example 11 to give 4.73 g of 2,3-O-cyclohexylidene-D-threitol 1,4-bis(methanesulfonate) as white crystals.

Yield: 92% m.p. 95.5°~96.5° C.

Alternatively, 2,3-O-cyclohexylidene-D-threitol 1,4-bis(methanesulfonate) may be prepared by the following method.

A mixture of diethyl D-tartrate(3.90 g, 18.9 mmol), cyclohexanone(7.62 g, 77.6 mmol, 8.04 ml) and methanesulfonic acid(3 drops) in toluene(60 ml) was refluxed under a Dean-Stark continuous water separator for 16 hours. The reaction mixture was cooled to a room temperature and to this clear solution, anhydrous potassium carbonate(0.30 g) was added. The reaction mixture was stirred for an additional 20 minutes, filtered, evaporated to dryness, and the residue was purified by using flash column chromatography over silica gel with a mixture of ether-hexane(1:4, v/v) as the eluent to give 4.74 g of diethyl 2,3-O-cyclohexylidene-D-tartrate as an oil.

Yield: 88% IR(neat): 1757, 1735 cm$^{-1}$ (C=O) $^1$H NMR(CDCl$_3$): δ1.31(t, J=7.2 Hz, 6H, 2 CH$_3$), 1.37–1.47 (m, 2H, cyclohexyl), 1.57–1.80(m, 8H, cyclohexyl), 4.27(q, J=7.2 Hz, 4H, 2 CH$_2$), 4.77(s, 2H, 2 CH) $^{13}$C NMR(CDCl$_3$): δ13.98, 23.65, 24.78, 35.77, 61.63, 76.83, 114.40, 169.78

6.58 g(23.0 mmol) of diethyl 2,3-O-cyclohexylidene-D-tartrate was reduced in the same manner as described in Step 1 of Preparative Example 5 to give 2.98 g of 2,3-O-cyclohexylidene-D-threitol as colorless crystals.

Yield: 64% m.p.: 49.5°–51.5° C. IR(KBr): 3383 cm$^{-1}$ (OH) $^1$H NMR(CDCl$_3$): δ1.34–1.49(m, 2H, cyclohexyl), 1.63(br s, 8H, cyclohexyl), 2.35(br s, 2H, 2 OH), 3.64–3.86(m, 4H, 2 CH$_2$), 3.99(br s, 2H, 2 CH)

2.70 g(13.3 mmol) of 2,3-O-cyclohexylidene-D-threitol was reacted with methanesulfonyl chloride in the same manner as described in Step 1 of Preparative Example 5 to give 4.29 g of 2,3-O-cyclohexylidene-D-threitol 1,4-bis(methanesulfonate).

Yield: 90% m.p.: 95.5°–96.5° C.

(2) Synthesis of (4R,5R)-4,5-bis(azidomethyl)-1,3-dioxolane-2-spiro-1'-cyclohexane 4.73 g of 2,3-O-cyclohexylidene-D-threitol 1,4-bis(methanesulfonate) was reacted with sodium azide in the same manner as described in Preparative Example 1 to give 3.16 g of (4R,5R)-4,5-bis(azidomethyl)-1,3-dioxolane-2-spiro-1'-cyclohexane as a light yellow oil.

Yield: 95% [α]$_D^{20}$=+120.36° (acetone) IR(neat): 2100 cm$^{-1}$ (N$_3$) $^1$H NMR(CDCl$_3$): δ1.20–1.85(m, 10H, 5 CH$_2$), 3.21–3.62(m, 4H, 2 CH$_2$), 3.95–4.15(m, 2H, 2 CH), $^{13}$C NMR(CDCl$_3$): δ23.77, 24.93, 36.45, 51.70, 76.60, 110.99

(3) Synthesis of (4R,5R)-4,5-bis(aminomethyl)-1,3-dioxolane-2-spiro-1'-cyclohexane 3.10 g of (4R,5R)-4,5-bis(azidomethyl)-1,3-dioxolane-2-spiro-1'-cyclohexane was reduced in the same manner as described in Preparative Example 1 to give 2.44 g of (4R,5R)-4,5-bis(aminomethyl)-1,3-dioxolane-2-spiro-1'-cyclohexane as an oil.

Yield: 99% IR(neat): 3370, 3297 cm$^{-1}$ (NH$_2$) $^1$H NMR(CDCl$_3$): δ1.37(s, 4H, 2 NH$_2$), 1.40–1.80(m, 10H, 5 CH$_2$), 2.78–2.93(m, 4H, 2 CH$_2$), 3.70–3.80 (m, 2H, 2 CH) $^{13}$C NMR(CDCl$_3$): δ23.71, 25.00, 36.74, 44.20, 79.55, 109.06

(4) Synthesis of cis-diiodo[(4R,5R)-4,5-bis(aminomethyl)-1,3-dioxolane-2-spiro-1'-cyclohexane]platinum(II)

0.70 g of (4R,5R)-4,5-bis(aminomethyl)-1,3-dioxolane-2-spiro-1'-cyclohexane was reacted with an aqueous solution of potassium tetraiodoplatinate(II) in the same manner as described in Example 1 to give 2.00 g of cis-diiodo[(4R,5R)-4,5-bis(aminomethyl)-1,3-dioxolane-2-spiro-1'-cyclohexane]platinum(II) as a yellow solid.

Yield: 88%

Preparative Example 14

(1) Synthesis of 2,3-O-cyclohexylidene-L-threitol 1,4-bis(methanesulfonate)

5.00 g(18.0 mmol) of L-threitol 1,4-bis(methanesulfonate) was reacted with cyclohexanone(3.53 g, 35.9 mmol, 3.72 ml) in the same manner as described in Preparative Example 11 to give 6.14 g of 2,3-O-cyclohexylidene-L-threitol 1,4-bis(methanesulfonate) as white crystals.

Yield: 95%

(2) Synthesis of (4S,5S)-4,5-bis(azidomethyl)-1,3-dioxolane-2-spiro-1'-cyclohexane 5.94 g of 2,3-O-cyclohexylidene-L-threitol 1,4-bis(methanesulfonate) was reacted with sodium azide in the same manner as described in Preparative Example 1 to give 4.11 g of (4S,5S)-4,5-bis(azidomethyl)-1,3-dioxolane-2-spiro-1'-cyclohexane.

Yield: 98% [α]$_D^{20}$=−122.51° (acetone)

(3) Synthesis of (4S,5S)-4,5-bis(aminomethyl)-1,3-dioxolane-2-spiro-1'-cyclohexane 3.03 g of (4S,5S)-4,5-bis(azidomethyl)-1,3-dioxolane-2-spiro-1'-cyclohexane was reduced in the same manner as described in Preparative Example 1 to give 2.35 g of (4S,5S)-4,5-bis(aminomethyl)-1,3-dioxolane-2-spiro-1'-cyclohexane.

Yield: 98%

(4) Synthesis of cis-diiodo[(4S,5S)-4,5-bis(aminomethyl)-1,3-dioxolane-2-spiro-1'-cyclohexane]platinum(II)

2.30 g of (4S,5S)-4,5-bis(aminomethyl)-1,3-dioxolane-2-spiro-1'-cyclohexane was reacted with an aqueous solution of potassium tetraiodoplatinate(II) in the same manner as described in Preparative Example 1 to give 6.42 g of cis-diiodo[(4S,5S)-4,5-bis(aminomethyl)-1,3-dioxolane-2-spiro-1'-cyclohexane]platinum(II).

Yield: 86%

Preparative Example 15

(1) Synthesis of 2,3-O-diethylmethylene-D-threitol 1,4-bis(methanesulfonate)

A mixture of D-threitol 1,4-bis(methanesulfonate) (4.17 g, 15.0 mmol), 3-pentanone(2.58 g, 30.0 mmol, 3.17 ml) and methanesulfonic acid(3 drops) in benzene(50 ml) was refluxed under a Dean-Stark continuous water separator for 16 hours. The reaction mixture was cooled to a room temperature and to this clear solution, anhydrous potassium carbonate(0.20 g) was added. The reaction mixture was stirred for an additional 20 minutes, filtered, evaporated under a reduced pressure, and the residue was crystallized from absolute ethanol to give 4.32 g of 2,3-O-diethylmethylene-D-threitol 1,4-bis(methanesulfonate) as white crystals.

Yield: 83% m.p.: 53.5° C. IR(KBr): 1351, 1170 cm$^{-1}$ (O—SO$_2$) $^1$H NNR(CDCl$_3$): δ0.92(t, J=7.3 Hz, 6H, 2 CH$_3$), 1.68(q, J=7.3 Hz, 4H, 2 CH$_2$), 3.08(s, 6H, 2 SO$_2$CH$_3$), 4.08–4.22(m, 2H, 2 CH), 4.22–4.44(m, 4H, 2

CH$_2$) $^{13}$C NMR(CDCl$_3$): δ7.85, 30.17, 37.67, 67.85, 75.53, 114.85

(2) Synthesis of (4R,5R)-4,5-bis(azidomethyl)-2,2-diethyl-1,3-dioxolane 4.26 g(12.3 mmol) of 2,3-O-diethylmethylene-D-threitol 1,4-bis(methanesulfonate) was reacted with sodium azide in the same manner as described in Example 1 to give 2.65 g of (4R,5R)-4,5-bis(azidomethyl)-2,2-diethyl-1,3-dioxolane as a light yellow oil.

Yield: 90% [α]$_D^{20}$=+105.89° (acetone) IR(neat): 2104 cm$^{-1}$ (N$_3$) $^1$H NMR(CDCl$_3$): δ0.93(t, J=7.3 Hz, 6H, 2 CH$_3$), 1.70(q, J=7.3 Hz, 4H, 2 CH$_2$), 3.27–3.63(m, 4H, 2 CH$_2$), 3.89–4.10(m, 2H, 2 CH) $^{13}$C NMR(CDCl$_3$): δ7.91, 30.21, 51.75, 77.13, 114.16

(3) Synthesis of (4R,5R)-4,5-bis(aminomethyl)-2,2-diethyl-1,3-dioxolane 2.62 g(10.9 mmol) of (4R,5R)-4,5-bis(azidomethyl)-2,2-diethyl-1,3-dioxolane was reduced in the same manner as described in Preparative Example 1 to give 2.05 g of (4R,5R)-4,5-bis(aminomethyl)-2,2-diethyl-1,3-dioxolane as a colorless oil.

Yield: 100% IR(neat): 3374, 3299 cm$^{-1}$ (NH$_2$) $^1$H NMR(CDCl$_3$): δ0.91(t, J=7.3 Hz, 6H, 2 CH$_3$), 1.39(s, 4H, 2 NH$_2$), 1.65(q, J=7.3 Hz, 4H, 2 CH$_2$), 2.68–3.04(m, 4H, 2 CH$_2$), 3.60–3.87(m, 2H, 2 CH) $^{13}$C NMR(CDCl$_3$): δ8.01, 30.56, 44.24, 80.50, 112.41

(4) Synthesis of cis-diiodo[(4R,5R)-4,5-bis(aminomethyl)-2,2-diethyl-1,3-dioxolane]platinum(II)

2.05 g(10.9 mmol) of (4R,5R)-4,5-bis(aminomethyl)-2,2-diethyl-1,3-dioxolane was reacted with an aqueous solution of potassium tetraiodoplatinate(II) in the same manner as described in Example 1 to give 6.35 g of cis-diiodo[(4R,5R)-4,5-bis(aminomethyl)-2,2-diethyl-1,3-dioxolane]platinum(II) as a yellow solid.

Yield: 91%

Preparative Example 16

(1) Synthesis of 2,3-O-(1-methylpropylidene)-D-threitol 1,4-bis(methanesulfonate)

A mixture of D-threitol 1,4-bis(methanesulfonate)(3.50 g, 12.6 mmol), 2-butanone(70 ml), anhydrous copper(II) sulfate(3.01 g, 18.9 mmol) and concentrated sulfuric acid(0.1 ml) was stirred at room temperature for 16 hours under a nitrogen atmosphere. The reaction mixture was filtered and the filtrate was neutralized with 28% of ammonium hydroxide solution. The filtered solution was evaporated to dryness and crystallized from absolute ethanol to give 3.69 g of 2,3-O-(1-methylpropylidene)-D-threitol 1,4-bis(methanesulfonate) as white crystals.

Yield: 98% m.p.: 71.5°–72.5° C. IR(KBr): 1352, 1332, 1182 cm$^{-1}$ (O-SO$_2$) $^1$H NMR(CDCl$_3$): δ0.94(t, J=7.3 Hz, 3H, CH$_3$), 1.38(s, 3H, CH$_3$), 1.70(q, J=7.3 Hz, 2H, CH$_2$), 3.08(s, 6H, 2 SO$_2$CH$_3$), 4.02–4.27(m, 2H, 2 CH), 4.31–4.45(m, 4H, 2 CH$_2$) $^{13}$C NMR(CDCl$_3$): δ8.01, 24.59, 32.69, 37.70, 67.74, 67.97, 75.02, 75.60, 112.90

(2) Synthesis of (4R,5R)-4,5-bis(azidomethyl)-2-ethyl-2-methyl-1,3-dioxolane 3.50 g(11.7 mmol) of 2,3-O-(1-methylpropylidene)-D-threitol 1,4-bis(methanesulfonate) was reacted with sodium azide in the same manner as described in Preparative Example 1 to give 2.35 g of (4R,5R)-4,5-bis(azidomethyl)-2-ethyl-2-methyl-1,3-dioxolane as a light yellow oil.

Yield: 88% [α]$_D^{20}$=+128.24° (acetone) IR(neat): 2105 cm$^{-1}$ (N$_3$) $^1$H NMR(CDCl$_3$): δ0.96(t, J=7.3 Hz, 3H, CH$_3$), 1.41(s, 3H, CH$_3$), 1.73(q, J=7.3 Hz, 2H, CH$_2$), 3.23–3.65(m, 4H, 2 CH$_2$), 3.88–4.18(m, 2H, 2 CH) $^{13}$C NMR(CDCl$_3$): δ8.04, 24.53, 32.82, 51.61, 51.70, 76.65, 77.32, 112.28

(3) Synthesis of (4R,5R)-4,5-bis(aminomethyl)-2-ethyl-2-methyl-1,3-dioxolane 2.70 g(11.9 mmol) of (4R,5R)-4,5-bis(azidomethyl)-2-ethyl-2-methyl-1,3-dioxolane was reduced in the same manner as described in Preparative Example 1 to give 2.08 g of (4R,5R)-4,5-bis(aminomethyl)-2-ethyl-2-methyl-1,3-dioxolane as an oil.

Yield: 100% IR(neat): 3373, 3319 cm$^{-1}$ (NH$_2$) $^1$H NMR(CDCl$_3$): δ0.94(t, J=7.4 Hz, 3H, CH$_3$), 1.35(br s, 7H, CH$_3$ and 2 NH$_2$), 1.68(q, J=7.4 Hz, 2H, CH$_2$), 2.71–3.03(m, 4H, 2 CH$_2$), 3.63–3.93(m, 2H, 2 CH) $^{13}$C NMR(CDCl$_3$): δ8.10, 25.01, 33.01, 43.99, 44.24, 79.84, 80.55, 110.49

(4) Synthesis of cis-diiodo[(4R,5R)-4,5-bis(aminomethyl)-2-ethyl-2-methyl-1,3-dioxolane]platinum(II)

2.08 g(11.9 mmol) of (4R,5R)-4,5-bis(aminomethyl)-2-ethyl-2-methyl-1,3-dioxolane was reacted with an aqueous solution of potassium tetraiodoplatinate(II) in the same manner as described in Preparative Example 1 to give 7.12 g of cis-diiodo[(4R,5R)-4,5-bis(aminomethyl)-2-ethyl-2-methyl-1,3-dioxolane]platinum(II) as a yellow solid.

Yield: 96%

Preparative Example 17

(1) Synthesis of 2,3-O-butylidene-D-threitol 1,4-bis(methanesulfonate)

A mixture of D-threitol 1,4-bis(methanesulfonate)(3.50 g, 12.6 mmol), n-butyraldehyde(1.00 g, 13.8 mmol, 1.25 ml), anhydrous copper(II) sulfate(3.01 g, 18.9 mmol) and methanesulfonic acid (3 drops) in anhydrous toluene(35 ml) was stirred at a room temperature for 16 hours under a nitrogen atmosphere. The reaction mixture was added with anhydrous potassium carbonate(0.30 g) and stirred for an additional 20 minutes. The reaction mixture was filtered, evaporated to dryness and crystallized from absolute ethanol to give 4.10 g of 2,3-O-butylidene-D-threitol 1,4-bis(methanesulfonate) as white crystals.

Yield: 98% m.p.: 59.0°–59.5° C. IR(KBr): 1360, 1332, 1782 cm$^{-1}$ (O-SO$_2$) $^1$H NMR(CDCl$_3$): δ0.95(t, J=7.4 Hz, 3H, CH$_3$), 1.45(m, 2H, CH$_2$), 1.66(m, 2H, CH$_2$), 3.08(s, 6H, 2 SO$_2$CH$_3$), 4.10–4.27(m, 2H, 2 CH), 4.27–4.50(m, 4H, 2 CH$_2$), 5.10(t, J=4.6 Hz, 1H, CH) $^{13}$C NMR(CDCl$_3$): δ13.88, 17.02, 35.83, 37.74, 67.80, 68.06, 75.06, 75.69, 105.49

(2) Synthesis of (4R,5R)-4,5-bis(azidomethyl)-2-propyl-1,3-dioxolane 4.01 g(12.1 mmol) of 2,3-O-butylidene-D-threitol 1,4-bis(methanesulfonate) was reacted with sodium azide in the same manner as described in Preparative Example 1 to give 2.45 g of (4R,5R)-4,5-bis(azidomethyl)-2-propyl-1,3-dioxolane as a light yellow oil.

Yield: 90% [α]$_D^{20}$=119.96° (acetone) IR(neat): 2104 cm$^{-1}$ (N$_3$) $^1$H NMR(CDCl$_3$): δ0.96(t, J=7.4 Hz, 3H, CH$_3$), 1.46(m, 2H, CH$_2$), 1.67(m, 2H, CH$_2$), 3.30–3.60(m, 4H, 2 CH$_2$), 4.01(br s, 2H, 2 CH), 5.10 (t, J=4.5 Hz, 1H, CH) $^{13}$C NMR(CDCl$_3$): δ13.92, 17.11, 36.09, 51.87, 51.96, 76.89, 77.90, 105.02

(3) Synthesis of (4R,5R)-4,5-bis(aminomethyl)-2-propyl-1,3-dioxolane 2.37 g(10.5 mmol) of (4R,5R)-4,5-bis(azidomethyl)-2-propyl-1,3-dioxolane was reduced in the same manner as described in Preparative Example 1 to give 1.81 g of (4R,5R)-4,5-bis(aminomethyl)-2-propyl-1,3-dioxolane as an oil.

Yield: 99% IR(neat): 3368, 3297 cm$^{-1}$ (NH$_2$) $^1$H NMR(CDCl$_3$): δ0.95(t, J=7.2 Hz, 3H, CH$_3$), 1.45(m, 2H, CH$_2$), 1.63(m, 2H, CH$_2$), 1.68(s, 4H, 2 NH$_2$), 2.70–3.05(m, 4H, 2 CH$_2$), 3.75(br s, 2H, 2 CH), 5.03(t, J=4.2 Hz, 1H, CH) $^{13}$C NMR(CDCl$_3$): δ14.01, 17.23, 36.27, 43.94, 44.24, 80.15, 81.01, 103.71

(4) Synthesis of cis-diiodo[(4R,5R)-4,5-bis(aminomethyl)-2-propyl-1,3-dioxolane]platinum(II)

1.81 g(10.4 mmol) of (4R,5R)-4,5-bis(aminomethyl)-2-propyl-1,3-dioxolane was reacted with an aqueous solution of potassium tetraiodoplatinate(II) in the same manner as described in Preparative Example 1 to give 4.73 g of cis-diiodo[(4R,5R)-4,5-bis(aminomethyl)-2-propyl-1,3-dioxolane]platinum(II) as a yellow solid.

Yield: 87%

Preparative Example 18

(1) Synthesis of 2,3-O-isopentylidene-D-threitol 1,4-bis(methanesulfonate)

3.50 g(12.6 mmol) of D-threitol 1,4-bis(methanesulfonate) was reacted with isovaleraldehyde(1.19 g, 13.8 mmol, 1.48 ml) in the same manner as described in Preparative Example 17 to give 4.18 g of 2,3-O-isopentylidene-D-threitol 1,4-bis(methanesulfonate) as white crystals.

Yield: 96% m.p.: 85.5°–86° C. IR(KBr): 1356, 1333, 1181 cm$^{-1}$ (O—SO$_2$) $^1$H NMR(CDCl$_3$): δ0.95(d, J=6.6 Hz, 6H, 2 CH$_3$), 1.58(dd, J=4.9 Hz, J=6.8 Hz, 2H, CH$_2$), 1.79(m, 1H, CH), 3.09(s, 6H, 2 SO$_2$CH$_3$), 4.18(br s, 2H, 2 CH), 4.27–4.50(m, 4H, 2 CH$_2$ CH$_2$), 5.13(t, J=4.9 Hz, 1H, CH) $^{13}$C NMR(CDCl$_3$): δ22.82, 22.88, 24.38, 37.80, 42.67, 67.75, 68.05, 74.98, 75.73, 104.91

(2) Synthesis of (4R,5R)-4,5-bis(azidomethyl)-2-isobutyl-1,3-dioxolane 4.08 g of 2,3-O-isopentylidene-D-threitol 1,4-bis(methanesulfonate) was reacted with sodium azide in the same manner as described in Preparative Example 1 to give 2.78 g of (4R,5R)-4,5-bis(azidomethyl)-2-isobutyl-1,3-dioxolane as a light yellow oil.

Yield: 98% [α]$_D^{20}$=+118.44° (acetone) IR(neat): 2103 cm$^{-1}$ (N$_3$) $^1$H NMR(CDCl$_3$): δ0.96(d, J=6.6 Hz, 6H, 2 CH$_3$), 1.59(dd, J=5.1 Hz, J=6.6 Hz, 2H, CH$_2$), 1.83(m, 1H, CH), 3.30–3.60(m, 4H, 2 CH$_2$), 4.01 (br s, 2H, 2 CH), 5.13(t, J=5.1 Hz, 1H, CH) $^{13}$C NMR(CDCl$_3$): δ22.81, 22.89, 24.44, 42.89, 51.88, 51.96, 76.77, 77.85, 104.38

(3) Synthesis of (4R,5R)-4,5-bis(aminomethyl)-2-isobutyl-1,3-dioxolane 2.71 g(11.3 mmol) of (4R,5R)-4,5-bis(azidomethyl)-2-isobutyl-1,3-dioxolane was reduced in the same manner as described in Preparative Example 1 to give 2.12 g of (4R,5R)-4,5-bis(aminomethyl)-2-isobutyl-1,3-dioxolane as an oil.

Yield: 100% IR(neat): 3370, 3295 cm$^{-1}$ (NH$_2$) $^1$H NMR(CDCl$_3$): δ0.95(d, J=6.6 Hz, 6H, 2 CH$_3$), 1.55(dd, J=4.9 Hz, J=6.8 Hz, 2H, CH$_2$), 1.81(m, 1H, CH), 2.03(s, 4H, 2 NH$_2$), 2.73–2.93 (m, 4H, 2 NH$_2$), 3.73(br s, 2H, 2 CH), 5.06(t, J=4.9 Hz, 1H, CH) $^{13}$C NMR(CDCl$_3$): δ22.98, 24.46, 43.06, 43.78, 44.13, 79.88, 80.89, 103.07

(4) Synthesis of cis-diiodo[(4R,5R)-4,5-bis(aminomethyl)-2-isobutyl-1,3-dioxolane]platinum(II)

2.11 g(11.2 mmol) of (4R,5R)-4,5-bis(aminomethyl)-2-isobutyl-1,3-dioxolane was reacted with an aqueous solution of potassium tetraiodoplatinate(II) in the same manner as described in Preparative Example 1 to give 5.36 g of cis-diiodo[(4R,5R)-4,5-bis(aminomethyl)-2-isobutyl-1,3-dioxolane]platinum(II) as a yellow solid.

Yield: 89%

Preparative Example 19

(1) Synthesis of 2,3-O-neopentylidene-D-threitol 1,4-bis(methanesulfonate)

3.50 g(12.6 mmol) of D-threitol 1,4-bis(methanesulfonate) was reacted with trimethylacetaldehyde(1.19 g, 13.8 mmol, 1.50 ml) in the same manner as described in Preparative Example 17 to give 2.08 g of 2,3-O-neopentylidene-D-threitol 1,4-bis(methanesulfonate) as white crystals.

Yield: 48% m.p.: 100.0° C. IR(KBr): 1358, 1331, 1181 cm$^{-1}$ (O—SO$_2$) $^1$H NMR(CDCl$_3$): δ0.92(s, 9H, 3 CH$_3$), 3.07(s, 3H, SO$_2$CH$_3$), 3.08(s, 3H, SO$_2$CH$_3$), 4.10–4.24(m, 2H, 2 CH), 4.24–4.50(m, 4H, 2 CH$_2$), 4.74(s, 1H, CH) $^{13}$C NMR(CDCl$_3$): δ24.06, 34.19, 37.74, 37.79, 67.81, 67.91, 75.49, 75.67, 110.98

(2) Synthesis of (4R,5R)-4,5-bis(azidomethyl)-2-tert-butyl-1,3-dioxolane 1.98 g(5.7 mmol) of 2,3-O-neopentylidene-D-threitol 1,4-bis(methanesulfonate) was reacted with sodium azide in the same manner as described in Preparative Example 1 to give 1.36 g of (4R,5R)-4,5-bis(azidomethyl)-2-tert-butyl-1,3-dioxolane as a light yellow oil.

Yield: 99% [α]$_D^{20}$=+104.69° (acetone) IR(neat): 2103 cm$^{-1}$ (N$_3$) $^1$H NMR(CDCl$_3$): δ0.94(s, 9H, 3 CH$_3$), 3.32–3.49(m, 4H, 2 CH$_2$), 3.92–4.04(m, 2H, 2 CH), 4.74(s, 1H, CH) $^{13}$C NMR(CDCl$_3$): δ24.05, 34.16, 51.73, 51.88, 77.31, 77.91, 110.53

(3) Synthesis of (4R,5R)-4,5-bis(aminomethyl)-2-tert-butyl-1,3-dioxolane 1.29 g(5.4 mmol) of (4R,5R)-4,5-bis(azidomethyl)-2-tert-butyl-1,3-dioxolane was reduced in the same manner as described in Preparative Example 1 to give 1.00 g of (4R,5R)-4,5-bis(aminomethyl)-2-tert-butyl-1,3-dioxolane as an oil.

Yield: 99% IR(neat): 3366, 3295 cm$^{-1}$ (NH$_2$) $^1$H NMR(CDCl$_3$): δ0.92(s, 9H, 3 CH$_3$), 1.49(s, 4H, 2 NH$_2$), 2.70–3.00(m, 4H, 2 CH$_2$), 3.66–3.80(m, 2H, 2 CH), 4.66(s, 1H, CH) $^{13}$C NMR(CDCl$_3$): δ24.31, 34.33, 44.03, 44.18, 80.43, 80.96, 109.50

(4) Synthesis of cis-diiodo[(4R,5R)-4,5-bis(aminomethyl)-2-tert-butyl-1,3-dioxolane]platinum(II)

0.99 g(5.3 mmol) of (4R,5R)-4,5-bis(aminomethyl)-2-tert-butyl-1,3-dioxolane was reacted with an aqueous solution of potassium tetraiodoplatinate(II) in the same manner as described in Preparative Example 1 to give 2.55 g of cis-diiodo[(4R,5R)-4,5-bis(aminomethyl)-2-tert-butyl-1,3-dioxolane]platinum(II) as a yellow solid.

Yield: 90%

The compounds prepared in accordance with the process described in the above working examples were assayed on their anti-tumor activity in vitro and in vivo; and solubility in water and toxicity were also determined, as demonstrated below.

1. Growth inhibition test on cultured murine leukemia L1210 cells

Murine leukemia L1210 cells(1×10$^5$) were treated with various concentrations of the compounds prepared in the above examples in RPMI 1640 medium supplemented with 10% fetal calf serum, and cultured in a 5% CO$_2$ humidified incubator at 37° C. for 48 hours. Their viability, estimated by staining with 0.17% Trypan blue, was compared with that of control cells cultured in the identical medium without the compounds. The assays were carried out using at least six different concentrations, and the IC$_{50}$ values (the concentrations in μg/ml required for 50% inhibition of growth) were calculated from their logarithmic dose-response curves. The results are shown in Table 1.

TABLE 1

| Compound | IC$_{50}$ (μg/ml) |
|---|---|
| Example 1 | 0.36 |
| Example 2 | 0.15 |
| Example 3 | 0.10 |
| Example 4 | 0.08 |
| Example 5 | 0.35 |
| Example 6 | 0.22 |
| Example 7 | 0.06 |
| Example 8 | 0.06 |
| Example 9 | 0.08 |
| Example 10 | 0.13 |
| Example 11 | 0.10 |
| Example 12 | 0.10 |
| Example 13 | 0.55 |
| Example 14 | 0.46 |
| Example 15 | 0.33 |
| Example 16 | 0.34 |
| Example 17 | 0.44 |
| Example 18 | 0.32 |
| Example 19 | 0.29 |
| Example 20 | 1.28 |
| Example 21 | 2.08 |
| Example 22 | 0.90 |
| Example 23 | 1.75 |
| Example 24 | 0.55 |
| Example 25 | 1.02 |
| Example 26 | 0.65 |
| Example 27 | 2.36 |
| Example 28 | 1.14 |
| Example 29 | 2.12 |
| Example 30 | 0.55 |
| Example 31 | 1.75 |
| Example 32 | 1.05 |
| Example 33 | 0.50 |
| Example 34 | 0.60 |
| Example 35 | 0.44 |
| Example 36 | 0.76 |
| Example 37 | 0.42 |
| Example 38 | 0.43 |
| Example 39 | 0.31 |
| Example 40 | 0.52 |
| Example 41 | 0.44 |
| Example 42 | 0.54 |
| Example 43 | 0.72 |
| Example 44 | 0.47 |
| Example 45 | 1.40 |
| Example 46 | 2.23 |
| cisplatin | 0.06 |
| carboplatin | 1.98 |

As shown in Table 1, the compounds of the present invention have a potent ability to inhibit the growth of cancer cells at a low concentration.

2. Antitumor activity test on murine leukemia L1210 in vivo

Murine leukemia L1210 cells were maintained in the peritoneal cavities of 6-week-old male DBA/2 mice by weekly transfer in accordance with the procedure described in cancer chemotherapy Reports, Part 3, 3(2), 7 (1972). Specifically, 1×10$^6$ leukemia cells were inoculated into the abdominal cavities of 6-week-old male BDF$_1$ mice weighing 21±3 g on day 0. Each treatment group consisted of seven mice. The test compounds were dissolved or suspended in 0.5% carboxymethyl cellulose(CMC) solution (in water) and were administered intraperitoneally on days 1, 5, and 9 relative to the tumor inoculation.

Thirty mice of 6-week-old male BDF$_1$ weighing 21±3 g were used as the control group, which were injected with 0.5% CMC solution only in the same manner as above.

Anti-tumor activities of the compounds were evaluated in terms of the T/C % values calculated from the mean survival time(T) of the compound-treated group over that(C) of the control group.

$$T/C(\%) = \frac{\text{Mean survival time of compound-treated group}}{\text{Mean survival time of control group}} \times 100$$

TABLE 2

| Compound | Dose (mg/kg) T/C (%) | | | | | | |
|---|---|---|---|---|---|---|---|
| | 1.5 | 3.1 | 6.2 | 12.5 | 25 | 50 | 100 |
| Example 1 | ND | 95 | 132 | 137 | 160 | toxic | ND |
| Example 2 | ND | 112 | 179 | 201 | toxic | toxic | ND |
| Example 3 | ND | 154 | 161 | 295 | toxic | toxic | ND |
| Example 4 | ND | 102 | 146 | 233 | 231 | toxic | ND |
| Example 5 | ND | 104 | 136 | 154 | 167 | toxic | ND |
| Example 6 | ND | 113 | 162 | 205 | toxic | toxic | ND |
| Example 7 | ND | 155 | 166 | 191 | toxic | toxic | ND |
| Example 8 | ND | 154 | 198 | 245 | toxic | toxic | ND |
| Example 9 | ND | 148 | 187 | 231 | toxic | toxic | ND |
| Example 10 | ND | 154 | 161 | 201 | toxic | toxic | ND |
| Example 11 | ND | 102 | 146 | 191 | toxic | toxic | ND |
| Example 12 | ND | 104 | 136 | 154 | 167 | toxic | ND |
| Example 13 | ND | ND | ND | 178 | 207 | 92 | ND |
| Example 14 | ND | ND | ND | 213 | toxic | toxic | ND |
| Example 15 | ND | ND | ND | 225 | 243 | 192 | ND |
| Example 16 | ND | ND | ND | 204 | 227 | toxic | ND |
| Example 17 | ND | ND | ND | 201 | 327 | 139 | ND |
| Example 18 | ND | ND | ND | 206 | 165 | toxic | ND |
| Example 19 | ND | ND | ND | 208 | 232 | toxic | ND |
| Example 20 | ND | ND | 122 | 187 | 137 | 193 | 271 |
| Example 22 | ND | ND | 125 | 129 | 247 | 262 | 382 |
| Example 23 | ND | ND | 108 | 115 | 150 | 201 | 254 |
| Example 24 | ND | ND | 122 | 130 | 193 | 208 | 391 |
| Example 26 | ND | ND | 124 | 170 | 217 | 283 | 317 |
| Example 27 | ND | ND | 112 | 106 | 124 | 148 | 142 |
| Example 28 | ND | ND | 113 | 106 | 126 | 133 | 130 |
| Example 30 | ND | ND | 109 | 122 | 110 | 148 | 185 |
| Example 31 | ND | ND | 102 | 109 | 94 | 106 | 117 |
| Example 33 | ND | ND | ND | 146 | 133 | 276 | ND |
| Example 34 | ND | ND | ND | 140 | 156 | 241 | ND |
| Example 35 | ND | ND | ND | 144 | 204 | 245 | ND |
| Example 36 | ND | ND | ND | 133 | 179 | 190 | ND |
| Example 37 | ND | ND | ND | 130 | 180 | 231 | ND |
| Example 38 | ND | ND | ND | 123 | 148 | 220 | ND |
| Example 39 | ND | ND | ND | 217 | 169 | 203 | ND |
| Example 40 | ND | ND | ND | ND | 213 | 165 | 248 |
| Example 41 | ND | ND | ND | ND | 123 | 174 | 204 |
| Example 42 | ND | ND | ND | ND | 172 | 160 | 150 |
| Example 43 | ND | ND | ND | ND | 197 | 245 | toxic |
| Example 44 | ND | ND | ND | ND | 137 | 169 | 243 |
| Example 45 | ND | ND | ND | ND | 147 | 232 | 216 |
| cisplatin | 142 | 167 | 82 | toxic | toxic | ND | ND |
| carboplatin | ND | ND | 107 | 125 | 148 | 196 | 197 |

*ND: Not Determined

As shown in Table 2, the compounds of the present invention have an excellent life prolongation effect for mice inoculated with murine leukemia L1210 cells.

3. Test for water solubility

A standard plot of UV absorbance(220 nm) vs. concentration was made; and employed to determine water-solubility. The standard solution was made in water or 10% ethanol in water (in case of a compound with poor solubility).

For the solubility study, saturated solutions in water were prepared by vortex mixing the compounds in water for 60 sec., then ultrasonification for 60 sec., vortex mixing for 180 sec., ultrasonification for 60 sec., and finally vortex mixing for 5 min. The mixture was then passed through a 0.45 micron disposable membrane filter before dilution and UV measurement. The water-solubility data measured with the compounds prepared in the working examples are shown in Table 3 hereof.

TABLE 3

| Compound | Solubility in water (mg/ml, 20° C.) |
|---|---|
| Example 1 | >30 |
| Example 2 | 17.5 |
| Example 3 | 5.8 |
| Example 4 | 2.9 |
| Example 5 | >50 |
| Example 6 | >50 |
| Example 7 | >30 |
| Example 8 | >30 |
| Example 9 | 11.6 |
| Example 10 | >30 |
| Example 11 | 4.6 |
| Example 12 | 2.1 |
| Example 13 | >100 |
| Example 14 | >100 |
| Example 15 | 4.9 |
| Example 16 | 3.8 |
| Example 17 | >100 |
| Example 18 | >100 |
| Example 19 | >100 |
| Example 20 | 3.1 |
| Example 21 | 3.1 |
| Example 22 | 24.9 |
| Example 23 | 22.1 |
| Example 24 | 12.0 |
| Example 25 | 11.8 |
| Example 26 | 2.0 |
| Example 27 | 1.9 |
| Example 28 | 2.1 |
| Example 29 | 2.0 |
| Example 30 | 1.9 |
| Example 31 | 1.9 |
| Example 32 | 0.9 |
| Example 33 | 21.9 |
| Example 34 | >50 |
| Example 35 | >30 |
| Example 36 | 27.1 |
| Example 37 | 2.0 |
| Example 38 | 4.1 |
| Example 39 | 5.3 |
| Example 40 | 11.3 |
| Example 41 | >30 |
| Example 42 | 6.7 |
| Example 43 | 7.9 |
| Example 44 | 7.8 |
| Example 45 | 2.7 |
| Example 46 | 0.9 |
| Cisplatin | 1.2 |
| Carboplatin | 10.0 |

As shown in Table 3, a large number of the compounds of the present invention have a good solubility in water.

4. Test for nephrotoxicity

The compounds of the present invention were dissolved or suspended in 0.5% CMC solution(in water) and were administered intraperitoneally one time to 8-week-old male ICR mice weighing 30±3 g. Each treatment and control groups consisted of six mice.

The administration amount of the test compound was 1.5 times the optimum dose obtained in Table 2, or more. On days 1, 4 and 8 after administration, their blood was collected under ether anesthesia for measurement of blood urea nitrogen concentration (BUN value) and creatinine concentration. The results are shown in Table 4.

A pair of kidneys were taken and, after immediate weighing, were stored in a 10% neutral buffered formalin solution. The results are shown in Table 5. The body weight ratio shown in Table 5 is a ratio of the body weight measured on days 1, 4 and 8 from the administration of the compound to the body weight measured on the administration day.

TABLE 4

| Compound | Dose (mg/kg) | No. of mice employed | BUN (mg/100 ml)[a] 1st day | BUN (mg/100 ml)[a] 4th day | BUN (mg/100 ml)[a] 8th day | Creatinine (mg/100 ml)[a] 1st day | Creatinine (mg/100 ml)[a] 4th day | Creatinine (mg/100 ml)[a] 8th day |
|---|---|---|---|---|---|---|---|---|
| Control | 0.5% CMC | 6 | 26.0 ± 1.3 | 29.7 ± 2.2 | 27.8 ± 2.1 | | | |
| Example 1 | 37.5 | 6 | 28.07 ± 0.98 | 94.42 ± 45.22 | 27.44 ± 2.79 | | | |
| Example 2 | 18.8 | 6 | 25.87 ± 1.45 | 22.13 ± 2.22 | 31.13 ± 2.73 | | | |
| Example 3 | 18.8 | 6 | 26.45 ± 0.08 | 20.04 ± 0.55 | 40.86[c] ± 3.88 | | | |
| Example 4 | 37.5 | 6 | 24.23 ± 0.64 | 22.13 ± 1.44 | 25.54 ± 1.23 | | | |
| Example 5 | 37.5 | 6 | 25.33 ± 1.63 | 73.66 ± 25.47 | 28.70 ± 0.97 | | | |
| Example 6 | 18.8 | 6 | 22.41 ± 1.00 | 22.67 ± 1.18 | 30.41 ± 0.92 | | | |
| Example 7 | 18.8 | 6 | 23.69 ± 1.28 | 22.04 ± 1.21 | 31.73 ± 1.51 | | | |
| Example 8 | 18.8 | 6 | 27.1 ± 1.2 | 22.4 ± 4.2 | 28.4 ± 1.5 | | | |
| Example 9 | 18.8 | 6 | 26.2 ± 1.4 | 21.8 ± 5.2 | 30.1 ± 1.7 | | | |
| Example 15 | 18.8 | 6 | 19.4[b] ± 1.1 | 22.1[c] ± 1.1 | 27.1 ± 1.9 | | | |
| Example 19 | 18.8 | 6 | 38.6[b] ± 1.6 | 27.9 ± 5.2 | 50.7 ± 17.3 | | | |
| Example 20 | 150 | 6 | 25.4 ± 3.4 | 64.3[c] ± 15.7 | 30.1 ± 3.1 | 0.30 ± 0.04 | 0.53[c] ± 0.09 | 0.28 ± 0.05 |
| Example 22 | 150 | 6 | 26.0 ± 1.3 | 36.0 ± 3.9 | 26.7 ± 2.8 | 0.28 ± 0.02 | 0.25 ± 0.02 | 0.23 ± 0.03 |
| Example 23 | 150 | 6 | 24.8 ± 0.9 | 32.1 ± 3.1 | 42.0[b] ± 2.3 | 0.26 ± 0.02 | 0.30 ± 0.01 | 0.28 ± 0.02 |
| Example 24 | 150 | 6 | 26.7 ± 1.6 | 20.9 ± 2.3 | 36.1[c] ± 2.5 | 0.25 ± 0.01 | 0.22 ± 0.02 | 0.30 ± 0.00 |
| Example 26 | 150 | 6 | 26.7 ± 2.2 | 23.7 ± 6.0 | 30.0 ± 1.6 | 0.24 ± 0.05 | 0.22 ± 0.04 | 0.27 ± 0.02 |
| Example 27 | 150 | 6 | 28.9 | 27.2 | 35.3[b] | 0.23 | 0.28 | 0.29 |

TABLE 4-continued

| Compound | Dose (mg/kg) | No. of mice employed | BUN (mg/100 ml)[a] | | | Creatinine (mg/100 ml)[a] | | |
|---|---|---|---|---|---|---|---|---|
| | | | 1st day | 4th day | 8th day | 1st day | 4th day | 8th day |
| | | | ± 1.8 | ± 2.3 | ± 0.5 | ± 0.02 | ± 0.02 | ± 0.02 |
| Example 30 | 150 | 6 | 33.0[c] | 21.4 | 30.7 | 0.32 | 0.20 | 0.31 |
| | | | ± 2.1 | ± 3.2 | ± 3.1 | ± 0.04 | ± 0.03 | ± 0.02 |
| Example 31 | 150 | 6 | 43.1[b] | all dead | all dead | 0.35 ± 1.3 | all dead | all dead |
| | | | ± 5.8 | | | | | |
| Example 37 | 75.0 | 6 | 27.5 | 26.4 | 28.4 | | | |
| | | | ± 2.2 | ± 3.2 | ± 1.7 | | | |
| Example 38 | 75.0 | 6 | 22.6 | 27.0 | 28.3 | | | |
| | | | ± 1.6 | ± 2.2 | ± 1.5 | | | |
| Example 39 | 75.0 | 6 | 26.5 | 29.1 | 23.7 | | | |
| | | | ± 1.2 | ± 4.2 | ± 1.5 | | | |
| Cisplatin | 6 | 6 | 42.8[c] | 343.0[b] | 38.3[c] | 0.32 | 2.86[b] | 0.35 |
| | | | ± 5.5 | ± 82.9 | ± 0.8 | ± 0.04 | ± 0.44 | ± 0.05 |

[a]:The values are the means plus or minus standard error in milligrams per 100 ml of blood
[b]:Significantly different from control group; $p < 0.01$
[c]:Significantly different from control group; $p < 0.05$

TABLE 5

| Compound | Dose (mg/kg) | 1st day | | 4th day | | 8th day | |
|---|---|---|---|---|---|---|---|
| | | BWR[a] | Kidney wt[b] | BWR[a] | Kidney wt[b] | BWR[a] | Kidney wt[b] |
| Control | — | 1.00 | 528 ± 24.5 | 1.01 | 563 ± 26.0 | 1.08 | 530 ± 25.6 |
| Example 20 | 150 | 0.95 | 470 ± 62.0 | 0.79 | 465 ± 19.5[c] | 0.93 | 552 ± 39.0 |
| Example 22 | 150 | 0.98 | 497 ± 17.2 | 0.82 | 425 ± 12.5[c] | 0.97 | 465 ± 31.8 |
| Example 23 | 150 | 0.98 | 492 ± 22.7 | 0.96 | 535 ± 16.3 | 0.99 | 527 ± 13.8 |
| Example 24 | 150 | 0.96 | 487 ± 19.0 | 0.97 | 538 ± 23.6 | 1.02 | 532 ± 30.7 |
| Example 26 | 150 | 0.97 | 532 ± 29.8 | 0.85 | 457 ± 41.0 | 1.03 | 516 ± 24.4 |
| Example 27 | 150 | 0.96 | 497 ± 22.8 | 0.98 | 547 ± 20.6 | 1.00 | 530 ± 35.0 |
| Example 30 | 150 | 0.99 | 485 ± 20.8 | 0.90 | 487 ± 39.0 | 1.04 | 542 ± 22.5 |
| Example 31 | 150 | 0.94 | 485 ± 15.0 | all dead | all dead | all dead | all dead |
| Cisplatin | 6 | 0.94 | 471 ± 22.1 | 0.82 | 420 ± 6.3[c] | 0.88 | 475 ± 42.9 |

Note>
[a]:BWR: body weight ratio.
[b]:Paired weight (mg): the values are the means plus or minus standard error.
[c]:Significantly different from the control group; $p < 0.05$.

As shown in Tables 4 and 5, the BUN and the creatinine values obtained for the compounds tested were lower than the value obtained for cisplatin; and close to the values obtained with the control group administered with 0.5% CMC solution (in water); and kidney weight was slightly reduced. These results indicate that the present compounds have very low nephrotoxicity.

Acute toxicity test 7-week-old ICR mice(male: 34±2 g; female: 31±2 g) were fed with solid food and water under the condition of 23±1° C. temperature and 65±5% humidity before the test.

Each treatment group consisted of 6 mice. The test compounds were administered intraperitoneally.

For 7 days after the administration, the appearance and the fate of the tested animals were recorded. The dead animals were subjected to autopsy and their visible pathological changes were observed. Their viscerals were stored in 10% formalin solution. The results are as shown in Table 6.

TABLE 6

| Compound | Sex | Dose (mg/kg) | Number of dead mice | | | | | | | Lethality | LD$_{50}$ |
|---|---|---|---|---|---|---|---|---|---|---|---|
| | | | 1st day | 2nd day | 3rd day | 4th day | 5th day | 6th day | for 7 days | | |
| Example 1 | male | 25.0 | 0/6 | | | | | | 0/6 | | |
| | | 32.5 | 0/6 | | | | | | 0/6 | | |
| | | 42.3 | 0/6 | | | 1/6 | | | 1/6 | 16.7 | 61.7 |
| | | 55.0 | 0/6 | | 2/6 | | | | 2/6 | 33.3 | |
| | | 71.4 | 0/6 | | 3/6 | 1/3 | | | 4/6 | 66.7 | |
| | female | 25.0 | 0/6 | | | | | | 0/6 | | |
| | | 32.5 | 0/6 | | | | | | 0/6 | | |
| | | 42.3 | 0/6 | | | 1/6 | | | 1/6 | 16.7 | 68.0 |
| | | 55.0 | 0/6 | | 2/6 | | | | 2/6 | 33.3 | |
| | | 71.4 | 0/6 | | 2/6 | 1/4 | | | 3/6 | 50.0 | |
| Example 2 | male | 25.0 | 0/6 | | | | | | 0/6 | | |
| | | 32.5 | 0/6 | | 1/6 | 1/5 | 1/4 | | 3/6 | 50.0 | |
| | | 42.3 | 0/6 | | 3/6 | 2/3 | | | 5/6 | 83.3 | 34.0 |
| | | 55.0 | 0/6 | | 4/6 | 1/2 | 1/1 | | 6/6 | 100.0 | |
| | | 71.4 | 0/6 | | 4/6 | 2/2 | | | 6/6 | 100.0 | |
| | female | 25.0 | 0/6 | | | | | | 0/6 | | |
| | | 32.5 | 0/6 | | 2/6 | 1/4 | | | 3/6 | 50.0 | |
| | | 42.3 | 0/6 | | 3/6 | 1/3 | | | 4/6 | 66.7 | 35.4 |
| | | 55.0 | 0/6 | | 4/6 | 1/2 | 1/1 | | 6/6 | 100.0 | |
| | | 71.4 | 0/6 | | 4/6 | 2/2 | | | 6/6 | 100.0 | |
| Example 3 | male | 25.0 | 0/6 | | | | | | 0/6 | | |
| | | 32.5 | 0/6 | | | 1/6 | | | 0/6 | | |
| | | 42.3 | 0/6 | | | 1/6 | | | 2/6 | 33.3 | 43.5 |

TABLE 6-continued

| Compound | Sex | Dose (mg/kg) | Number of dead mice | | | | | | | Lethality | LD$_{50}$ |
|---|---|---|---|---|---|---|---|---|---|---|---|
| | | | 1st day | 2nd day | 3rd day | 4th day | 5th day | 6th day | for 7 days | | |
| | | 55.0 | 0/6 | | 4/6 | 1/2 | 1/1 | | 6/6 | 100.0 | |
| | | 71.4 | 0/6 | | 4/6 | 2/2 | | | 6/6 | 100.0 | |
| | female | 25.0 | 0/6 | | | | | | 0/6 | | |
| | | 32.5 | 0/6 | | | | | | 0/6 | | |
| | | 42.3 | 0/6 | | | 1/6 | 1/5 | | 2/6 | 33.3 | 46.4 |
| | | 55.0 | 0/6 | | 4/6 | 1/2 | | | 5/6 | 83.2 | |
| | | 71.4 | 0/6 | | 4/6 | 2/2 | | | 6/6 | 100.0 | |
| Example 4 | male | 25.0 | 0/6 | | | | | | 0/6 | | |
| | | 32.5 | 0/6 | | | | | | 0/6 | | |
| | | 42.3 | 0/6 | | | | | | 0/6 | | 60.2 |
| | | 55.0 | 0/6 | 2/6 | 1/4 | | | | 3/6 | 50.0 | |
| | | 71.4 | 0/6 | 3/6 | 1/3 | | | | 4/6 | 66.7 | |
| | female | 25.0 | 0/6 | | | | | | 0/6 | | |
| | | 32.5 | 0/6 | | | | | | 0/6 | | |
| | | 42.3 | 0/6 | | | | | | 0/6 | | 63.3 |
| | | 55.0 | 0/6 | | 1/6 | 1/5 | | | 2/6 | 33.3 | |
| | | 71.4 | 0/6 | 2/6 | 1/4 | 1/3 | | | 4/6 | 66.7 | |
| Example 5 | male | 25.0 | 0/6 | | | | | | 0/6 | | |
| | | 32.5 | 0/6 | | | | | | 0/6 | | |
| | | 42.3 | 0/6 | | | | | | 0/6 | | 63.3 |
| | | 55.0 | 0/6 | | 1/6 | | | | 1/6 | 16.7 | |
| | | 71.4 | 0/6 | | 3/6 | 1/3 | | | 4/6 | 66.7 | |
| | female | 25.0 | 0/6 | | | | | | 0/6 | | |
| | | 32.5 | 0/6 | | | | | | 0/6 | | |
| | | 42.3 | 0/6 | | | | | | 0/6 | | 70.4 |
| | | 55.0 | 0/6 | | | 1/6 | | | 1/6 | 16.7 | |
| | | 71.4 | 0/6 | | 2/6 | 1/4 | | | 3/6 | 50.0 | |
| Example 6 | male | 25.0 | 0/6 | | | | | | 0/6 | | |
| | | 32.5 | 0/6 | | 1/6 | | | | 0/6 | 16.7 | |
| | | 42.3 | 0/6 | | 1/6 | 2/5 | 1/3 | | 4/6 | 66.7 | 38.5 |
| | | 55.0 | 0/6 | | 4/6 | 1/2 | 1/1 | | 6/6 | 100.0 | |
| | | 71.4 | 0/6 | | 4/6 | 2/2 | | | 6/6 | 100.0 | |
| | female | 25.0 | 0/6 | | | | | | 0/6 | | |
| | | 32.5 | 0/6 | | 1/6 | | | | 1/6 | 16.7 | |
| | | 42.3 | 0/6 | | 1/6 | 1/5 | 1/4 | | 3/6 | 50.0 | 42.3 |
| | | 55.0 | 0/6 | | 4/6 | 1/2 | | | 5/6 | 83.3 | |
| | | 71.4 | 0/6 | | 4/6 | 2/2 | | | 6/6 | 100.0 | |
| Example 7 | male | 25.0 | 0/6 | | | | | | 0/6 | | |
| | | 32.5 | 0/6 | | | | | | 0/6 | | |
| | | 42.3 | 0/6 | | 1/6 | | 1/5 | | 2/6 | 33.3 | 60.0 |
| | | 55.0 | 0/6 | | 1/6 | 1/5 | | | 2/6 | 33.3 | |
| | | 71.4 | 0/6 | | 2/6 | 2/4 | | | 4/6 | 66.7 | |
| | female | 25.0 | 0/6 | | | | | | 0/6 | | |
| | | 32.5 | 0/6 | | | | | | 0/6 | | |
| | | 42.3 | 0/6 | | 1/6 | | | | 1/6 | 16.7 | 61.7 |
| | | 55.0 | 0/6 | | 1/6 | 1/5 | | | 2/6 | 33.3 | |
| | | 71.4 | 0/6 | | 3/6 | 1/3 | | | 4/6 | 66.7 | |
| Example 8 | male | 41.3 | 0/6 | | | | | | 0/6 | 0.0 | |
| | | 54.9 | 0/6 | | 2/6 | 2/4 | | | 4/6 | 66.7 | |
| | | 71.4 | 0/6 | | 1/6 | 4/5 | | | 5/6 | 83.3 | 54.2 |
| | | 91.8 | 0/6 | 2/6 | 4/4 | | | | 6/6 | 100.0 | |
| | female | 41.3 | 0/6 | | | | | | 0/6 | 0.0 | |
| | | 54.9 | 0/6 | | 1/6 | 2/5 | | | 3/6 | 50.0 | |
| | | 71.4 | 0/6 | | | 2/6 | 3/4 | | 5/6 | 83.7 | 57.2 |
| | | 91.8 | 0/6 | 1/6 | 3/5 | 2/2 | | | 6/6 | 100.0 | |
| Example 9 | male | 41.3 | 0/6 | | | 2/6 | 1/4 | | 0/6 | 0.0 | |
| | | 54.9 | 0/6 | | | 2/6 | 2/4 | | 4/6 | 66.7 | |
| | | 71.4 | 0/6 | | | 1/6 | 2/5 | 2/3 | 5/6 | 83.3 | 43.7 |
| | | 91.8 | 0/6 | 1/6 | 4/5 | 1/1 | | | 6/6 | 100.0 | |
| | female | 41.3 | 0/6 | | | 2/6 | | | 2/6 | 0.0 | |
| | | 54.9 | 0/6 | | 1/6 | 3/5 | | | 4/6 | 50.0 | |
| | | 71.4 | 0/6 | | 1/6 | 3/5 | 1/2 | | 5/6 | 83.7 | 48.3 |
| | | 91.8 | 0/6 | | 2/6 | 4/4 | | | 6/6 | 100.0 | |
| Example 15 | male | 41.3 | 0/6 | | | | | | 0/6 | 0.0 | |
| | | 54.9 | 0/6 | | 2/6 | | | 2/4 | 4/6 | 66.7 | |
| | | 71.4 | 0/6 | | | 4/6 | 1/2 | | 5/6 | 83.3 | 54.2 |
| | | 91.8 | 0/6 | 2/6 | 3/4 | 1/1 | | | 6/6 | 100.0 | |
| | female | 41.3 | 0/6 | | | | | | 0/6 | 0.0 | |
| | | 54.9 | 0/6 | | 1/6 | 1/5 | 1/4 | | 3/6 | 50.0 | |
| | | 71.4 | 0/6 | | | 1/6 | 3/5 | 1/2 | 5/6 | 83.7 | 57.2 |
| | | 91.8 | 0/6 | 1/6 | 2/5 | 2/3 | 1/1 | | 6/6 | 100.0 | |
| Example 18 | male | 41.3 | 0/6 | | | 1/6 | 1/5 | 2/4 | 4/6 | 66.7 | |
| | | 54.9 | 0/6 | 1/6 | 1/5 | 1/4 | 1/3 | | 4/6 | 66.7 | |
| | | 71.4 | 0/6 | | | 2/6 | 2/4 | 1/2 | 5/6 | 83.3 | 36.3 |
| | | 91.8 | 0/6 | 3/6 | | 1/3 | 1/2 | 1/1 | 6/6 | 100.0 | |
| | female | 41.3 | 0/6 | | | | 1/6 | 2/5 | 3/6 | 55.0 | |
| | | 54.9 | 0/6 | | 1/6 | 2/5 | 1/3 | | 4/6 | 66.7 | |
| | | 71.4 | 0/6 | | | 1/6 | 3/5 | 1/2 | 5/6 | 83.3 | 43.7 |
| | | 91.8 | 1/6 | 1/6 | 2/5 | 2/3 | 1/1 | | 6/6 | 100.0 | |
| Example 19 | male | 41.3 | 0/6 | | | | 1/6 | 2/5 | 3/6 | 50.0 | |

TABLE 6-continued

| Compound | Sex | Dose (mg/kg) | Number of dead mice | | | | | | | Lethality | $LD_{50}$ |
|---|---|---|---|---|---|---|---|---|---|---|---|
| | | | 1st day | 2nd day | 3rd day | 4th day | 5th day | 6th day | for 7 days | | |
| | | 54.9 | 0/6 | | | 1/6 | 2/5 | 1/3 | 4/6 | 66.7 | |
| | | 71.4 | 0/6 | | | 1/6 | 2/5 | 2/3 | 5/6 | 83.7 | 43.7 |
| | | 91.8 | 0/6 | 1/6 | 4/5 | | 1/1 | | 6/6 | 100.0 | |
| | female | 41.3 | 0/6 | | | | 1/6 | 1/5 | 2/6 | 33.3 | |
| | | 54.9 | 0/6 | | 1/6 | 2/5 | 1/3 | | 4/6 | 66.7 | |
| | | 71.4 | 0/6 | | | 1/6 | 3/5 | 1/2 | 5/6 | 83.3 | 48.3 |
| | | 91.8 | 0/6 | 1/6 | 2/5 | 2/3 | 1/1 | | 6/6 | 100.0 | |
| Example 20 | male | 94 | 0/6 | | | | | | 0/6 | | |
| | | 123 | 1/6 | | | | 1/5 | | 2/6 | 33.3 | |
| | | 160 | 0/6 | | | 2/6 | 1/4 | 2/3 | 5/6 | 83.3 | 141.6 |
| | | 208 | 0/6 | | | 6/6 | | | 6/6 | 100.0 | |
| | | 270 | 0/6 | 4/6 | 2/2 | | | | 6/6 | 100.0 | |
| | female | 94 | 0/6 | | | | | | 0/6 | | |
| | | 123 | 0/6 | | | 2/6 | | | 2/6 | 33.3 | |
| | | 160 | 0/6 | | | 2/6 | 2/4 | | 4/6 | 66.7 | 144.2 |
| | | 208 | 0/6 | | 1/6 | 5/5 | | | 6/6 | 100.0 | |
| | | 270 | 0/6 | 4/6 | 2/2 | | | | 6/6 | 100.0 | |
| Example 22 | male | 94 | 0/6 | | | | | | 0/6 | | |
| | | 123 | 0/6 | | | | | | 0/6 | | |
| | | 160 | 1/6 | | | 1/5 | 1/4 | 1/3 | 4/6 | 66.7 | 168.6 |
| | | 208 | 0/6 | | | 4/6 | 1/2 | | 5/6 | 83.3 | |
| | | 270 | 0/6 | 2/6 | 4/4 | | | | 6/6 | 100.0 | |
| | female | 94 | 0/6 | | | | | | 0/6 | | |
| | | 123 | 0/6 | | | 1/6 | | | 1/6 | 16.7 | |
| | | 160 | 0/6 | | | 2/6 | 1/4 | | 3/6 | 50.0 | 159.7 |
| | | 208 | 0/6 | | 1/6 | 4/5 | | | 5/6 | 83.3 | |
| | | 270 | 0/6 | 4/6 | 2/2 | | | | 6/6 | 100.0 | |
| Example 24 | male | 160 | 0/6 | | | | | | 0/6 | | |
| | | 208 | 0/6 | | 1/6 | | | | 1/6 | 16.7 | |
| | | 270 | 0/6 | 1/6 | 2/5 | 1/3 | 1/2 | | 5/6 | 83.3 | 246.7 |
| | | 352 | 1/6 | 2/5 | 2/3 | | | 1/1 | 6/6 | 100.0 | |
| | | 457 | 0/6 | 2/6 | 4/6 | | | | 6/6 | 100.0 | |
| | female | 160 | 0/6 | | | | | | 0/6 | | |
| | | 208 | 0/6 | | | | | | 0/6 | | |
| | | 270 | 0/6 | 1/6 | 1/5 | | 1/4 | | 3/6 | 50.0 | 289.4 |
| | | 352 | 0/6 | | 3/6 | 2/3 | | | 5/6 | 83.3 | |
| | | 457 | 0/6 | 4/6 | 2/2 | | | | 6/6 | 100.0 | |
| Example 26 | male | 160 | 0/6 | | | | | | 0/6 | | |
| | | 208 | 0/6 | | 1/6 | | | | 1/6 | 16.7 | |
| | | 270 | 0/6 | | | 2/6 | | | 2/6 | 33.3 | 280.6 |
| | | 352 | 0/6 | 1/6 | 3/5 | | | | 4/6 | 66.7 | |
| | | 457 | 0/6 | 2/6 | 4/4 | | | | 6/6 | 100.0 | |
| | female | 160 | 0/6 | | | | | | 0/6 | | |
| | | 208 | 0/6 | | | | | | 0/6 | | |
| | | 270 | 0/6 | | | | 1/6 | | 1/6 | 16.7 | 304.8 |
| | | 352 | 0/6 | | 2/6 | 2/4 | | | 4/6 | 66.7 | |
| | | 457 | 0/6 | 4/6 | 2/2 | | | | 6/6 | 100.0 | |
| Example 30 | male | 94 | 0/6 | | | | | | 0/6 | | |
| | | 123 | 1/6 | | | | | | 0/6 | | |
| | | 160 | 0/6 | | | 1/6 | | | 1/6 | 16.7 | 176.4 |
| | | 208 | 1/6 | 1/6 | 3/5 | | | | 5/6 | 83.3 | |
| | | 270 | 0/6 | 2/6 | 4/4 | | | | 6/6 | 100.0 | |
| | female | 94 | 0/6 | | | | | | 0/6 | | |
| | | 123 | 0/6 | | | | | | 0/6 | | |
| | | 160 | 0/6 | | | 1/6 | | | 1/6 | 16.7 | 180.2 |
| | | 208 | 0/6 | | 2/6 | 2/4 | | | 4/6 | 66.7 | |
| | | 270 | 0/6 | 4/6 | 2/2 | | | | 6/6 | 100.0 | |
| Example 37 | male | 71.4 | 0/6 | | 1/6 | | | | 1/6 | 16.7 | |
| | | 91.8 | 0/6 | | 2/6 | | | 2/4 | 4/6 | 66.7 | 84.5 |
| | | 100.0 | 0/6 | | | 4/6 | 1/2 | | 5/6 | 83.3 | |
| | | 130.0 | 0/6 | 2/6 | 3/4 | 1/1 | | | 6/6 | 100.0 | |
| | female | 100.0 | 0/6 | | | | | | 0/6 | 0.0 | |
| | | 130.0 | 0/6 | | 1/6 | 1/5 | 1/4 | | 3/6 | 50.0 | 93.6 |
| | | 169.0 | 0/6 | | | 1/6 | 3/5 | 1/2 | 5/6 | 83.3 | |
| | | 219.0 | 0/6 | 1/6 | 2/5 | 2/3 | 1/1 | | 6/6 | 100.0 | |
| Example 38 | male | 100.0 | 1/6 | | | 2/6 | 1/4 | | 4/6 | 66.7 | |
| | | 130.0 | 0/6 | | 1/6 | 2/5 | 1/3 | 1/2 | 5/6 | 83.7 | |
| | | 169.0 | 0/6 | | | 2/6 | 3/4 | 1/1 | 6/6 | 100.0 | 86.4 |
| | | 219.0 | 0/6 | 1/6 | 1/5 | 4/4 | | | 6/6 | 100.0 | |
| | female | 100.0 | 0/6 | | | | 1/6 | 2/5 | 3/6 | 50.0 | |
| | | 130.0 | 0/6 | | 1/6 | 2/5 | 1/3 | 1/2 | 5/6 | 83.7 | |
| | | 169.0 | 0/6 | | | 1/6 | 1/5 | 2/2 | 6/6 | 100.0 | 98.1 |
| | | 219.0 | 0/6 | 1/6 | 2/5 | 2/3 | 1/1 | | 6/6 | 100.0 | |
| Example 39 | male | 71.4 | 0/6 | | | | | | 0/6 | 0.0 | |
| | | 91.8 | 0/6 | | 2/6 | | | 1/6 | 3/6 | 50.0 | |
| | | 100.0 | 0/6 | | | 4/6 | 1/6 | | 5/6 | 83.3 | 93.6 |
| | | 130.0 | 0/6 | 2/6 | 3/6 | 1/6 | | | 6/6 | 100.0 | |
| | female | 71.4 | 0/6 | | | | | | 0/6 | 0.0 | |
| | | 91.8 | 0/6 | | 1/6 | 1/6 | | | 2/6 | 50.0 | 94.7 |
| | | 100.0 | 0/6 | | | 1/6 | 3/6 | 1/6 | 5/6 | 83.3 | |

TABLE 6-continued

| Compound | Sex | Dose (mg/kg) | Number of dead mice | | | | | | | Lethality | LD$_{50}$ |
| --- | --- | --- | --- | --- | --- | --- | --- | --- | --- | --- | --- |
| | | | 1st day | 2nd day | 3rd day | 4th day | 5th day | 6th day | for 7 days | | |
| | | 130.0 | 0/6 | 1/6 | 2/6 | 2/6 | 1/6 | | 6/6 | 100.0 | |
| Cisplatin | male | 4.7 | 0/6 | | | | | | 0/6 | | |
| | | 6.0 | 0/6 | | | | | | 0/6 | | |
| | | 7.8 | 0/6 | 1/6 | 2/5 | 1/3 | | | 4/6 | 66.7 | 7.7 |
| | | 10.1 | 0/6 | | 4/6 | 2/3 | | | 6/6 | 100.0 | |
| | | 13.0 | 0/6 | 1/6 | 5/5 | | | | 6/6 | 100.0 | |
| | female | 4.7 | 0/6 | | | | | | 0/6 | | |
| | | 6.0 | 0/6 | | | | | | 0/6 | | |
| | | 7.8 | 0/6 | 1/6 | 1/5 | 1/4 | 1/3 | | 4/6 | 66.7 | 7.7 |
| | | 10.1 | 0/6 | | 3/6 | 2/3 | 1/1 | | 6/6 | 100.0 | |
| | | 13.0 | 0/6 | 1/6 | 4/5 | 1/1 | | | 6/6 | 100.0 | |

As shown in Table 6, the compounds of the present invention have a higher median lethal dose(LD$_{50}$) value than cisplatin; and it is relatively harmless in the dosages of several grams or more.

What is claimed is:

1. A platinum(II) complex compound represented by the formula(1) of:

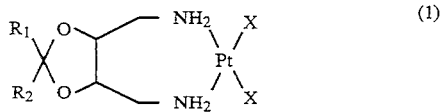

wherein:

R$_1$ and R$_2$, which may be the same or different, are a hydrogen atom or a C$_{1-4}$ alkyl group, respectively, or jointly form a cycloalkane group together with the carbon atom attached thereto;

two Xs jointly form a group represented by the formula of:

or

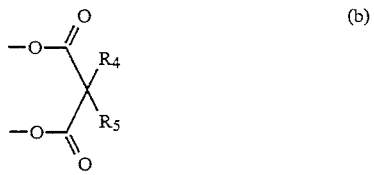

wherein R$_3$ is a hydrogen atom or a methyl group; R$_4$ and R$_5$, which may be the same or different, are a hydrogen atom or a C$_{1-4}$ alkyl group, respectively, or jointly form a cyclobutane together with the carbon atom attached thereto; and the absolute configurations at the respective chiral centers in the 4,5-bis(aminomethyl)-1,3-dioxolane moiety are (4R, 5R) or (4S, 5S).

2. The compound of claim 1, wherein the absolute configurations at the respective chiral centers are (4R,5R).

3. The compound of claim 1, wherein said R$_1$ and R$_2$ jointly form a cyclopentane or cyclohexane group together with the carbon atom attached thereto; both are a methyl group or an ethyl group; or one of said R$_1$ and R$_2$ is an ethyl or isopropyl group and the other is a hydrogen atom.

4. The compound of claim 1, wherein R$_3$ is a hydrogen atom when said two Xs jointly form the group of formula(a), or wherein both R$_4$ and R$_5$ are hydrogens when said two Xs form the group of formula(b).

5. A platinum(II) complex compound having the molecular structure of (glycolato-O,O′)[(4R,5R)-4,5-bis(aminomethyl)-1,3-dioxolane-2-spiro-1′-cyclopentane]platinum(II).

6. A platinum(II) complex compound having the molecular structure of (glycolato-O,O′){cyclohexanespiro-2′-[(4′R,5′R)-4′,5′-bis(aminomethyl)-1′,3′-dioxolane]}platinum(II).

7. A platinum(II) complex compound having the molecular structure of (glycolato-O,O′)[(4R,5R)-4,5-bis(aminomethyl)-2-ethyl-1,3-dioxolane]platinim(II).

8. A platinum(II) complex compound having the molecular structure of (glycolato-O,O′)[(4R,5R)-4,5-bis(aminomethyl)-2-isopropyl-1,3-dioxolane]platinim(II).

9. A platinum(II) complex compound having the molecular structure of (glycolato-O,O′)[(4R,5R)-4,5-bis(aminomethyl)-2,2-diethyl-1,3-dioxolane]platinum(II).

10. A platinum(II) complex compound having the molecular structure of (glycolato-O,O′)[(4R,5R)-4,5-bis(aminomethyl)-2-ethyl-2-methyl-1,3-dioxolane]platinum(II).

11. A platinum(II) complex compound having the molecular structure of (glycolato-O,O′)[(4R,5R)-4,5-bis(aminomethyl)-2-propyl-1,3-dioxolane]platinum(II).

12. A platinum(II) complex compound having the molecular structure of cis-cyclobutane-1,1-dicarboxylato[(4R,5R)-4,5-bis(aminomethyl)-2-ethyl-1,3-dioxolane]platinum(II).

13. A platinum(II) complex compound having the molecular structure of cis-malonato[(4R,5R)-4,5-bis-(aminomethyl)-2,2-diethyl-1,3-dioxolane]platinum(II).

14. A platinum(II) complex compound having the molecular structure of cis-malonato[(4R,5R)-4,5-bis-(aminomethyl)-2-isopropyl-1,3-dioxolane]platinum(II).

15. A platinum(II) complex compound having the molecular structure of cis-malonato[(4R,5R)-4,5-bis-(aminomethyl)-1,3-dioxolane-2-spiro-1′-cyclopentane]platinum(II).

16. A process for preparing a platinum(II) complex compound of the formula(1a), which comprises:

reacting a dihalogenodiamine platinum(II) complex of the formula(2) with an acid having the formula of (L)-R$_3$CHOHCOOH and silver(I) oxide,

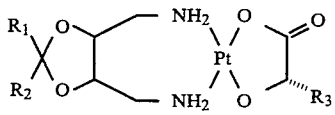 (1a)

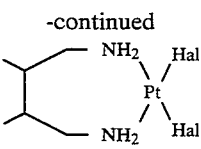 (2)

wherein $R_1$, $R_2$, $R_3$ and the absolute configurations are the same as defined in claim 1 and Hal is a halogen atom.

17. The process of claim 16, wherein said compound of the formula(2) is reacted with said acid and said silver(I) oxide in the equivalent ratio of from 1:0.5:0.5 to 1:5:5, in an aqueous medium or a mixed medium of an aqueous solvent and an alcoholic solvent in a dark environment at a temperature between 0° and 100° C. for about 1 hour to 3 days.

* * * * *